(12) United States Patent
Box et al.

(10) Patent No.: US 7,271,197 B2
(45) Date of Patent: Sep. 18, 2007

(54) PHENETHANOLAMINE DERIVATIVES

(75) Inventors: Philip Charles Box, Stevenage (GB);
Diane Mary Coe, Stevenage (GB);
Brian Edgar Looker, Stevenage (GB);
Panayiotis Alexandrou Procopiou,
Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 260 days.

(21) Appl. No.: 10/512,232

(22) PCT Filed: Apr. 24, 2003

(86) PCT No.: PCT/EP03/04367

§ 371 (c)(1),
(2), (4) Date: Jul. 6, 2005

(87) PCT Pub. No.: WO03/091204

PCT Pub. Date: Nov. 6, 2003

(65) Prior Publication Data
US 2005/0256201 A1    Nov. 17, 2005

(30) Foreign Application Priority Data
Apr. 25, 2002  (GB)  .................. 0209482.9
Oct. 28, 2002  (GB)  .................. 0225027.2

(51) Int. Cl.
A61K 31/166   (2006.01)
A61K 31/17    (2006.01)
C07C 233/65   (2006.01)
C07C 62/04    (2006.01)
C07C 275/46   (2006.01)

(52) U.S. Cl. ........................ 514/620; 514/597; 514/651; 514/652; 562/470; 564/51; 564/165; 564/348

(58) Field of Classification Search ............... 564/165; 514/620

See application file for complete search history.

(56) References Cited

U.S. PATENT DOCUMENTS

| | | |
|---|---|---|
| 4,627,432 A | 12/1986 | Newell et al. |
| 4,778,054 A | 10/1988 | Newell et al. |
| 4,811,731 A | 3/1989  | Newell et al. |
| 5,035,237 A | 7/1991  | Newell et al. |
| 5,552,438 A | 9/1996  | Christensen, IV |
| 5,590,645 A | 1/1997  | Davies et al. |
| 5,873,360 A | 2/1999  | Davies et al. |

FOREIGN PATENT DOCUMENTS

| | | |
|---|---|---|
| DE | 3513885 | 10/1985 |
| EP | 0069715 | 1/1983 |
| EP | 0947498 | 10/1999 |
| GB | 2064336 | 6/1981 |
| GB | 2129691 | 5/1984 |
| GB | 2140800 | 12/1984 |
| GB | 2 159 151 A | * 11/1985 |
| GB | 2159151 | 11/1985 |
| GB | 2169265 | 7/1986 |
| GB | 2178965 | 2/1987 |
| GB | 2242134 | 9/1991 |
| JP | 10152460 | 6/1998 |
| WO | WO99/16766 | 4/1999 |
| WO | WO99/47505 | 9/1999 |
| WO | WO 01/13953 | 3/2001 |

OTHER PUBLICATIONS

Ramsay et al, "Polymorphism in the β2-adrenorecptor gene are associated with decreased airway responsiveness," Clinical and Experimental Allergy, 1999 vol. 29, pp. 1195-1203.*
MedlinePlus Drug Information: Salmeterol Oral Inhalation (2007), available at: http://www.nlm.nih.gov/medlineplus/druginfo/medmaster/a695001.html.*
Fuji et al., "Novel phosphodiesterase 4 inhibitor T-440 reverses and prevents human bronchial contraction induced by allergen," *The Journal of Pharmacology and Experimental Theapeutics* 284(1):162-169 (1998).
Landells et al., "Oral administration of the phosphodiesterase (PDE)4 inhibitor, V11294A inhibits ex-vivo agonist-induced cell activation," *Eur Resp J.* 12(Suppl. 28):Abst. P2393 CAS reference No. 162401-32-3 (Sep. 19-23, 1998).

* cited by examiner

*Primary Examiner*—Rebecca Anderson
*Assistant Examiner*—Andrew B. Freistein
(74) *Attorney, Agent, or Firm*—Robert J. Smith

(57) ABSTRACT

The present invention relates to novel compounds of formula (I),

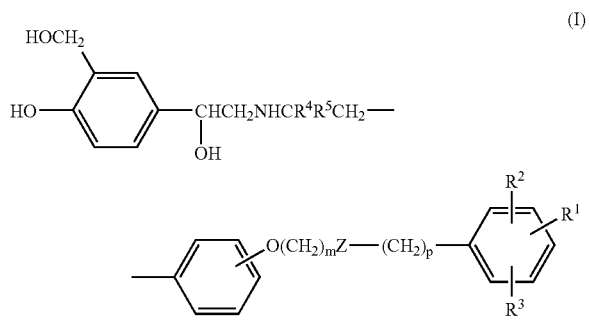

or a salt, solvate, or physiologically functional derivative thereof, to a process for their manufacture, to pharmaceutical compositions containing them, and to their use in therapy, in particular their use in the prophylaxis and treatment of respiratory diseases.

10 Claims, No Drawings

PHENETHANOLAMINE DERIVATIVES

CROSS-REFERENCE TO RELATED APPLICATIONS

This application is filed under 35 U.S.C. § 371 as the United States National Phase Application of International Application No. PCT/EP03/04367 filed Apr. 24, 2003, which claims priority to GB Application Nos. 0209482.9 and 0225027.2 filed Apr. 25, 2002 and Oct. 28, 2002, respectively.

The present invention is concerned with phenethanolamine derivatives, processes for their preparation, compositions containing them and their use in medicine, particularly in the prophylaxis and treatment of respiratory diseases.

Certain phenethanolamine compounds are known in the art as having selective stimulant action at $\beta_2$-adrenoreceptors and therefore having utility in the treatment of bronchial asthma and related disorders. Thus GB 2 140 800 describes phenethanolamine compounds including 4-hydroxy-$\alpha^1$-[[[6-(4-phenylbutoxy)hexyl]amino]methyl]-1,3-benzene-dimethanol 1-hydroxy-2-naphthalenecarboxylate (salmeterol xinafoate) which is now used clinically in the treatment of such medical conditions.

Although salmeterol and the other commercially available $\beta_2$-adrenoreceptor agonists are effective bronchodilators, the maximum duration of action is 12 hours, hence twice daily dosing is often required. There is therefore a clinical need for compounds having potent and selective stimulant action at $\beta_2$-adrenoreceptors and having an advantageous profile of action.

According to the present invention, there is provided a compound of formula (I)

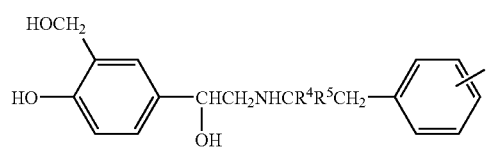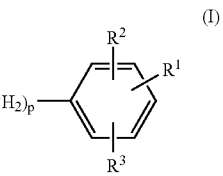 (I)

or a salt, solvate, or physiologically functional derivative thereof, wherein:

m is an integer of from 2 to 4;
p is an integer of from 1 to 4, preferably 1;
Z is O or $CH_2$—
$R^1$ is selected from hydrogen, $C_{1-6}$alkyl, $C_{1-6}$alkoxy, hydroxy, cyano, nitro, halo, $C_{1-6}$haloalkyl, $XCO_2R^8$, —$XC(O)NR^7R^8$, —$XNR^6C(O)R^7$, —$XNR^6C(O)NR^7R^8$, —$XNR^6C(O)NC(O)NR^7R^8$, —$XNR^6SO_2R^7$, —$XSO_2NR^9R^{10}$, —$XNR^6SO_2NR^9R^{10}$, $XSR^6$, $XSOR^6$, $XSO_2R^6$, —$XNR^7R^8$, —$XNR^6C(O)OR^7$,
or $R^1$ is selected from —X-aryl, —X-hetaryl, or —X-(aryloxy), each optionally substituted by 1 or 2 groups independently selected from hydroxy, $C_{1-6}$alkoxy, halo, $C_{1-6}$alkyl, $C_{1-6}$haloalkyl, —$NR^6C(O)R^7$, $SR^6$, $SOR^6$, —$SO_2R^6$, —$SO_2NR^9R^{10}$, —$CO_2R^8$, —$NR^7R^8$, or hetaryl optionally substituted by 1 or 2 groups independently selected from hydroxy, $C_{1-6}$alkoxy, halo, $C_{1-6}$alkyl, or $C_{1-6}$haloalkyl;
X is —$(CH_2)_q$— or $C_{2-6}$ alkenylene;
q is an integer from 0 to 6, preferably 0 to 4;

$R^6$ and $R^7$ are independently selected from hydrogen, $C_{1-6}$alkyl, $C_{3-7}$cycloalkyl, aryl, hetaryl, hetaryl($C_{1-6}$alkyl)- and aryl($C_{1-6}$alkyl)- and $R^6$ and $R^7$ are each independently optionally substituted by 1 or 2 groups independently selected from halo, $C_{1-6}$alkyl, $C_{3-7}$ cycloalkyl, $C_{1-6}$ alkoxy, $C_{1-6}$haloalkyl, —NHC(O)($C_{1-6}$alkyl), —$SO_2(C_{1-6}$alkyl), —$SO_2$(aryl), —$CO_2H$, and —$CO_2(C_{1-4}$alkyl), —$NH_2$, —NH($C_{1-6}$alkyl), aryl($C_{1-6}$-alkyl)-, aryl($C_{2-6}$alkenyl)-, aryl ($C_{2-6}$alkynyl)-, hetaryl($C_{1-6}$alkyl)-, —$NHSO_2$aryl, —NH (hetaryl$C_{1-6}$alkyl), —$NHSO_2$hetaryl, —$NHSO_2(C_{1-6}$alkyl), —NHC(O)aryl, or —NHC(O)hetaryl;
or where $R^1$ is —$XNR^6C(O)OR^7$, $R^6$ and $R^7$ may, together with the —NC(O)O— portion of the group $R^1$ to which they are bonded, form a saturated or unsaturated ring, preferably a 5-, 6-, or 7-membered ring, for example an oxazolidine ring, such as oxazolidine-2,4-dione,
or where $R^1$ is —$XNR^6C(O)NR^7R^8$, $R^6$ and $R^7$ may, together with the —NC(O)N— portion of the group $R^1$ to which they are bonded, form a saturated or unsaturated ring, preferably a 5-, 6-, or 7-membered ring, for example an imidazolidine ring, such as imidazolidine-2,4-dione;
$R^8$ is selected from hydrogen, $C_{1-6}$alkyl and $C_{3-7}$cycloalkyl;
or $R^7$ and $R^8$, together with the nitrogen atom to which they are bonded, form a 5-, 6- or 7-membered nitrogen-containing ring;
$R^9$ and $R^{10}$ are independently selected from hydrogen, $C_{1-6}$alkyl, $C_{3-7}$cycloalkyl, $CO_2(C_{1-4}$alkyl), aryl, hetaryl, hetaryl($C_{1-6}$alkyl)- and aryl($C_{1-6}$alkyl)-, or $R^9$ and $R^{10}$, together with the nitrogen to which they are bonded, form a 5-, 6-, or 7-membered nitrogen containing ring;
and $R^9$ and $R^{10}$ are each optionally substituted by one or two groups independently selected from halo, $C_{1-6}$alkyl, and $C_{3-7}$cycloalkyl, $C_{1-6}$haloalkyl;

$R^2$ is selected from hydrogen, hydroxy, $C_{1-6}$alkyl, $C_{1-6}$alkoxy, halo, aryl, aryl($C_{1-6}$alkyl)-, $C_{1-6}$haloalkoxy, and $C_{1-6}$haloalkyl;
$R^3$ is selected from hydrogen, hydroxy, $C_{1-6}$alkyl, $C_{1-6}$alkoxy, halo, aryl, aryl($C_{1-6}$alkyl)-, $C_{1-6}$haloalkoxy, and $C_{1-6}$haloalkyl; and
$R^4$ and $R^5$ are independently selected from hydrogen and $C_{1-4}$ alkyl with the proviso that the total number of carbon atoms in $R^4$ and $R^5$ is not more than 4.

In the compound of formula (I), the group $R^1$ is preferably attached to the para- or meta-position, and more preferably to the meta-position relative to the -$Z(CH_2)_p$ link.

The groups $R^2$ and $R^3$ are each independently preferably attached to the ortho- or meta-position, more preferably to the ortho position relative to the -$Z(CH_2)_p$-link.

In one preferred embodiment $R^1$ represents a substituent as defined above, other than hydrogen, most preferably attached to the meta-position relative to the -$Z(CH_2)_p$ link, and $R^2$ and $R^3$ each represent hydrogen.

In another preferred embodiment $R^1$ represents hydrogen and $R^2$ and $R^3$ each represent a substituent as defined above, at least one of which is other than hydrogen, and $R^2$ and $R^3$ are each independently attached to the ortho- or meta-positions relative to the -Z(CH$_2$)$_p$ link. In a particular embodiment, when R$^2$ and R$^3$ each represent halogen they are preferably attached at the ortho positions.

In a particular embodiment of this invention R$^1$ is suitably selected from hydrogen, C$_{1-6}$alkyl, hydroxy, cyano, nitro, halo, C$_{1-6}$haloalkyl, XCO$_2$R$^8$, —XC(O)NR$^7$R$^8$, —XNR$^6$C(O)R$^7$, —XNR$^6$C(O)NR$^7$R$^8$, —XNR$^6$C(O)NC(O)NR$^7$R$^8$, —XNR$^6$SO$_2$R$^7$, —XSO$_2$NR$^9$R$^{10}$, —XSR6, —XSOR$^6$, —XSO$_2$R$^6$, —XNR$^7$R$^8$, —XNR$^6$C(O)OR$^7$, or R$^1$ is selected from —X-aryl, —X-hetaryl, or —X-(aryloxy), each optionally substituted by 1 or 2 groups independently selected from hydroxy, C$_{1-6}$alkoxy, halo, C$_{1-6}$alkyl, C$_{1-6}$haloalkyl, —NR$^6$C(O)R$^7$, SR$^6$, SOR$^6$, —SO$_2$R$^6$, —SO$_2$NR$^9$R$^{10}$, —CO$_2$R$^8$, —NR$^7$R$^8$, or hetaryl optionally substituted by 1 or 2 groups independently selected from hydroxy, C$_{1-6}$alkoxy, halo, C$_{1-6}$alkyl, or C$_{1-6}$haloalkyl;

wherein R$^6$, R$^7$, R$^8$, R$^9$ and R$^{10}$ are as defined above, provided that in this instance neither R$^9$ nor R$^{10}$ represents —CO$_2$(C$_{1-4}$alkyl).

In the compounds of formula (I), the group R$^1$ is suitably selected from hydrogen, C$_{1-6}$alkyl, C$_{1-6}$alkoxy, hydroxy, cyano, halo, XCO$_2$R$^8$, —XC(O)NR$^7$R$^8$, —XNR$^6$C(O)R$^7$, —XNR$^6$C(O)NR$^7$R$^8$, —XNR$^6$C(O)NC(O)NR$^7$R$^8$, —XNR$^6$SO$_2$R$^7$, —XSO$_2$NR$^9$R$^{10}$, —XNR$^6$SO$_2$NR$^9$R$^{10}$, XSOR$^6$, and —XSO$_2$R$^6$, or R$^1$ is selected from —X-aryl, optionally substituted by 1 or 2 groups independently selected from hydroxy, C$_{1-6}$alkoxy, halo, C$_{1-6}$alkyl, C$_{1-6}$haloalkyl, —NR$^6$C(O)R$^7$, SR$^6$, SOR$^6$, —SO$_2$R$^6$, —SO$_2$NR$^9$R$^{10}$, —CO$_2$R$^8$, —NR$^7$R$^8$, preferably —CO$_2$R$^8$, wherein R$^6$, R$^7$, R$^8$, R$^9$ and R$^{10}$ are as defined above.

In a further embodiment the group R$^1$ is suitably selected from hydrogen, C$_{1-4}$alkyl, hydroxy, halo, —NR$^6$C(O)NR$^7$R$^8$, and —NR$^6$SO$_2$R$^7$ wherein R$^6$ and R$^7$ are as defined above or more suitably wherein R$^6$ is hydrogen and R$^7$ is selected from hydrogen, C$_{1-6}$alkyl, C$_{3-6}$cycloalkyl, and aryl and is optionally substituted as described above.

In another embodiment, the group R$^1$ is preferably selected from hydroxy, —XC(O)NR$^7$R$^8$, and —XSO$_2$NR$^9$R$^{10}$. Most preferably R$^1$ represents a group —XC(O)NR$^7$R$^8$. In this embodiment X preferably represents —(CH$_2$)$_q$— where q is zero.

Where R$^1$ is —XNR$^6$C(O)NR$^7$R$^8$, R$^6$ and R$^7$ may, together with the —NC(O)N— portion of the group R$^1$ to which they are bonded, form a saturated or unsaturated ring, preferably a 5-, 6-, or 7-membered ring, for example an imidazolidine ring, such as imidazolidine-2,4-dione.

Where R$^1$ is —XNR$^6$C(O)OR$^7$, R$^6$ and R$^7$ may, together with the —NC(O)O— portion of the group R$^1$ to which they are bonded, form a saturated or unsaturated ring, preferably a 5-, 6-, or 7-membered ring, for example an oxazolidine ring, such as oxazolidine-2,4-dione.

Where R$^1$ is —XC(O)NR$^7$R$^8$ or —XNR$^6$C(O)NR$^7$R$^8$, R$^7$ and R$^8$ may, together with the nitrogen to which they are bonded, form a 5-, 6-, or 7-membered nitrogen containing ring.

R$^6$ and R$^7$ are suitably selected from hydrogen, C$_{1-6}$alkyl, C$_{3-7}$cycloalkyl, aryl, and hetaryl, independently optionally substituted by 1 or 2 groups independently selected from CO$_2$H, —NH$_2$, and —NH(C$_{1-6}$alkyl).

In the compounds of formula (I) wherein the group R$^1$ is substituted by R$^6$ and/or R$^8$, R$^6$ and/or R$^8$ are suitably hydrogen.

In a particular embodiment, R$^9$ and R$^{10}$ are independently selected from hydrogen, C$_{1-6}$alkyl, C$_{3-7}$cycloalkyl, aryl, hetaryl, hetaryl(C$_{1-6}$alkyl)- and aryl(C$_{1-6}$alkyl)-, or R$^9$ and R$^{10}$, together with the nitrogen to which they are bonded, form a 5-, 6-, or 7-membered nitrogen containing ring;

and R$^9$ and R$^{10}$ are each optionally substituted by one or two groups independently selected from halo, C$_{1-6}$alkyl, and C$_{3-7}$cycloalkyl, C$_{1-6}$haloalkyl;

In a further embodiment, R$^9$ and R$^{10}$ are suitably independently selected from hydrogen, C$_{1-6}$alkyl, —CO$_2$(C$_{1-4}$) alkyl and C$_{3-7}$cycloalkyl.

In the compounds of formula (I), R$^4$ and R$^5$ are preferably independently selected from hydrogen and methyl, more preferably R$^4$ and R$^5$ are both hydrogen.

In the compounds of formula (I) R$^2$ and R$^3$ preferably each independently represent hydrogen or halogen Preferably the moiety

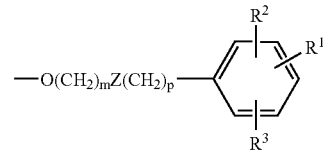

is attached to the para position of the 'central' phenyl ring, relative to the —NHCR$^4$R$^5$CH$_2$— moiety.

As used herein, the term "hetaryl" means a 5- to 10-membered heteroaromatic ring or bicyclic ring system which includes 1, 2, or 3 heteroatoms independently selected from oxygen, nitrogen and sulphur, such as thienyl, pyridyl, 2,4-dihydroxypyrimidinyl, 2,3-dihydroimidazo[2,1-b][1,3]thiazol-6-yl, or bipyridyl, preferably a 5- or 6-membered heteroaromatic ring.

As used herein, the term "aryl" either alone or in the term "aryloxy" means a monocyclic or bicyclic aromatic ring system, such as phenyl, naphthyl, or biphenyl. Preferably the term "aryl" means phenyl.

The term 'alkyl' as used herein, either as such or as part of another group, such as 'alkoxy' encompasses both straight and branched chains.

It is to be understood that the present invention covers all combinations of particular and preferred groups described hereinabove.

The compounds of formula (I) include an asymmetric centre, namely the carbon atom of the

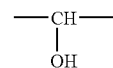

group. The present invention includes both (S) and (R) enantiomers either in substantially pure form or admixed in any proportions. Preferably, the compounds of the invention are in the form of the (R) enantiomers.

Similarly, where R$^4$ and R$^5$ are different groups, the carbon atom to which they are attached is an asymmetric centre and the present invention includes both (S) and (R) enantiomers at this centre either in substantially pure form or admixed in any proportions.

Thus the compounds of formula (I) include all enantiomers and diastereoisomers as well as mixtures thereof in any proportions.

Preferred compounds of the invention include:

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}urea;

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}dicarbonimidic diamide;

4-((1R)-2-{[2-(4-{2-[(3-Fluorobenzyl)oxy]ethoxy}phenyl)ethyl]amino}-1-hydroxyethyl)-2-(hydroxymethyl)phenol;

2-(Hydroxymethyl)-4-((1R)-1-hydroxy-2-{[2-(4-{2-[(3-methylbenzyl)oxy]ethoxy}phenyl)ethyl]amino}ethyl)phenol;

4-((1R)-2-{[2-(4-{2-[(3-Chlorobenzyl)oxy]ethoxy}phenyl)ethyl]amino}-1-hydroxyethyl)-2-(hydroxymethyl)phenol;

4-((1R)-1-Hydroxy-2-{[2-(4-{2-[(3-iodobenzyl)oxy]ethoxy}phenyl)ethyl]amino}ethyl)-2-(hydroxymethyl)phenol;

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}acetamide;

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}nicotinamide;

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}-2-furamide;

3-[(2-{4-[2-({(2R)-2-Hydroxy-2-[4-hydroxy-3-(hydroxymethyl)phenyl]ethyl}amino)ethyl]phenoxy}ethoxy)methyl]benzamide;

3-[(2-{4-[2-({(2R)-2-Hydroxy-2-[4-hydroxy-3-(hydroxymethyl)phenyl]ethyl}amino)ethyl]phenoxy}ethoxy)methyl]benzonitrile;

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}methanesulfonamide;

4-{(1R)-2-[(2-{4-[2-)Benzyloxy]ethoxy]phenyl}ethyl]amino]-1-hydroxyethyl}-2-(hydroxymethyl)phenol;

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}-N-phenylurea;

4-((1R)-1-Hydroxy-2-{[2-(4-{2-[(3-hydroxybenzyl)oxy]ethoxy}phenyl)ethyl]amino}ethyl)-2-(hydroxymethyl)phenol;

4-{(1R)-2-[((1S)-2-{4-[2-(Benzyloxy)ethoxy]phenyl}-1-methylethyl)amino]-1-hydroxyethyl}-2-(hydroxymethyl)phenol;

4-{(1R)-2-[((1R)-2-{4-[2-(Benzyloxy)ethoxy]phenyl}-1-methylethyl)amino]-1-hydroxyethyl}-2-(hydroxymethyl)phenol;

3-[(2-{4-[2-({(2R)-2-Hydroxy-2-[4-hydroxy-3-(hydroxymethyl)phenyl]ethyl}amino)ethyl]phenoxy}ethoxy)methyl]benzenesulfonamide;

3-[(2-{4-[2-({(2R)-2-Hydroxy-2-[4-hydroxy-3-(hydroxymethyl)phenyl]ethyl}amino)ethyl]phenoxy}ethoxy)methyl]-N-isopropylbenzenesulfonamide;

3-[(2-{4-[2-(}(2R)-2-Hydroxy-2-[4-hydroxy-3-(hydroxymethyl)phenyl]ethyl}amino)ethyl]phenoxy}ethoxy)methyl]benzoic acid;

4-((1R)-2-{[2-(4-{2-[(4-Fluorobenzyl)oxy]ethoxy}phenyl)ethyl]amino}-1-hydroxyethyl)-2-(hydroxymethyl)phenol;

4-((1R)-2-{[2-(4-{2-[(2,6-Dichlorobenzyl)oxy]ethoxy}phenyl)ethyl]amino}-1-hydroxyethyl)-2-(hydroxymethyl)phenol;

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}sulfamide, N-(tert-butoxycarbonyl)-N-{3-[(2-{4-[2-({(2R)-2-hydroxy-2-[4-hydroxy-3-(hydroxymethyl)phenyl]ethyl}amino)ethyl]phenoxy}ethoxy)methyl]phenyl}sulfamide;

4-[(1R)-2-({2-[4-(2-{[3-(Cyclopentylsulfonyl)benzyl]oxy}ethoxy)phenyl]ethyl}amino)-1-hydroxyethyl]-2-(hydroxymethyl)phenol;

4-[(1R)-2-({2-[4-(2-{[3-(Cyclopentylsulfinyl)benzyl]oxy}ethoxy)phenyl]ethyl}amino)-1-hydroxyethyl]-2-(hydroxymethyl)phenol;

4-((1R)-1-Hydroxy-2-{[2-(4-{2-[(4-isopropoxybenzyl)oxy]ethoxy}phenyl)ethyl]amino}ethyl)-2-(hydroxymethyl)phenol;

4-((1R)-1-Hydroxy-2-}[2-(4-{2-[(4-hydroxybenzyl)oxy]ethoxy}phenyl)ethyl]amino}ethyl)-2-(hydroxymethyl)phenol;

3-[(2-{4-[2-({(2R)-2-Hydroxy-2-[4-hydroxy-3-(hydroxymethyl)phenyl]ethyl}amino)ethyl]phenoxy}ethoxy)methyl]-N-isopropylbenzamide;

N-Cyclohexyl-3-[(2-{4-[2-({(2R)-2-hydroxy-2-[4-hydroxy-3-(hydroxymethyl)phenyl]ethyl}amino)ethyl]phenoxy}ethoxy)methyl]benzamide;

N-Cyclohexyl-3-[(2-{4-[2-({(2R)-2-hydroxy-2-[4-hydroxy-3-(hydroxymethyl)phenyl]ethyl}amino)ethyl]phenoxy}ethoxy)methyl]benzenesulfonamide;

3-[(2-{4-[2-({(2R)-2-Hydroxy-2-[4-hydroxy-3-(hydroxymethyl)phenyl]ethyl}amino) ethyl]phenoxy}ethoxy)methyl]-N-methylbenzenesulfonamide;

4-[(1R)-1-Hydroxy-2-({2-[4-(2-{[3-(isopropylsulfinyl)benzyl]oxy}ethoxy)phenyl]ethyl}amino)ethyl]-2-(hydroxymethyl)phenol;

4-[(1R)-1-Hydroxy-2-({2-[4-(2-{[3-(isopropylsulfinyl)benzyl]oxy}ethoxy)phenyl]ethyl}amino)ethyl]-2-(hydroxymethyl)phenol;

2-(Hydroxymethyl)-4-[(1R)-1-hydroxy-2-({2-[4-(4phenylbutoxy)phenyl]ethyl}amino)ethyl]phenol;

4-{(1R)-1-Hydroxy-2-[(2-{4-[4-(3-hydroxyphenyl)butoxy]phenyl}ethyl)amino]ethyl}-2-(hydroxymethyl)phenol;

4-((1R)-2-{[2-(4-{4-[3-(Cyclopentylsulfinyl)phenyl]butoxy}phenyl)ethyl]amino}-1-hydroxyethyl)-2-(hydroxymethyl)phenol;

4-{(1R)-2-[(2-{4-[4-(2,6-Dichlorophenyl)butoxy]phenyl}ethyl)amino]-1-hydroxyethyl}-2-(hydroxymethyl)phenol;

3-(4-{4-[2-({(2R)-2-Hydroxy-2-[4-hydroxy-3-(hydroxymethyl)phenyl]ethyl}amino)ethyl]phenoxy}butyl)benzenesulfonamide N-[3-(4-{4-[2-({(2R)-2-Hydroxy-2-[4-hydroxy-3-(hydroxymethyl)phenyl]ethyl}amino)ethyl]phenoxy}butyl)phenyl]urea;

3-(4-{4-[2-({(2R)-2-Hydroxy-2-[4-hydroxy-3-(hydroxymethyl)phenyl]ethyl}amino)ethyl]phenoxy}butyl)benzoic acid;

3-(4-{4-[2-({(2R)-2-Hydroxy-2-[4-hydroxy-3-(hydroxymethyl)phenyl]ethyl}amino)ethyl]phenoxy}butyl)benzonitrile;

3-(4-{4-[2-({(2R)-2-Hydroxy-2-[4-hydroxy-3-(hydroxymethyl)phenyl]ethyl}amino)ethyl]phenoxy}butyl)benzamide;

3'-[(2-{4-[2-({(2R)-2-Hydroxy-2-[4-hydroxy-3-(hydroxymethyl)phenyl]ethyl}amino)ethyl]phenoxy}ethoxy)methyl]-1,1'-biphenyl-3-carboxylic acid;

N-Butyl-3-[(2-{4-[2-({(2R)-2-hydroxy-2-[4-hydroxy-3-(hydroxymethyl)phenyl]ethyl}amino)ethyl]phenoxy}ethoxy)methyl]benzamide;

3-[(2-{4-[2-({(2R)-2-Hydroxy-2-[4-hydroxy-3-(hydroxymethyl)phenyl]ethyl}amino)ethyl]phenoxy}ethoxy)methyl]-N-pentylbenzamide;

3-[(2-{4-[2-({(2R)-2-Hydroxy-2-[4-hydroxy-3-(hydroxymethyl)phenyl]ethyl}amino)ethyl]phenoxy}ethoxy)methyl]-N-isobutylbenzamide;

3-[(2-{4-[2-({(2R)-2-Hydroxy-2-[4-hydroxy-3-(hydroxymethyl)phenyl]ethyl}amino)ethyl]phenoxy}ethoxy)methyl]-N-isopentylbenzamide;

and salts, solvates, and physiologically functional derivatives thereof.

Particularly preferred compounds of the invention include:

3-[(2-{4-[2-({(2R)-2-Hydroxy-2-[4-hydroxy-3-(hydroxymethyl)phenyl]ethyl}amino)ethyl]phenoxy}ethoxy)methyl]benzamide;

N-Cyclohexyl-3-[(2-{4-[2-({(2R)-2-hydroxy-2-[4-hydroxy-3-(hydroxymethyl)phenyl]ethyl]amino)ethyl]phenoxy}ethoxy)methyl]benzamide;

3-(4-{4-[2-({(2R)-2-Hydroxy-2-[4-hydroxy-3-(hydroxymethyl)phenyl]ethyl}amino)ethyl]phenoxy}butyl)benzenesulfonamide;

3-(4-{4-[2-({(2R)-2-Hydroxy-2-[4-hydroxy-3-(hydroxymethyl)phenyl]ethyl}amino)ethyl]phenoxy}butyl)benzamide;

N-Butyl-3-[(2-[4-[2-({(2R)-2-hydroxy-2-[4-hydroxy-3-(hydroxymethyl)phenyl]ethyl}amino)ethyl]phenoxy}ethoxy)methyl]benzamide;

3-[(2-{4-[2-({(2R)-2-Hydroxy-2-[4-hydroxy-3-(hydroxymethyl)phenyl]ethyl}amino)ethyl]phenoxy}ethoxy)methyl]-N-pentylbenzamide;

3-[(2-{4-[2-({(2R)-2-Hydroxy-2-[4-hydroxy-3-(hydroxymethyl)phenyl]ethyl}amino)ethyl]phenoxy}ethoxy)methyl]-N-isobutylbenzamide; and 3-[(2-[4-[2-({(2R)-2-Hydroxy-2-[4-hydroxy-3-(hydroxymethyl)phenyl]ethyl]amino)ethyl]phenoxy}ethoxy)methyl]-N-isopentylbenzamide;

and salts, solvates, and physiologically functional derivatives thereof.

Salts and solvates of compounds of formula (I) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of formula (I) and their pharmaceutically acceptable salts, solvates, and physiologically functional derivatives.

By the term "physiologically functional derivative" is meant a chemical derivative of a compound of formula (I) having the same physiological function as the free compound of formula (I), for example, by being convertible in the body thereto. According to the present invention, examples of physiologically functional derivatives include esters.

Suitable salts according to the invention include those formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, triphenylacetic, sulphamic, sulphanilic, succinic, oxalic, fumaric, maleic, malic, glutamic, aspartic, oxaloacetic, methanesulphonic, ethanesulphonic, arylsulphonic (for example p-toluenesulphonic, benzenesulphonic, naphthalenesulphonic or naphthalenedisulphonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic) and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Pharmaceutically acceptable esters of the compounds of formula (I) may have a hydroxyl group converted to a $C_{1-6}$ alkyl, aryl, aryl $C_{1-6}$ alkyl, or amino acid ester.

As mentioned above, the compounds of formulae (I) are selective $\beta_2$-adrenoreceptor agonists as demonstrated using functional or reporter gene readout from cell lines transfected with human beta-adrenoreceptors as described below. Compounds according to the present invention also have the potential to combine long duration of effect with rapid onset of action. Furthermore, certain compounds have shown an improved therapeutic index in animal models relative to existing long-acting $\beta_2$-agonist bronchodilators. As such, compounds of the invention may be suitable for once-daily administration.

Therefore, compounds of formula (I) and their pharmaceutically acceptable salts, solvates, and physiologically functional derivatives have use in the prophylaxis and treatment of clinical conditions for which a selective $\beta_2$-adrenoreceptor agonist is indicated. Such conditions include diseases associated with reversible airways obstruction such as asthma, chronic obstructive pulmonary diseases (COPD) (e.g. chronic and wheezy bronchitis, emphysema), respiratory tract infection and upper respiratory tract disease.

Other conditions which may be treated include premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

Accordingly, the present invention provides a method for the prophylaxis or treatment of a clinical condition in a mammal, such as a human, for which a selective $\beta_2$-adrenoreceptor agonist is indicated, which comprises administration of a therapeutically effective amount of a compound of formula (I), or a pharmaceutically acceptable salt, solvate, or physiologically functional derivative thereof. In particular, the present invention provides such a method for the prophylaxis or treatment of a disease associated with reversible airways obstruction such as asthma, chronic obstructive pulmonary disease (COPD), respiratory tract infection or upper respiratory tract disease. In a further aspect the present invention provides such a method for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

In the alternative, there is also provided a compound of formula (I), or a pharmaceutically acceptable salt, solvate, or physiologically functional derivative thereof for use in medical therapy, particularly, for use in the prophylaxis or treatment of a clinical condition in a mammal, such as a human, for which a selective $\beta_2$-adrenoreceptor agonist is indicated. In particular, there is provided a compound of formula (I), or a pharmaceutically acceptable salt, solvate, or physiologically functional derivative thereof for the prophylaxis or treatment of a disease associated with reversible airways obstruction such as asthma, chronic obstructive pulmonary disease (COPD), respiratory tract infection or upper respiratory tract disease. In a further aspect, there is provided a compound of formula (I), or a pharmaceutically acceptable salt, solvate, or physiologically functional derivative thereof for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

The present invention also provides the use of a compound of formula (I), or a pharmaceutically acceptable salt, solvate, or physiologically functional derivative thereof in the manufacture of a medicament for the prophylaxis or treatment of a clinical condition for which a selective $\beta_2$-adrenoreceptor agonist is indicated, for example a disease associated with reversible airways obstruction such as asthma, chronic obstructive pulmonary disease (COPD), respiratory tract infection or upper respiratory tract disease. In a further aspect, there is provided a compound of formula (I), or a pharmaceutically acceptable salt, solvate, or physiologically functional derivative thereof in the manufacture of a medicament for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

The amount of a compound of formula (I), or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The compounds of the invention may be administered by inhalation at a dose of from 0.0005 mg to 10 mg, preferably 0.005 mg to 0.5 mg. The dose range for adult humans is generally from 0.0005 mg to 100 mg per day and preferably 0.01 mg to 1 mg per day.

While it is possible for the compound of formula (I), or a pharmaceutically acceptable salt, solvate, or physiologically functional derivative thereof to be administered alone, it is preferable to present it as a pharmaceutical formulation.

Accordingly, the present invention further provides a pharmaceutical formulation comprising a compound of formula (I), or a pharmaceutically acceptable salt, solvate, or physiologically functional derivative thereof, and a pharmaceutically acceptable carrier or excipient, and optionally one or more other therapeutic ingredients.

Hereinafter, the term "active ingredient" means a compound of formula (I), or a pharmaceutically acceptable salt, solvate, or physiologically functional derivative thereof.

The formulations include those suitable for oral, parenteral (including subcutaneous, intradermal, intramuscular, intravenous and intraarticular), inhalation (including fine particle dusts or mists which may be generated by means of various types of metered dose pressurised aerosols, nebulisers or insufflators), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described.

Dry powder compositions for topical delivery to the lung by inhalation may, for example, be presented in capsules and cartridges of for example gelatine, or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 20 µg-10 mg of the compound of formula (I) optionally in combination with another therapeutically active ingredient. Alternatively, the compound of the invention may be presented without excipients.

Packaging of the formulation may be suitable for unit dose or multi-dose delivery. In the case of multi-dose delivery, the formulation can be pre-metered (eg as in Diskus, see GB 2242134, U.S. Pat. No. 5,590,645 and U.S. Pat. No. 5,873,360; or Diskhaler, see GB 2178965, 2129691 and 2169265, and U.S. Pat. No. 4,627,432, U.S. Pat. No. 4,778,054, U.S. Pat. No. 4,811,731 and US50352377) or metered in use (eg as in Turbuhaler, see EP 69715). The content of U.S. Pat. No. 5,590,645, U.S. Pat. No. 5,873,360 U.S. Pat. No. 4,627,432, U.S. Pat. No. 4,778,054, U.S. Pat. No. 4,811,731 and US50352377 is incorporated herein by reference. An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Spray compositions for topical delivery to the lung by inhalation may for example be formulated as aqueous solutions or suspensions or as aerosols delivered from pressurised packs, such as a metered dose inhaler, with the use of a suitable liquefied propellant. A metered dose inhaler is generally shown and described in European patent No. 1066073, the content of which is hereby incorporated herein by reference.

Aerosol compositions suitable for inhalation can be either a suspension or a solution and generally contain the compound of formula (I) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetrafluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants eg oleic acid or lecithin and cosolvents eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline. When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 μm and not less than 15% will have a MMD of less than 15 μm.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose an acacia.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds and pharmaceutical formulations according to the invention may be used in combination with or include one or more other therapeutic agents, for example selected from anti-inflammatory agents, anticholinergic agents (particularly an $M_1$, $M_2$, $M_1/M_2$ or $M_3$ receptor antagonist), other $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent (for example a corticosteroid or an NSAID), an anticholinergic agent, another $\beta_2$-adrenoreceptor agonist, an antiinfective agent (e.g. an antibiotic or an antiviral), or an antihistamine. Preferred are combinations comprising a compound of formula (I) or a pharmaceutically acceptable salt, solvate or physiologically functional derivative thereof together with a corticosteroid, and/or an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-dfluoro-11β-hydroxy-16α- methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2α agonists), cytokine antagonists (e.g. chemokine antagonists) or inhibitors of cytokine synthesis. Suitable other $β_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Of particular interest is use of the compound of formula (I) in combination with a phosphodiesterase 4 (PDE4) inhibitor or a mixed PDE3/PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

A method for determining $IC_{50}$s ratios is set out in U.S. Pat. No. 5,998,428 which is incorporated herein in full by reference as though set out herein. See also PCT application WO 00/51599 for an another description of said assay.

The preferred PDE4 inhibitors of use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity.

A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 μM[$^3$H]-cAMP as the substrate.

Examples of useful PDE4 inhibitors are:
(R)-(+)-1-(4-bromobenzyl)-4-[(3-cyclopentyloxy)-4-methoxyphenyl]-2-pyrrolidone;
(R)-(+)-1-(4-bromobenzyl)-4-[(3-cyclopentyloxy)-4-methoxyphenyl]-2-pyrrolidone;
3-(cyclopentyloxy-4-methoxyphenyl)-1-(4-N'-[N2-cyano-S-methyl-isothioureido]benzyl)-2-pyrrolidone;
cis 4-cyano-4-(3-cyclopentyloxy-4-methoxyphenyl)cyclohexan-1-carboxylic acid];
cis-[4-cyano-4-(3-cyclopropylmethoxy-4-difluoromethoxyphenyl)cyclohexan-1-ol];
(R)-(+)-ethyl [4-(3-cyclopentyloxy-4-methoxyphenyl)pyrrolidine-2-ylidene]acetate; and
(S)-(−)-ethyl [4-(3-cyclopentyloxy-4-methoxyphenyl)pyrrolidine-2-ylidene]acetate.

Most preferred are those PDE4 inhibitors which have an $IC_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]; these are examples of compounds which bind preferentially to the low affinity binding site and which have an $IC_{50}$ ratio of 0.1 or greater.

Other compounds of interest include:
Compounds set out in U.S. Pat. No. 5,552,438 issued 3 Sep. 1996; this patent and the compounds it discloses are incorporated herein in full by reference. The compound of particular interest, which is disclosed in U.S. Pat. No. 5,552,438, is cis4-cyano-4-[3-(cyclopentyloxy)-4-methoxyphenyl]cyclohexane-1-carboxylic acid (also known as cilomalast) and its salts, esters, pro-drugs or physical forms;

AWD-12-281 from elbion (Hofgen, N. et al. 15th EFMC Int Symp Med Chem (Sep. 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (Sep. 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methyl-benzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther,1998, 284(1): 162), and T2585.

Other possible PDE-4 and mixed PDE3/PDE4 inhibitors include those listed in WO01/13953, the disclosure of which is hereby incorporated by reference.

Suitable anticholinergic agents are those compounds that act as antagonists at the muscarinic receptor, in particular those compounds which are antagonists of the $M_1$ and $M_2$ receptors. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-51-48-1 (anhydrous form), atropine sulfate—CAS-5908-99-6; atropine oxide—CAS-4438-22-6 or its HCl salt—CAS-4574-60-1 and methylatropine nitrate—CAS-52-88-0.

Homatropine—CAS-87-00-3, hydrobromide salt—CAS-51-56-9, methylbromide salt—CAS-80-49-9.

Hyoscyamine (d, l)—CAS-101-31-5, hydrobromide salt—CAS-306-03-6 and sulfate salt—CAS-683516-1.

Scopolamine—CAS-51-34-3, hydrobromide salt—CAS-6533-68-2, methylbromide salt—CAS-155-41-9.

Preferred anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, have a core structure, which can be represented by the following formula:

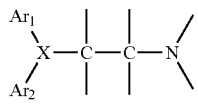

This generalized structure represents three types of antihistamines generally available: ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlropheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

Examples of preferred anti-histamines include methapyrilene and loratadine.

The invention thus provides, in a further aspect, a combination comprising a compound of formula (I) a pharmaceutically acceptable salt, solvate or physiologically functional derivative thereof together with a PDE4 inhibitor.

The invention thus provides, in a further aspect, a combination comprising a compound of formula (I) a pharmaceutically acceptable salt, solvate or physiologically functional derivative thereof together with a corticosteroid.

The invention thus provides, in a further aspect, a combination comprising a compound of formula (I) a pharmaceutically acceptable salt, solvate or physiologically functional derivative thereof together with an anticholinergic.

The invention thus provides, in a further aspect, a combination comprising a compound of formula (I) a pharmaceutically acceptable salt, solvate or physiologically functional derivative thereof together with an antihistamine.

The invention thus provides, in a further aspect, a combination comprising a compound of formula (I) a pharmaceutically acceptable salt, solvate or physiologically functional derivative thereof together with a PDE4 inhibitor and a corticosteroid.

The invention thus provides, in a further aspect, a combination comprising a compound of formula (I) a pharmaceutically acceptable salt, solvate or physiologically functional derivative thereof together with an anticholinergic and a PDE-4 inhibitor.

The combinations referred to above may conveniently be presented for use in the form of a pharmaceutical formulation and thus pharmaceutical formulations comprising a combination as defined above together with a physiologically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

According to a further aspect of the invention, there is provided a process for preparing a compound of formula (I), or a salt, solvate, or physiologically functional derivative thereof which comprises a process (a), (b), (c) or (d) as defined below followed by the following steps in any order:

(i) optional removal of any protecting groups;

(ii) optional separation of an enantiomer from a mixture of enantiomers;

(iii) optional conversion of the product to a corresponding salt, solvate, (iv) optional conversion of a group $R^1$, $R^2$ and/or $R^3$ to another group $R^1$, $R^2$ and/or $R^3$, or physiologically functional derivative thereof.

In the following description of synthetic routes, $R^1$, $R^2$, $R^3$, $R^4$, $R^5$, Z, m and p are as defined for formula (I) and $R^{11}$, $R^{12}$, $R^{13}$ and $R^{14}$ are as defined for formula (II) below unless indicated otherwise.

In one general process (a), a compound of formula (I), may be obtained by deprotection of a protected intermediate, for example of formula (II):

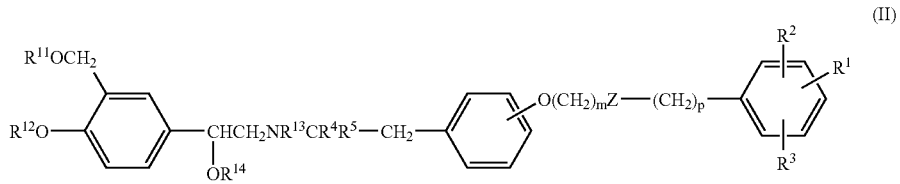

or a salt or solvate thereof, wherein $R^1$, $R^2$, $R^3$, $R^4$, $R^5$, Z, m, and p are as defined for the compounds of formula (I), and $R^{11}$, $R^{12}$, $R^{13}$ and $R^{14}$ are each independently either hydrogen or a protecting group provided that at least one of $R^{11}$, $R^{12}$, $R^{13}$ and $R^{14}$ is a protecting group.

Suitable protecting groups may be any conventional protecting group such as those described in "Protective Groups in Organic Synthesis" by Theodora W Greene and Peter G M Wuts, 3rd edition (John Wiley & Sons, 1999). Examples of suitable hydroxyl protecting groups represented by $R^{11}$ and $R^{12}$ are esters such as acetate ester, aralkyl groups such as benzyl, diphenylmethyl, or triphenylmethyl, and tetrahydropyranyl. Examples of suitable amino protecting groups represented by $R^{13}$ include benzyl, α-methylbenzyl, diphenylmethyl, triphenylmethyl, benzyloxycarbonyl, tert-butoxycarbonyl, and acyl groups such as trichloroacetyl or trifluoroacetyl.

As will be appreciated by the person skilled in the art, use of such protecting groups may include orthogonal protection of groups in the compounds of formula (II) to facilitate the selective removal of one group in the presence of another, thus enabling selective functionalisation of a single amino or hydroxyl function. For example, the —CH(OH) group may be orthogonally protected as —CH(OR$^{14}$) using, for example, a trialkylsilyl group such as triethylsilyl. A person skilled in the art will also appreciate other orthogonal protection strategies, available by conventional means as described in Theodora W Greene and Peter G M Wuts (see above).

The deprotection to yield a compound of formula (I), may be effected using conventional techniques. Thus, for example, when $R^{11}$, $R^{12}$, and/or $R^{13}$ is an aralkyl group, this may be cleaved by hydrogenolysis in the presence of a metal catalyst (e.g. palladium on charcoal).

When $R^{11}$ and/or $R^{12}$ is tetrahydropyranyl this may be cleaved by hydrolysis under acidic conditions. Acyl groups represented by $R^{13}$ may be removed by hydrolysis, for example with a base such as sodium hydroxide, or a group such as trichloroethoxycarbonyl may be removed by reduction with, for example, zinc and acetic acid. Other deprotection methods may be found in Theodora W Greene and Peter G M Wuts (see above). In a particular embodiment of process (a), $R^{11}$ and $R^{12}$ may together represent a protecting group as in the compound of formula (III):

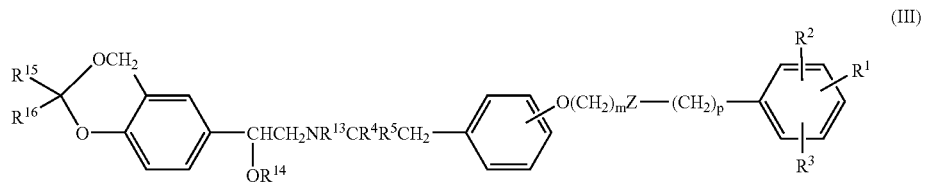

or a salt or solvate thereof, wherein $R^1$, $R^2$, $R^3$, $R^4$, $R^5$, $R^{13}$, $R^{14}$, Z, m, and p are as defined for the compound of formula (II), and $R^{15}$ and $R^{16}$ are independently selected from hydrogen, $C_{1-6}$alkyl, or aryl or $R^{15}$ and $R^{16}$ together form a carbocyclic ring eg. containg from 5 to 7 carbon atoms. In a preferred aspect, both $R^{15}$ and $R^{16}$ are methyl.

The compound of formula (III) may be converted to a compound of formula (I), by hydrolysis with dilute aqueous acid, for example acetic acid or hydrochloric acid in a suitable solvent or by transketalisation in an alcohol, for example ethanol, in the presence of a catalyst such as an acid (for example, toluenesulphonic acid) or a salt (such as pyridinium tosylate) or a resin-bound sulphonic acid such as SCX-2, at normal or elevated temperature.

It will be appreciated that the protecting groups $R^{11}$, $R^{12}$, $R^{13}$ and $R^{14}$ (including the cyclised protecting group formed by $R^{15}$ and $R^{16}$ as depicted in formula (III) may be removed in a single step or sequentially. The precise order in which protecting groups are removed will in part depend upon the nature of said groups and will be readily apparent to the skilled worker. Preferably, when $R^{15}$ and $R^{16}$ together form a protecting group as in formula (III) this protecting group is removed together with any protecting group on the CH(OH) moiety, followed by removal of $R^{13}$. However, preferably the nitrogen protecting group is removed first if deprotection is to be effected using base catalysis.

Compounds of formulae (II) and (III) wherein $R^{13}$ is hydrogen may be prepared from the corresponding compound of formula (IV):

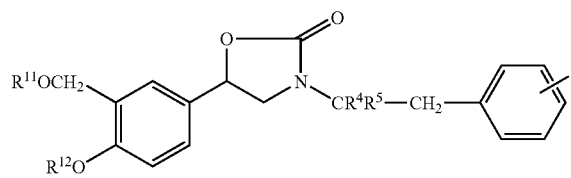

(IV)

or a salt or solvate thereof, wherein $R^1$, $R^2$, $R^3$, $R^4$, $R^5$, $R^{11}$, $R^{12}$, Z, m, and p are as defined for the compound of formula (II) or (III).

The conversion of a compound of formula (IV) to a compound of formula (II) or (III) may be effected by treatment with a base, for example a non-aqueous base, such as potassium trimethylsilanolate, or an aqueous base such as aqueous sodium hydroxide, in a suitable solvent such as tetrahydrofuran.

The compounds of formula (IV) may be prepared by reacting a compound of formula (V):

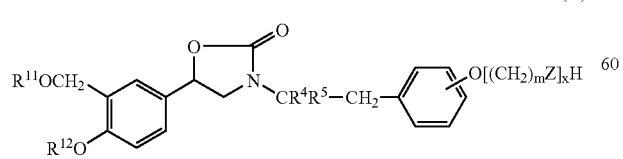

(V)

wherein $R^4$, $R^5$, $R^{11}$, $R^{12}$, Z and m are as defined for the compound of formula (II) and x is as defined below, with a compound of forumla (VI):

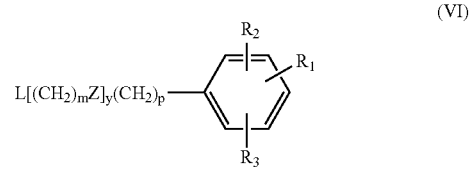

(VI)

wherein $R^1$, $R^2$, $R^3$, Z and p are as defined for the compound of formula (I), L is a leaving group such as halo (typically chloro, bromo or iodo) or a sulphonate eg. alkylsulphonate (typically methanesulphonate), and x and y each represent 1 or zero such that the sum of x and y is 1. When x is 1, Z preferably represents O.

The reaction of formula (V) and formula (VI) is advantageously effected in the presence of a base such as sodium hydride, or an inorganic carbonate, for example cesium carbonate or potassium carbonate.

Compounds of formula (VI) are commercially available or may be prepared by methods well known to a person skilled in the art.

Compounds of formula (V) may be prepared by coupling a compound of formula (VII):

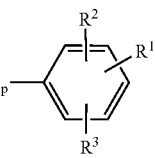

(VII)

or a salt or solvate thereof, wherein $R^{11}$ and $R^{12}$ are as defined for the compound of formula (V) with a compound of formula (VIII):

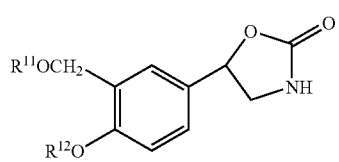

(VIII)

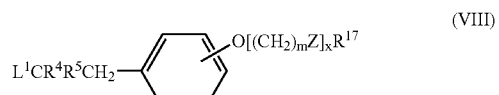

wherein $R^4$, $R^5$, Z and m are as defined for the formula (I), x is zero or 1, $L^1$ is a leaving group, for example a halo group, (typically bromo or iodo) or a sulphonate such as an alkyl sulphonate (typically methanesulphonate) an aryl sulphonate (typically toluenesulphonate) or a haloalkyl-sulphonate (typically trifluoromethane sulphonate), and $R^{17}$ is a hydroxyl protecting group, such as an acyl group. The group $R^{17}$ may be removed by standard methods; alternatively, the $R^{17}$ protected compound corresponding to formula (V) may be utilised directly in the reaction with formula (VI).

The coupling of a compound of formula (VII) with a compound of formula (VIII) may be effected in the presence of a base, such as a metal hydride, for example sodium hydride, or an inorganic base such as cesium carbonate, in an aprotic solvent, for example N,N-dimethylformamide. The protecting group $R^{17}$ may be removed using standard methods, using eg. potassium trimethylsilanolate or sodium hydroxide. Those skilled in the art will appreciate that when potassium silanolate is employed then it is preferable to use only 1 equivalent and mild reaction conditions (room temperature) as an excess of this reagent and high temperature will result in cleavage of the oxazolidinone ring.

Compounds of formula (VII) may be prepared by ring closure of a compound of formula (IX):

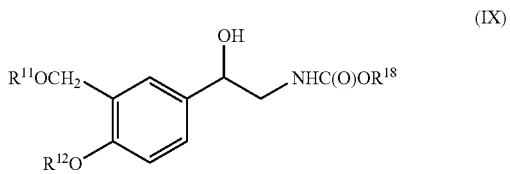

wherein $R^{11}$ and $R^{12}$ are as defined for the compound of formula (VII) and $R^{18}$ is $C_{1-6}$alkyl, for example tert-butyl, or aryl, for example phenyl. The ring closure may be effected by treatment with a base, such as a metal hydride, for example sodium hydride, in the presence of an aprotic solvent, for example, N,N-dimethylformamide.

Compounds of formula (IX) may be prepared from the corresponding ketone of formula (X):

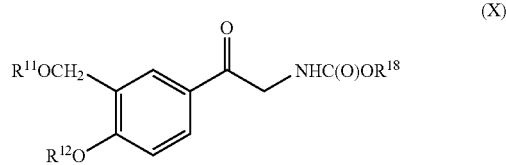

wherein $R^{11}$ and $R^{12}$ and $R^{18}$ are as defined for the compound of formula (IX), by reduction by any suitable method, for example by treatment with borane, in the presence of a chiral catalyst, such as CBS-oxazaborolidine, in a suitable solvent such as tetrahydrofuran.

The compound of formula (X) may be prepared from the corresponding halide of formula (XI):

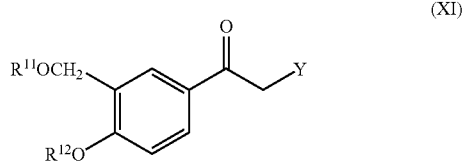

wherein $R^{11}$ and $R^{12}$ are as defined for the compound of formula (IV) and Y is a halo, suitably bromo.

The conversion of a compound of formula (XI) to a compound of formula (X) may be effected by reaction with the protected amine $HN(COOR^{18})_2$ wherein $R^{18}$ is as defined for the compound of formula (X) in the presence of an inorganic base such as cesium carbonate, followed by selective removal of one of the $COOR^{18}$ groups, for example by treatment with an acid such as trifluoroacetic acid.

Compounds of formula (XI) may be prepared from the corresponding compound having free hydroxymethyl and hydroxy substituents (which itself may be prepared from 2-bromo-1-(4-hydroxy)-3-hydroxymethyl-phenethyl)ethanone, the preparation of which is described in GB2140800, by treatment with 2-methoxypropene in acetone in the presence of an acid e.g. p-toluenesulphonic acid in a nitrogen atmosphere or by other standard methods) by forming the protected groups $R^{11}OCH_2$— and $R^{12}O$— wherein $R^{11}$ and $R^{12}$ are as defined for the compound of formula (XI). Such methods are described in DE 3513885 (Glaxo).

Compounds of formula (VIII) may be prepared from a compound of formula (XII):

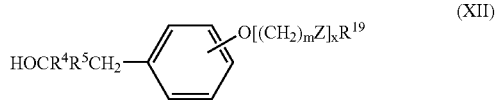

wherein x is zero or 1 and $R^{19}$ is a hydroxyl protecting group such as aralkyl, typically benzyl, by conventional chemistry, for example by conversion of the hydroxyl group to a mesylate which may itself be converted to bromo by addition of a salt such as tetraalkylammonium bromide in a solvent such as acetonitrile, followed by removal of the protecting group $R^{19}$ using standard conditions eg. hydrogenation in the presence of palladium on charcoal, and then introduction of $R^{17}$, for example by reaction with an acyl anhydride.

Compounds of formula (XII) wherein x is zero are known in the art or can readily be prepared by the skilled person using standard methods.

Compounds of formula (XII) wherein x is 1 may be prepared from a corresponding compound wherein x is zero by reaction with an appropriate alkylating agent.

Compounds of formulae (II) or (III) where $R^{13}$ is hydrogen or a protecting group may also be prepared according to the general methods described below.

In a further process (b) a compound of formula (I), may be obtained by alkylation of an amine of formula (XIII):

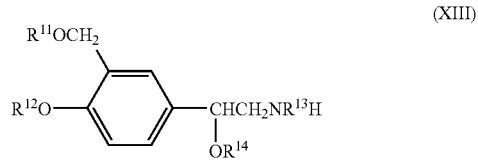

wherein $R^{11}$, $R^{12}$, $R^{13}$ and $R^{14}$ are each independently either hydrogen or a protecting group, for example as described hereinabove for compounds of formula (II) and (III);

with a compound of formula (XIV):

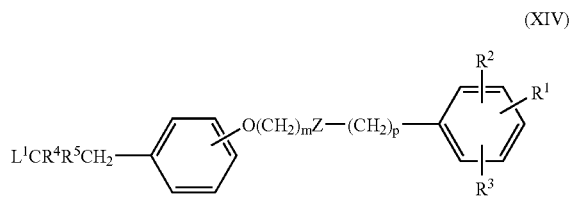
(XIV)

wherein $L^1$ is a leaving group as herein before defined for the compound of formula (VIII); followed by removal of any protecting groups present by conventional methods as described above for the deprotection of compounds of formula (II) and (III). For speed of reaction, $L^1$ is preferably bromo or is converted to bromo in situ, from the corresponding compound wherein $L^1$ is methanesulphonate, for example by addition of tetrabutylammonium bromide to the reaction mixture. In this process $R^{13}$ is preferably hydrogen.

The compound of formula (I), may be formed directly (when in the compound of formula (XIII) $R^{11}$, $R^{12}$, $R^{13}$ and $R^{14}$ are each hydrogen) or via a compound of formula (II) or (III) which may or may not be isolated (when in the compound of formula (XIII) at least one of $R^{11}$, $R^{12}$, $R^{13}$ and $R^{14}$ is a protecting group).

The reaction of compounds of formulae (XIII) and (XIV) is optionally effected in the presence of an organic base such as a trialkylamine, for example, diisopropylethylamine, and in a suitable solvent for example N,N-dimethylformamide, or acetonitrile.

Compounds of formula (XIII) are known in the art (for example EP-A 0947498) or may be readily prepared by a person skilled in the art, for example from the corresponding halide of formula (XI) as defined above. The conversion of a compound of formula (XI) to a compound of formula (XIII) may be effected by reaction with sodium azide in a suitable solvent, for example N,N-dimethylformamide, to give the corresponding compound wherein Y denotes $N_3$. The carbonyl group may then be reduced to the corresponding alcohol by any suitable method, for example by treatment with borane, in the presence of a chiral catalyst, such as (R)-tetrahydro-1-methyl-3,3-diphenyl-1H,3H-pyrrolo[1,2-c][1,3,2]oxazaborole, in a suitable solvent such as tetrahydrofuran. The azide group may be reduced to the corresponding amine group by any suitable method, for example by catalytic hydrogenation in the presence of a catalyst such as palladium/charcoal or platinum oxide.

Compounds of formula (XIV) may be prepared by general methods described hereinabove, as will be evident to a person skilled in the art, for example using methods similar to those used in the preparation of compounds (XII) and the reaction of compounds (V) and (VI).

In a further process (c) a compound of formula (I), may be prepared by reacting a compound of formula (XV):

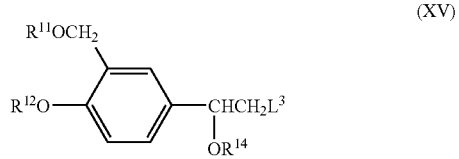
(XV)

wherein $R^{11}$, $R^{12}$ and $R^{14}$ are as hereinbefore defined and $L^3$ is a leaving group, with an amine of formula (XVI):

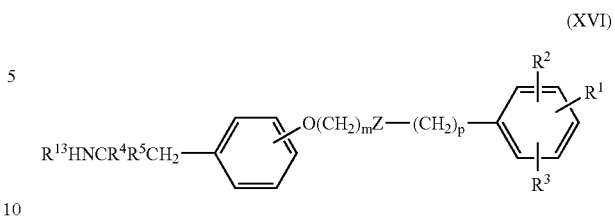
(XVI)

wherein $R^1$, $R^2$, $R^3$, $R^4$, $R^5$, Z, m, and p are as defined for the compounds of formula (I), and $R^{13}$ is either hydrogen or a protecting group, followed by removal of any protecting groups present by conventional methods as described above for the deprotection of compounds of formula (II).

The reaction may be effected using conventional conditions for such displacement reactions.

Compounds of formula (XV) may be prepared by methods known in the art.

Compounds of formula (XVI) may be prepared by reacting a compound of formula (XIV) with an amine $R^{13}NH_2$.

According to a further process (d) compounds of formula (I) wherein one of $R^4$ and $R^5$ represents alkyl may be prepared by reacting a compound of formula (XIII):

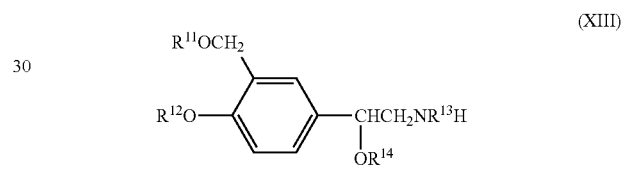
(XIII)

as hereinbefore defined,
with a compound of formula (XVII):

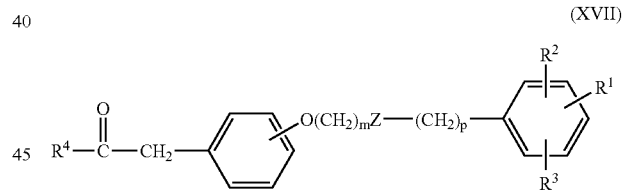
(XVII)

wherein $R^1$, $R^2$, $R^3$, $R^4$, Z, m, and p are as defined for the compounds of formula (I), under conditions suitable to effect reductive amination, for example in the presence of a reducing agent such as a borohydride, typically tetramethylammonium (triacetoxy) borohydride.

Compounds of formula (XVII) may be prepared by alkylation of a compound of formula (XVIII)

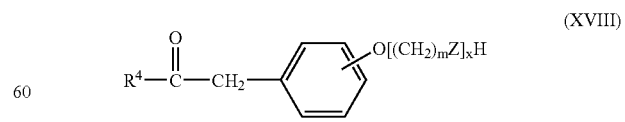
(XVIII)

wherein $R^4$, Z and m are as defined for formula (I) and x is zero or 1, with a compound of formula (VI) as hereinbefore defined using methods analogous to those described hereinbefore for the preparation of compounds of formula (IV).

Compounds of formula (XVIII) wherein x is zero are commerically available or may readily be prepared by conventional methods. Compounds of formula (XVIII) where x is 1 may be prepared from a corresponding compound wherein x is zero by appropriate alkylation.

It will be appreciated that at any convenient stage in the preparation of a compound of formula (I) one or more of the substituents $R^1$, $R^2$ and $R^3$ may, if appropriate, be converted into a different substituent. Conveniently such conversion may be effected on a compound of formula (IV) prior to the deprotection stages.

Thus for example a compound wherein $R^1$ represents $NO_2$ may be converted into a compound wherein $R^1$ represents —$NH_2$ for example by hydrogenation, e.g. in the presence of a palladium or platinum catalyst and in a solvent such as an alcohol. A compound wherein $R^1$ represents —$NH_2$ may be converted into a compound wherein $R^1$ represents XN $R^6C(O)N$ $R^7$ $R^8$ by reaction with an appropriate isocyanate or into a compound wherein $R^1$ represents L-XN $R^6(CO)N$ $(CO)N$ $R^7$ $R^8$ using excess isocyanate—similarly, amide and sulfonamide derivatives may be formed by reaction with an appropriate acyl or sulfonyl chloride or anhydride. Alternatively a simple amide substituent may be prepared from the corresponding nitrile, by treatment with a base such as potassium trimethylsilanolate.

To prepare a compound wherein $R^1$ represents $SR^6$, $SOR^6$ or $SO_2R^6$ a compound wherein $R^1$ represents halo, e.g.iodo may be reacted with an appropriate mercaptan $R^6SH$ in the presence of 1,1' bis-(diphenylphosphino)ferrocene, tris (dibenzylideneacetone) di-palladium, N-methylpyrrolidinone and an organic base such as triethylamine. The sulfide product initially obtained from this reaction may if desired be oxidised to give the corresponding compound wherein $R^1$ represents a group $SOR^6$. Oxidation may be carried out using conventional oxidising agents, for example sodium periodate, in a suitable solvent, for example an alcohol such as ethanol.

When $R^1$ represents $SOR^6$ the product may initially be obtained as a mixture of diastereoisomers. These may be separated by conventional methods, for example using chiral chromatography, such as chiral HPLC. Alternatively the sulphoxides can be prepared selectively in one of the diastereomeric forms by the use of a chiral oxidising agent.

A compound wherein $R^1$ represents $SO_2R^6$ may be prepared by oxidation of a corresponding compound wherein $R^1$ represents $SOR^6$ or $SR^6$ by reaction with a peracid, for example metachlorperbenzoic acid. When a sulfide (ie $R^1$ represents $SR^6$) is employed as the starting material, the peracid should be used in excess, to ensure complete oxidation.

To prepare a compound wherein $R^1$ represents phenyl or substituted phenyl a compound wherein $R^1$ represents halo, e.g.iodo may be reacted with an appropriate arylboronic acid or arylboronic acid ester in the presence of a catalyst system such as palladium, for example, tetrakis(triphenylphosphine) palladium (0) or bis(diphenylphosphino)ferrocene palladium dichloride with a base such as sodium carbonate or caesium carbonate, in a suitable solvent for example 1,2-dimethoxyethane, or N,N-dimethylformamide.

Other transformations will be apparent to those skilled in the art, and may be effected by conventional reactions.

It will be appreciated that in any of the routes (a) to (d) described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

The enantiomeric compounds of the invention may be obtained (i) by separation of the components of the corresponding racemic mixture, for example, by means of a chiral chromatography column, enzymic resolution methods, or preparing and separating suitable diastereoisomers, or (ii) by direct synthesis from the appropriate chiral intermediates by the methods described above.

Optional conversions of a compound of formula (I), to a corresponding salt may conveniently be effected by reaction with the appropriate acid or base. Optional conversion of a compound of formula (I), to a corresponding solvate or physiologically functional derivative may be effected by methods known to those skilled in the art.

According to a further aspect, the present invention provides novel intermediates for the preparation of compounds of formula (I), for example compounds of formula (II), (III), (IV) or (V).

For a better understanding of the invention, the following Examples are given by way of illustration.

SYNTHETIC EXAMPLES

Throughout the examples, the following abbreviations are used:
LCMS: Liquid Chromatography Mass Spectrometry
HPLC: High Performance Liquid Chromatography
RT: retention time
DCM: dichloromethane
EtOAc: ethyl acetate
EtOH: ethanol
DMAP: N,N-Dimethylaminopyridine
DMF: N,N-Dimethylformamide
MeOH: methanol
THF: tetrahydrofuran
h: hour(s)
min: minute(s)

All temperatures are given in degrees centigrade.

Flash silica gel refers to Merck Art No. 9385; silica gel refers to Merck Art No. 7734 Biotage refers to prepacked silica gel cartridges containing KP-Sil run on flash 12i chromatography module.

Solid Phase Extraction (SPE) columns are pre-packed cartridges used in parallel purifications, normally under vacuum. These are commercially available from Varian. SCX cartridges are Ion Exchange SPE columns where the stationary phase is polymeric benzene sulfonic acid. These are used to isolate amines.

LCMS was conducted on a Supelcosil LCABZ+PLUS column (3.3 cm×4.6 mm ID) eluting with 0.1% $HCO_2H$ and 0.01 M ammonium acetate in water (solvent A) and 0.05% $HCO_2H$ 5% water in acetonitrile (solvent B), using the following elution gradient 0.0-7min 0% B, 0.7-4.2 min 100% B, 4.2-5.3 min 100% B, 5.3-5.5 min 0% B at a flow rate of 3 mL/min. The mass spectra were recorded on a Fisons VG Platform spectrometer using electrospray positive and negative mode (ES+ve and ES−ve).

Preparative mass directed HPLC was conducted on a Waters FractionLynx system comprising of a Waters 600 pump with extended pump heads, Waters 2700 autosampler, Waters 996 diode array and Gilson 202 fraction collector on a 10 cm×2.54 cm ID ABZ+column, eluting with 0.1% formic acid in water (solvent A) and 0.1% formic acid in acetonitrile (solvent B), using the following elution gradient: 0.0-1.0 min 15% B, 1.0-10.0 min 55% B, 10.0-14.5 min 99% B, 14.5-14.9 min 99% B, 14.9-15.0 min 15%B at a flow rate of 20 ml/min and detecting at 200-320 nm at room temperature. Mass spectra were recorded on Micromass ZMD mass spectrometer using electrospray positive and negative mode, alternate scans. The software used was MassLynx 3.5 with OpenLynx and FractionLynx options.

EXAMPLE 1

N-{3-[(2-[4-[2-({(2R)-2-Hydroxy-2-[4-hydroxy-3-(hydroxymethyl)phenyl]ethyl}amino)ethyl]phenox] ethoxy)methyl]phenyl}urea acetate i) 2-{4-[2-(Benzyloxy)ethoxy]phenyl}ethul methanesulfonate A solution of 2-{4-[2-(benzyloxy)ethoxy]phenyl}ethanol (JP 10152460) (5 g) in DCM (35 mL) was cooled to 0° C. under nitrogen. This was treated with N,N-diisopropylethylamine (6.4 mL) and methanesulfonyl chloride (1.6 mL) and stirred at this temperature for 1 h. The solution was then concentrated in vacuo, and the residue was taken up in EtOAc and washed with 2M HCl, NaHCO$_3$, and brine. The combined organic layers were dried (MgSO$_4$) and concentrated in vacuo to give the title compound (6.33 g). LCMS RT=3.33 min.

ii) 1-[2-(Benzyloxy)ethoxy]-4-(2-bromoethyl)benzene

A mixture of 2-{4-[2-(benzyloxy)ethoxy]phenyl}ethyl methanesulfonate (6.33 g) and tetrabutylammonium bromide (11.6 g) in acetonitrile (35 mL) was heated at 50° C. under nitrogen for 6 h. The mixture was then concentrated in vacuo, and the residue was taken up in EtOAc and washed with water and brine. The combined organic layers were dried (MgSO$_4$) and concentrated in vacuo to give the title compound (5.23 g). LCMS RT=3.79 min.

iii) 2-[4-(2-Bromoethyl)phenoxy]ethanol

1-[2-(benzyloxy)ethoxy]-4-(2-bromoethyl)benzene in EtOAc (150 mL) and EtOH (50 mL) was hydrogenated over 10% Pd/C (530 mg) at room temperature and atmospheric pressure for 8 h. The catalyst was removed by filtration over Celite, washed with EtOAc and concentrated in vacuo to give the title compound (3.6 g). LCMS RT=2.82 min.

iv) 2-[4-(2-Bromoethyl)phenoxy]ethyl acetate

A mixture of 2-[4-(2-bromoethyl)phenoxy]ethanol (900 mg), acetic anhydride (0.5 mL), triethylamine (1.0 mL) and DMAP (13 mg) in DCM (5 mL) was stirred at room temperature for 0.5 h. The reaction was quenched by pouring into aq. NaHCO$_3$ and the organic layer was washed with 2M HCl, dried (MgSO$_4$) and concentrated in vacuo to give the title compound (1.03 g). LCMS RT=3.32 min.

v) Di(tert-butyl) 2-(2,2-dimethyl-4H-1.3-benzodioxin-6-yl)-2-oxoethylimidodicarbonate Cesium carbonate (70.4 g) was added to a stirred suspension of 2-bromo-1-(2,2-dimethyl-4H-1,3-benzodioxin-6-yl) ethanone, (Glaxo, DE 3513885, 1985) (61.8 g) and di-t-butyl iminodicarboxylate (47.15 g) in acetonitrile (600 ml) under nitrogen. After vigorous stirring at 21° for 24 h the mixture was diluted with water (ca800 ml) and the product was extracted with diethyl ether (1 litre, then 200 ml). The combined organic layers were washed with brine, dried (MgSO$_4$) and concentrated to ca400 ml. The white crystals were collected by filtration, washed with diethyl ether and dried to give the title compound (24.4 g) δ (CDCl$_3$) 7.78 (1H, dd, J 8, 2 Hz), 7.65 (1H, brs), 6.87 (1H, d, J 8 Hz), 4.97(2H, s), 4.88 (2H, s), 1.56 (6H, s) and 1.48 (18H, s). Further concentration of the mother liquors gave additional product (13.8 g). A third crop (7.1 g) was obtained by chromatographing the mother liquors on silica gel, evaporating the appropriate eluate and triturating with diethyl ether.

vi) tert-Butyl 2-(2.2-dimethyl-4H-1.3-benzodioxin-6-yl)-2-oxoethylcarbamate

Trifluoroacetic acid (92 ml) was added to a stirred solution of di(tert-butyl) 2-(2,2-dimethyl-4H-1,3-benzodioxin-6-yl)-2-oxoethylimidodicarbonate, (352.55 g) in dichloromethane (3.6 litres) at 21° and the reaction was stirred for 1.5 h. Aqueous NaOH solution (1.75 litres) was added and after 10 min the phases were separated. The organic layer was washed with water, dried (MgSO$_4$) and evaporated to an oil. This was stored under high vacuum overnight and then triturated with hexane:ether (3:1) to give the crude product (226.61 g). This was purified by recrystallisation from diethyl ether to give the title compound (122.78 g). Further product (61.5 g) was obtained from the mother liquors by evaporation and chromatography on a Biotage using 15% ethyl acetate in hexane. LCMS RT=3.37 min.

vii) tert-Butyl (2R)-2-(2.2-dimethyl-4H-1,3-benzodioxin-6-yl)-2-hydroxyethylcarbamate A 2M solution of borane—dimethyl sulphide in THF (28 ml) was added slowly to a 1M solution of (R)-tetrahydro-1-methyl-3,3-diphenyl-1H,3H-pyrrolo[1,2-c][1,3,2]ox-azaborole in toluene (56 ml) at 0° under nitrogen. A solution of tert-butyl 2-(2,2-dimethyl-4H1,3-benzodioxin-6-yl)-2-oxoethylcarbamate, (108.2 g) in THF (1.3 litres) was added slowly keeping the temperature below 5° followed by 2M solution of borane—dimethyl sulphide in THF (252 ml) over 50 min. After 1 h, 2M HCl (170 ml) was added with cooling and the mixture was partitioned between ethyl acetate and water. The organic layer was washed with saturated NaHCO$_3$ solution and brine and dried (MgSO$_4$). The solution was concentrated and the product purified by chromatography on flash silica gel (800 g), eluting successively with hexane: ethyl acetate (4:1 then 3:1) to give the title compound (93.3 g), LCMS RT=3.31 min.

viii) (5R)-5-(2.2-Dimethyl-4H-1.3-benzodioxin-6-yl)-1.3-oxazolidin-2-one tert-Butyl (2R)-2-(2,2-dimethyl-4H-1,3-benzodioxin-6-yl)-2-hydroxyethylcarbamate, (86.37 g) in DMF (600 ml) was added dropwise to a stirred suspension of sodium hydride (60% oil dispersion, 11.9 g) in DMF (160 ml) with cooling such that the internal temperature remained at 0° under nitrogen. The mixture was stirred at 21° for 2 h. The mixture was recooled to 0° and 2M HCl (134 ml) was added. The mixture was diluted with water and the product was extracted with ethyl acetate twice. The solution was washed with brine twice, dried (MgSO$_4$) and evaporated to give the title compound (63.55 g) LCMS RT=2.66 min.

ix) 2-(4-{2-[(5R)-5-(2,2-Dimethyl-4H-1,3-benzodioxin-6-yl)-2-oxo-1,3-oxazolidin-3-yl]ethyl}phenoxy)ethyl acetate (5R)-5-(2,2-Dimethyl-4H-1,3-benzodioxin-6-yl)-1,3-oxazolidin-2-one (651 mg) in DMF (15 mL) was treated with sodium hydride (84 mg) under nitrogen and stirred for 1 h. A solution of 2-[4-(2-bromoethyl)phenoxy]ethyl acetate (500 mg) in DMF (5 mL) was added and the reaction mixture was stirred for a further 2 h. This was then concentrated in vacuo and the residue was taken up in EtOAc, washed with water, brine and dried (MgSO$_4$). The solution was concentrated in vacuo and the residue was purified by chromatography (Biotage, 90 g) eluting with cyclohexane-EtOAc (2:1) to give the title compound (355 mg). LCMS RT=3.26 min.

x) (5R)-5-(2,2-Dimethyl-4H-1,3-benzodioxin-6-yl)-3-{2-[4-(2-hydroxyethoxy)phenyl]ethyl}-1,3-oxazolidin-2-one 2-(4-{2-[(5R)-5-(2,2-Dimethyl-4H-1,3-benzodioxin-6-yl)-2-oxo-1,3-oxazolidin-3-yl]ethyl}phenoxy)ethyl acetate (3.7 g) in THF (100 mL) was treated with KOSiMe₃ (1.39 g) and stirred at room temperature for 3 h. The solution was then poured into phosphate buffer (pH 6.5) and water, extracted with EtOAc, dried (MgSO₄) and concentrated in vacuo to give the title compound (3.31 g). LCMS RT=2.91 min.

xi) (5R)-5-(2,2-Dimethyl-4H-1,3-benzodioxin-6-yl)-3-[2-(4-{2-[(3-nitrobenzyl)oxy]ethoxy}phenyl)ethyl]-1,3-oxazolidin-2-one (5R)-5-(2,2-Dimethyl-4H-1,3-benzodioxin-6-yl)-3-{2-[4-(2-hydroxyethoxy)phenyl]ethyl}-1,3-oxazolidin-2-one (1 g) in DMF (15 mL) was treated with sodium hydride (167 mg) under nitrogen and stirred for 15 min. To this was added 3-nitrobenzyl bromide (721 mg) and the reaction mixture was stirred for 20 h. The solution was then concentrated in vacuo and the residue was taken up in EtOAc, washed with water and brine, dried (MgSO₄) and concentrated in vacuo. The residue was purified by chromatography (Biotage, 40 g) eluting with CH₂Cl₂-MeOH (500:1) and then CH₂Cl₂-MeOH (250:1) to give the title compound (1.22 g). LCMS RT=3.57 min.

xii) (5R)-3-[2-(4-{2-[(3-Aminobenzyl)oxy]ethoxy}phenyl)ethyl]-5-(2,2-dimethyl-4H-1,3-benzodioxin-6-yl)-1,3-oxazolidin-2-one (5R)-5-(2,2-Dimethyl-4H-1,3-benzodioxin-6-yl)-3-[2-(4-{2-[(3-nitrobenzyl)oxy]ethoxy}phenyl)ethyl]-1,3-oxazolidin-2-one (1.22 g) in EtOAc (20 mL) and EtOH (15 mL) was hydrogenated over PtO₂ (122 mg) at room temperature and atmospheric pressure for 3 h. The catalyst was then removed by filtration over Celite, washed with EtOAc and concentrated in vacuo to give the title compound (994 mg). LCMS RT=3.23 min.

xiii) N-(3-{[2-(4-{2-[(5R)-5-(2,2-Dimethyl-4H-1,3-benzodioxin-6-yl)-2-oxo-1,3-oxazolidin-3-yl]ethyl}phenoxy)ethoxy]methyl}phenyl)urea and N-(3-{[2-(4-{2-[(5R)-5-(2,2-dimethyl-4H-1,3-benzodioxin-6-yl)-2-oxo-1,3-oxazolidin-3-yl]ethyl}phenoxy)ethoxy]methyl}phenyl)dicarbonimidic diamide A mixture of (5R)-3-[2-(4-{2-[(3-aminobenzyl)oxy]ethoxy}phenyl)ethyl]-5-(2,2-dimethyl-4H-1,3-benzodioxin-6-yl)-1,3-oxazolidin-2-one (100 mg) and acetic acid (0.1 mL) in THF (1 mL) was treated with a suspension of sodium cyanate (25 mg) in water and stirred at room temperature for 4 h. The solution was diluted in EtOAc, washed with NaHCO₃, brine and concentrated in vacuo to give a mixture of N-(3-{[2-(4-{2-[(5R)-5-(2,2-dimethyl-4H-1,3-benzodioxin-6-yl)-2-oxo-1,3-oxazolidin-3-yl]ethyl}phenoxy)ethoxy]methyl}phenyl)urea and N-(3-{[2-(4-{2-[(5R)-5-(2,2-dimethyl-4H-1,3-benzodioxin-6-yl)-2-oxo-1,3-oxazolidin-3-yl]ethyl}phenoxy)ethoxy]methyl}phenyl)dicarbonimidic diamide as a 72:28 ratio respectively. LCMS RT=3.15 min and 3.27 min.

xiv) N-[3-({2-[4-(2-{[(2R)-2-(2,2-Dimethyl-4H-1,3-benzodioxin-6-yl)-2-hydroxyethyl]amino}ethyl)phenoxy]ethoxy}methyl)phenyl]urea and N-[3-({2-[4-(2-{[(2R)-2-(2,2-dimethyl-4H-1,3-benzodioxin-6-yl)-2-hydroxyethyl]amino}ethyl)phenoxy]ethoxy}methyl)phenyl]dicarbonimidic diamide The mixture of N-(3-{[2-(4-{2-[(5R)-5-(2,2-dimethyl-4H-1,3-benzodioxin-6-yl)-2-oxo-1,3-oxazolidin-3-yl]ethyl}phenoxy)ethoxy]methyl}phenyl)urea and N-(3-{[2-(4-{2-[(5R)-5-(2,2-dimethyl-4H-1,3-benzodioxin-6-yl)-2-oxo-1,3-oxazolidin-3-yl]ethyl}phenoxy)ethoxy]methyl}phenyl)dicarbonimidic diamide (135 mg) in THF (2 mL) was treated with KOSiMe₃ (123 mg) and the resulting solution was heated at 75° C. under nitrogen for 1.5 h. The reaction mixture was then quenched with MeOH and concentrated in vacuo. The residue was taken up in EtOAc, washed with water, dried (MgSO₄) and concentrated in vacuo. The residue was purified by HPLC to give N-[3-({2-[4-(2-{[(2R)-2-(2,2-dimethyl-4H-1,3-benzodioxin-6-yl)-2-hydroxyethyl]amino}ethyl)phenoxy]ethoxy}methyl)phenyl]urea (12 mg). LCMS RT=2.47 min and N-[3-({2-[4-(2-{[(2R)-2-(2,2-dimethyl-4H-1,3-benzodioxin-6-yl)-2-hydroxyethyl]amino}ethyl)phenoxy]ethoxy}methyl)phenyl]dicarbonimidic diamide (6 mg). LCMS RT=2.58 min.

xv) N-[3-[(2-{4-[2-({(2R)-2-Hydroxy-2-[4-hydroxy-3-(hydroxymethyl)phenyl]ethyl}amino)ethyl]phenoxy}ethoxy)methyl]phenyl}urea acetate N-[3-({2-[4-(2-{[(2R)-2-(2,2-Dimethyl-4H-1,3-benzodioxin-6-yl)-2-hydroxyethyl]amino}ethyl)phenoxy]ethoxy}methyl)phenyl]urea (12 mg) in acetic acid (1.5 mL) and water (0.5 mL) was heated at 75° C. for 0.5 h. The solution was then concentrated in vacuo and azeotroped with MeOH to give the title compound (13 mg). LCMS RT=2.18 min. ES+ve 496 (MH)⁺

EXAMPLE 2

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}dicarbonimidic diamide acetate Prepared using methods similar to those described in Example 1 xv) LCMS RT=2.30 min. ES+ve 539 (MH)⁺

EXAMPLE 3

4-((1R)-2-{[2-(4-{2-[(3-Fluorobenzyl)oxy]ethoxy}phenyl)ethyl]amino}-1-hydroxyethyl)-2-(hydroxymethyl)phenol acetate i) (5R)-5-(2,2-Dimethyl-4H-1,3-benzodioxin-6-yl)-3-[2-(4-{2-[(3-fluorobenzyl)oxy]ethoxy}phenyl)ethyl]-1,3-oxazolidin-2-one Prepared using methods similar to those described in Example 1 xi) LCMS RT=3.62 min.

ii) 4-((1R)-2-{[2-(4-{2-[(3-Fluorobenzyl)oxy]ethoxy}phenyl)ethyl]amino}-1-hydroxyethyl)-2-(hydroxymethyl)phenol acetate (5R)-5(2,2-Dimethyl-4H-1,3-benzodioxin-6-yl)-3-[2-(4-(2-[(3-fluorobenzyl)oxy]ethoxy}phenyl)ethyl]-1,3-oxazolidin-2-one (125 mg) in THF (1 mL) was treated with KOSiMe₃ and the resulting solution was heated at 75° C. for 2 h. The solution was then diluted in MeOH, passed down an SCX-2 cartridge (10 g) and then concentrated in vacuo. The residue was purified by chromatography (SPE, 5 g) eluting with CH₂Cl₂-MeOH-2M NH₃ in MeOH (98:1:1) and then CH₂Cl₂-MeOH-2M NH₃ in MeOH (95:4:1) to give the free base of the title compound. This was converted to the acetate salt using acetic acid to give the title compound (38 mg). LCMS RT=2.56 min. ES+ve 456 (MH)⁺

EXAMPLE 4

2-(Hydroxymethyl)-4-((1R)-1-hydroxy-2-{[2-(4-{2-[(3-methylbenzyl)oxy]ethoxy}phenyl)ethyl]amino}ethyl)phenol acetate i) (5R)-5-(2,2-Dimethyl-4H-1,3-benzodioxin-6-yl)-3-[2-(4-{2-[(3-methylbenzyl)oxy]ethoxy}phenyl)ethyl]-1,3-oxazolidin-2-one
Prepared using methods similar to those described in Example 1 xi) LCMS RT=3.69 min.

ii) 2-(Hydroxymethyl)-4-((1R)-1-hydroxy-2-{[2-(4-{2-[(3-methylbenzyl)oxy]ethoxy}phenyl)ethyl]amino}ethyl)phenol acetate
Prepared using methods similar to those described in Example 3 ii) LCMS RT=2.62 min. ES+ve 452 (MH)+

EXAMPLE 5

4-((1R)-2-{[2-(4-{2-[(3-Chlorobenzyl)oxy]ethoxy}phenyl)ethyl]amino}-1-hydroxyethyl)-2-(hydroxymethyl)phenol acetate i) (5R)-3-[2-(4-{2-[(3-Chlorobenzyl)oxy]ethoxy}phenyl)ethyl]-5-(2,2-dimethyl-4H-1,3-benzodioxin-6-yl)-1,3-oxazolidin-2-one
Prepared using methods similar to those described in Example 1 xi) LCMS RT=3.73 min.

ii) 4-((1R)-2-{[2-(4-2-[(3-Chlorobenzyl)oxy]ethoxy}phenyl)ethyl]amino}-1-hydroxyethyl)-2-(hydroxymethyl)phenol acetate
Prepared using methods similar to those described in Example 3 ii) LCMS RT=2.66 min. ES+ve 472/474 (MH)+

EXAMPLE 6

4-((1R)-1-Hydroxy-2-{[2-(4-{2-[(3-iodobenzyl)oxy]ethoxy}phenyl)ethyl]amino}ethyl)-2-(hydroxymethyl)phenol acetate i) (5R)-5-(2,2-Dimethyl-4H-1,3-benzodioxin-6-yl)-3-[2-(4-{2-[(3-iodobenzyl)oxy]ethoxy}phenyl)ethyl]-1,3-oxazolidin-2-one
Prepared using methods similar to those described in Example 1 xi) LCMS RT=3.90 min.

ii) 4-((1R)-1-Hydroxy-2-{[2-(4-{2-[(3-iodobenzyl)oxy]ethoxy}phenyl)ethyl]amino}ethyl)-2-(hydroxymethyl)phenol acetate
Prepared using methods similar to those described in Example 3 ii) LCMS RT=2.75 min. ES+ve 564 (MH)+

EXAMPLE 7

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}acetamide acetate i) N-(3-{[2-(4-{2-[(5R)-5-(2,2-Dimethyl-4H-1,3-benzodioxin-6-yl)-2-oxo-1,3-oxazolidin-3-yl]ethyl}phenoxy)ethoxy]methyl}phenyl)acetamide
A mixture of (5R)-3-[2-(4-{2-[(3-aminobenzyl)oxy]ethoxy}phenyl)ethyl]-5-(2,2-dimethyl-4H-1,3-benzodioxin-6-yl)-1,3-oxazolidin-2-one {Example 1 xii)} (100 mg), acetic anhydride (21 μL) and N,N-diisopropylethylamine (67 μL) in DCM (2 mL) was stirred at room temperature under nitrogen for 20 h. The solution was then diluted in DCM, washed with 2M HCl, NaHCO$_3$ and brine, dried (MgSO$_4$) and concentrated in vacuo to give the title compound (136 mg). LCMS RT=3.24 min.

ii) N-[3-({2-[4-(2-{[(2R)-2-(2,2-Dimethyl-4H-1,3-benzodioxin-6-yl)-2-hydroxyethyl]amino}ethyl)phenoxy]ethoxy}methyl)phenyl]acetamide
Prepared using methods similar to those described in Example 1 xiv) LCMS RT=2.57 min iii) N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}acetamide acetate
Prepared using methods similar to those described in Example 1 xv) LCMS RT=2.20 min. ES+ve 495 (MH)+

EXAMPLE 8

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}nicotinamide acetate i) N-(3-{[2-(4-{2-[(5R)-5-(2,2-Dimethyl-4H-1,3-benzodioxin-6-yl)-2-oxo-1,3-oxazolidin-3-yl]ethyl}phenoxy)ethoxy]methyl}phenyl)nicotinamide
A mixture of (5R)-3-[2-(4-{2-[(3-aminobenzyl)oxy]ethoxy}phenyl)ethyl]-5-(2,2-dimethyl-4H-1,3-benzodioxin-6-yl)-1,3-oxazolidin-2-one {Example 1 xii)} (100 mg), nicotinoyl chloride hydrochloride (38 mg) and N,N-diisopropylethylamine (67 μL) in DCM (2 mL) was stirred at room temperature under nitrogen for 20 h. The solution was then diluted in DCM, washed with 2M HCl, NaHCO$_3$ and brine, dried (MgSO$_4$) and concentrated in vacuo to give the title compound (136 mg). LCMS RT=3.32 min.

ii) N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}nicotinamide acetate
Prepared using methods similar to those described in Example 3 ii) LCMS RT=2.34 min. ES+ve 558 (MH)+

EXAMPLE 9

N-{3-[(2-{4-[2-({(2R)-2-Hydroxyl-2-[4-hydroxy-3-(hydroxymethyl)phenyl]ethyl}amino)ethyl]phenoxy}ethoxy)methyl]phenyl}-2-furamide acetate i) N-(3-{[2-(4-{2-[(5R)-5-(2,2-Dimethyl-4H-1,3-benzodioxin-6-yl)-2-oxo-1,3-oxazolidin-3-yl]ethyl}phenoxy)ethoxy]methyl}phenyl)-2-furamide
Prepared using methods similar to those described in Example 8 i) LCMS RT=3.44 min.

ii) N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}-2-furamide acetate
N-(3-{[2-(4-{2-[(5R)-5-(2,2-Dimethyl-4H-1,3-benzodioxin-6-yl)-2-oxo-1,3-oxazolidin-3-yl]ethyl}phenoxy)ethoxy]methyl}phenyl)-2-furamide (34 mg) in THF (2 mL) was treated with KOSiMe$_3$ (18 mg) and the resulting solution was heated at 75° C. for 4 h. The reaction mixture was then quenched with MeOH and concentrated in vacuo. The residue was then purified by HPLC, before dissolving in acetic acid (1 mL) and water (0.33 mL) and heating at 75°

EXAMPLE 10

3-[(2-{4-[2-({(2R)-2-Hydroxy-2-[4-hydroxy-3-(hydroxymethyl)phenyl]ethyl}amino)ethyl]phenoxy}ethoxy)methyl]benzamide acetate i) 3-{[2-(4-{2-[(5R)-5-(2,2-Dimethyl-4H-1,3-benzodioxin-6-yl)-2-oxo-1,3-oxazolidin-3-yl]ethyl}phenoxy)ethoxy]methyl}benzonitrile Prepared using methods similar to those described in Example 1 xi) LCMS RT=3.48 min.

ii) 3-({2-[4-(2-{[(2R)-2-(2,2-Dimethyl-4H-1,3-benzodioxin-6-yl)-2-hydroxyethyl]amino}ethyl)phenoxy]ethoxy}methyl)benzamide 3-{[2-(4-{2-[(5R)-5-(2,2-Dimethyl-4H-1,3-benzodioxin-6-yl)-2-oxo-1,3-oxazolidin-3-yl]ethyl}phenoxy)ethoxy]methyl}benzonitrile (125 mg) in THF (3 mL) was treated with KOSiMe$_3$ (152 mg) and the resulting solution was heated at 75° C. for 4 h. The reaction mixture was then quenched with MeOH and concentrated in vacuo. The residue was taken up in EtOAc, washed with phosphate buffer (pH=6.5) and water, dried (MgSO$_4$) and concentrated in vacuo. The residue was purified by chromatography (SPE, 5 g) eluting with CH$_2$Cl$_2$-MeOH-2M NH$_3$ in MeOH (196:3:1) and then CH$_2$Cl$_2$: MeOH: 2M NH$_3$/MeOH (96:3:1) to give the title compound (42 mg). LCMS RT=2.40 min.

iii) 3-[(2-{4-[2-({(2R)-2-Hydroxy-2-[4-hydroxy-3-(hydroxymethyl)phenyl]ethyl}amino)ethyl]phenoxy}ethoxy)methyl]benzamide acetate Prepared using methods similar to those described in Example 1 xv) LCMS RT=2.12 min. ES+ve 481 (MH)$^+$

EXAMPLE 11

3-[(2-{4-[2-({(2R)-2-Hydroxy-2-[4-hydroxy-3-(hydroxymethyl)phenyl]ethyl}amino)ethyl]phenoxy}ethoxy)methyl]benzonitrile acetate i) 3-{[2-(4-{2-[(5R)-5-(2,2-Dimethyl-4H-1,3-benzodioxin-6-yl)-2-oxo-1,3-oxazolidin-3-yl]ethyl}phenoxy)ethoxy]methyl}benzonitrile Prepared using methods similar to those described in Example 1 xi) LCMS RT=3.48 min.

ii) 3-({2-[4-(2-{[(2R)-2-(2,2-Dimethyl-4H-1,3-benzodioxin-6-yl)-2-hydroxyethyl]amino}ethyl)phenoxy]ethoxy}methyl)benzonitrile Prepared using method described in Example 10 ii) but reaction was heated at 75° C. for only 2 h. LCMS RT=2.67 min.

iii) 3-[(2-{4-[2-({(2R)-2-Hydroxy-2-[4-hydroxy-3-(hydroxymethyl)phenyl]ethyl}amino)ethyl]phenoxy}ethoxy)methyl]benzonitrile acetate Prepared using methods similar to those described in Example 1 xv) LCMS RT=2.47 min. ES+ve 463 (MH)$^+$

EXAMPLE 12

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}methanesulfonamide acetate i) N-(3-{[2-(4-{2-[(5R)-5-(2,2-Dimethyl-4H-1,3-benzodioxin-6-yl)-2-oxo-1,3-oxazolidin-3-yl]ethyl}phenoxy)ethoxy]methyl}phenyl)methanesulfonamide A solution of (5R)-3-[2-(4-{2-[(3-aminobenzyl)oxy]ethoxy}phenyl)ethyl]-5-(2,2-dimethyl-4H-1,3-benzodioxin-6-yl)-1,3-oxazolidin-2-one (Example 1 xii)) (117 mg) in pyridine (10 mL) was stirred with methanesulfonyl chloride (39 mg) at 20° C. for 90 min. The reaction mixture was partitioned between aqueous NaHCO$_3$ and DCM. The organic solution was dried (Na$_2$SO$_4$), and the solvent was removed in vacuo to yield the title compound (138 mg). LCMS RT=3.30 min ii) N-[3-({2-[4-(2-{[(2R)-2-(2,2-Dimethyl-4H-1,3-benzodioxin-6-yl)-2-hydroxyethyl]amino}ethyl)phenoxy]ethoxy}methyl)phenyl]methanesulfonamide Prepared using methods similar to those described in Example 1 xiv). LCMS RT=2.59 min iii) N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}methanesulfona mide acetate Prepared using methods similar to those described in Example 1 xv). LCMS RT=2.37 min, ES+ve=531 (MH)$^+$

EXAMPLE 13

4-{(1R)-2-[(2-{4-[2-)Benzyloxy]ethoxy]phenyl}ethyl)amino]-1-hydroxyethyl}-2-(hydroxymethyl)phenol acetate i) (5R)-3-(2-{2-[2-Benzyloxy)ethoxy]phenyl}ethyl)-5-(2,2-dimethyl-4H-1,3-benzodioxin-6-yl)-1,3-oxazolidin-2-one A solution of (5R)-5-(2,2-dimethyl-4H-1,3-benzodioxin-6-yl)-1,3-oxazolidin-2-one (Example 1 viii) (503 mg) in DMF (10 mL) was treated with sodium hydride (60% dispersion in mineral oil) (97 mg) under nitrogen for 20 min. A solution of 1-[2-(benzyloxy)ethoxy]-4-(2-bromoethyl)benzene (676 mg) in DMF (5 mL) was added and the reaction sfirred for a further 2 h. The reaction mixture was concentrated in vacuo then the residue was prified by chromatography (Biotage, 40 g) eluting with EtOAc-petroleum ether (2:3) to give the title compound (585 mg). LCMS RT=3.66 min ii) (1R)-2-[(2-{4-[2-(Benzyloxy)ethoxy]phenyl}ethyl)amino]-1-(2,2-dimethyl-4H-1,3-benzodioxin-6-yl)ethanol Prepared using methods similar to those described in Example 1 (xiv). LCMS RT=2.77 min.

iii) 4-{(1R)-2-[(2-{4-[2-(Benzyloxy)ethoxy]phenyl}ethyl)aminol]-1-hydroxyethyl}-2-(hydroxymethyl) acetate Prepared using methods similar to those described in Example 1 (xv). LCMS RT=2.47 min, ES+ve=438 (MH)$^+$

EXAMPLE 14

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}-N-phenylurea acetate i) N-(3-{[2-(4-{2-[(5R)-5-(2,2-Dimethyl-4H-1,3-benzodioxin-6-yl)-2-oxo-1,3-oxazolidin-3-yl]ethyl}phenoxy)ethoxy]methyl}phenyl)-N-phenylurea A stirred mixture of (5R)-3-[2-(4-{2-[(3-Aminobenzyl)oxy]ethoxy}phenyl)ethyl]-5-(2,2-dimethyl-4H-1,3-benzodioxin-6-yl)-1,3-oxazolidin-2-one (95 mg) in DCM (10 ml) under nitrogen was treated with phenylisocyanate (0.04 ml) and the mixture stirred at 20° C. for 4 h. Isopropanol (10 ml) was added and the mixture stirred for 18 h. The solvents were evaporated in vacuo to give a residue which was purified by SPE (5 g). Elution with EtOAc-cyclohexane (3:2) gave the title compound (104 mg). LCMS RT=3.53 min.

ii) N-[3-({2-[4-(2-{[(2R)-2-(2,2-Dimethyl-4H-1,3-benzodioxin-6-yl)-2-hydroxyethyl]amino}ethyl)phenoxy]ethoxy}methyl)phenyl]-N-phenylurea Prepared using methods similar to those described in Example 1 xiv LCMS RT=2.75 min.

iii) N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}-N-phenylurea acetate Prepared using methods similar to those described in Example 1 xv LCMS RT=2.75 min, ES+ve 572 (MH)+.

EXAMPLE 15

4-((1R)-1-Hydroxy-2-{[2-(4-[2-[(3-hydroxybenzyl)oxy]ethoxy}phenyl)ethyl]amino}ethyl)-2-(hydroxymethyl)phenol acetate i) 2-(4-{2-[(5R)-5-(2,2-Dimethyl-4H-1,3-benzodioxin-6-yl)-2-oxo-1,3-oxazolidin-3-yl]ethyl}phenoxy)ethyl methanesulfonate A solution of (5R)-5-(2,2-dimethyl-4H-1,3-benzodioxin-6-yl)-3-{2-[4-(2-hydroxyethoxy)phenyl]ethyl}-1,3-oxazolidin-2-one (450 mg) in DCM (20 ml) at 0° C. under nitrogen was treated with diisopropylethylamine (0.23 ml) followed by methanesulphonyl chloride (0.09 ml) and the mixture was stirred at 0° C. for 1 h. Saturated NaHCO$_3$ solution was added and the mixture was vigorously stirred for 5 min. The layers were separated and the organic phase washed with saturated NaHCO$_3$ solution, dried (Na$_2$SO$_4$) and the solvent evaporated in vacuo to give the title compound (528 mg). LCMS RT=3.15 min.

ii) (5R)-5-(2,2-Dimethyl-4H-1,3-benzodioxin-6-yl)-3-[2-(4-{2-[(3-{[2-(trimethylsilyl)ethoxy]methoxy}benzyl)oxy]ethoxy}phenyl)ethyl]-1,3-oxazolidin-2-one A solution of (3-{[2-(trimethylsilyl)ethoxy]methoxy}phenyl)methanol in DMF (5 ml) under nitrogen was treated with sodium hydride (18 mg, 60% in oil) and the mixture was stirred at 20° C. for 15 min. 2-(4-{2-[(5R)-5-(2,2-Dimethyl-4H-1,3-benzodioxin-6-yl)-2-oxo-1,3-oxazolidin-3-yl]ethyl}phenoxy)ethyl methanesulfonate (150 mg) was added and the mixture was stirred at 20° C. for 20 h. Phosphate buffer solution (20 ml, pH6.5) was added and the mixture was extracted with EtOAc (30 ml). The organic extract was washed with water (2×20 ml) and dried (Na$_2$SO$_4$). The solvent was evaporated in vacuo to give a residue which was purified by chromatography on flash silica gel. Elution with EtOAc-petroleum ether 40°-60° (1:1) gave the title compound (90 mg) LCMS RT=4.07 min.

iii) 4-((1R)-1-Hydroxy-2-{[2-(4-{2-[(3-hydroxybenzyl)oxy]ethoxy}phenyl)ethyl]amino}ethyl)-2-(hydroxymethyl)phenol acetate Prepared using methods similar to those described in Example 3ii LCMS RT=2.26 min, ES+ve 454 (MH)+.

EXAMPLE 16

4-{(1R)-2-[((1S)-2-{4-[2-(Benzyloxy)ethoxy]phenyl}-1-methylethyl)amino]-1-hydroxyethyl}-2-(hydroxymethyl)phenol acetate i) 1-(4-{[tert-Butyl(dimethyl)silyl]oxy}phenyl)acetone A solution of tert-butyldimethylsilyl chloride (13.6 g) in DMF (50 ml) was added dropwise to stirred solution of 4-hydroxyphenylacetone (12.5 g) and imidazole (9.0 g) in DMF (150 ml) at 20° under N$_2$. After 0.67 h additional tert-butyldimethylsilyl chloride (4.7 g) was added and the reaction stirred for 0.75 h. The reaction mixture was concentrated in vacuo and the residue partitioneed between Et$_2$O and water. The organic phase was washed with water, brine, dried (MgSO$_4$) and evaporated to dryness. The residue was purified by chromatography on a Biotage (90 g) eluting with cyclohexane-Et$_2$O (9:1) to give the title compound (17.5 g), ES+ve 282 (M+NH$_4$)+ ii) (1R)-2-{[2-(4-{[tert-Butyl(dimethyl)silyl]oxy}phenyl)-1-methylethyl]amino}-1-(2,2-dimethyl-4H-1,3-benzodioxin-6-yl)ethanol Tetramethylammonium (triacetoxy)borohydride (0.94 g) was added to a stirred solution of (1R)-2-amino1-(2,2-dimethyl-4H-1,3-benzodioxin-6-yl)ethanol (0.49 g) and 1-(4-{[tert-butyl(dimethyl)silyl]oxy}phenyl)acetone (0.57 g) in CH$_2$Cl$_2$ (10 ml). Acetic acid (0.2 ml) was added and the reaction stirred for 18 h at 20° C. The mixture was diluted with H$_2$O and extracted with EtOAc. The organic phase was washed with brine, dried (MgSO$_4$) and evaporated to dryness. The residue was purified by chromatography on a Biotage (40 g) eluting with CH$_2$Cl$_2$-MeOH-2M NH$_3$ in MeOH (150:8:1) to give the title compound (0.84 g), ES+ve 472 (MH)+ iii) (5R)-3-[(1R)-2-(4-{[tert-Butyl(dimethyl)silyl]oxy}phenyl)-1-methylethyl]-5-(2,2-dimethyl-4H-1,3-benzodioxin-6-yl)-1,3-oxazolidin-2-one and (5R)-3-[(1S)-2-(4-{[tert-butyl(dimethyl)silyl]oxy}phenyl)-1-methylethyl]-5-(2,2-dimethyl-4H-1,3-benzodioxin-6-yl)-1,3-oxazolidin-2-one 1,1'-Carbonyldiimidazole (0.62 g) was added to a solution of (1R)-2-{[2-(4-{[tert-butyl(dimethyl)silyl]oxy}phenyl)-1-methylethyl]amino}-1-(2,2-dimethyl-4H-1,3-benzodioxin-6-yl)ethanol (0.83 g) in THF (8 ml). The mixture was stirred for 18 h at 20° C. and partitioned between Et$_2$O and water. The organic phase was washed with brine, dried (MgSO$_4$) and evaporated to dryness. The residue was purified by chromatography on a Biotage (40 g) eluting with cyclohexane-EtOAc (5:1 then 3:1) to give (5R)-3-[(1S)-2-(4-{[tert-butyl(dimethyl)silyl]oxy}phenyl)-1-methylethyl]-5-(2,2-dimethyl-4H-1,3-benzodioxin-6-yl)-1,3-oxazolidin-2-one (0.32 g), LCMS RT=4.17 min and (5R)-3-[(1R)-2-(4-{[tent-butyl(dimethyl)silyl]oxy}phenyl)-1-methylethyl]-5-(2,2-dimethyl-4H-1,3-benzodioxin-6-yl)-1,3-oxazolidin-2-one (0.36 g) LCMS RT=4.15 min.

iv) (5R)-5-(2,2-Dimethyl-4H-1,3-benzodioxin-6-yl)-3-[(1S)-2-(4-hydroxychenyl)-1-methylethyl]-1,3-oxazolidin-2-one A solution of tetrabutylammonium fluoride in THF (1M, 0.65 ml) was added to a stirred solution of (5R)-3-[(1S)-2-(4-{[tert-butyl(dimethyl)silyl]oxy}phenyl)-1-methylethyl]-5-(2,2-dimethyl-4H-1,3-benzodioxin-6-yl)-1,3-oxazolidin-2-one (0.294 g) in THF (3 ml). After stirring at 20° C. for 0.5 h the mixture was partitioned between EtOAc (30 ml) and H$_2$O (30 ml). The organic phase was washed with brine, dried (MgSO$_4$) and evaporated to dryness. The residue was purified by chromatography on a Biotage (40 g) eluting with cyclohexane-EtOAc (3:1) to give the title compound (0.23 g), ES+ve 384 (MH)$^+$ v) (5R)-3-((1S)-2-{4-[2-(Benzyloxy)ethoxy]phenyl}-1-methylethyl)-5-(2,2-dimethyl-4H-1,3-benzodioxin-6-yl)-1,3-oxazolidin-2-one Benzyl 2-bromoethyl ether (0.164 ml) was added to a stirred mixture of (5R)-5-(2,2-dimethyl-4H-1,3-benzodioxin-6-yl)-3-[(1S)-2-(4-hydroxyphenyl)-1-methylethyl]-1,3-oxazolidin-2-one (0.27 g) and cesium carbonate (0.48 g) in DMF (3 ml). The reaction mixture was stirred for 18 h at 20° C. then partitioned between Et$_2$O (30 ml) and water (30 ml). The organic phase was washed with brine, dried (MgSO$_4$) and evaporated to dryness. The residue was purified by chromatography on a Biotage (8 g) eluting with cyclohexane-Et$_2$O (1:1) to give the title compound (0.31 g), ES+ve 535 (M+NH$_4$)$^+$ vi) (1R)-2-[((1S)-2-{4-[2-(Benzyloxy)ethoxy]phenyl}-1-methylethyl)amino]-1-(2,2-dimethyl-4H-1,3-benzodioxin-6-yl)ethanol Prepared using method similar to those described in Example 1 xiv ES+ve 492 (MH)$^+$ vii) 4-{(1R)-2-[((1S)-2-{4-[2-(Benzyloxy)ethoxy]phenyl}-1-methylethyl)amino]-1-hydroxyethyl}-2-(hydroxymethyl)phenol acetate Prepared using method similar to those described in Example 1 xv LCMS RT=2.52 min ES+ve 452 (MH)$^+$

EXAMPLE 17

4-{(1R)-2-{((1R)-2-{4-[2-(Benzyloxy)ethoxy]phenyl}-1-methylethyl)amino]-1-hydroxyethyl}-2-(hydroxymethyl)phenol acetate i) (5R)-3-((1R)-2-{4-[2-(Benzyloxy)ethoxy]phenyl}-1-methylethyl)-5-(2,2-dimethyl-4H-1,3-benzodioxin-6-yl)-1,3-oxazolidin-2-one Prepared using methods similar to those described in Example 16 v ES+ve 535 (M+NH$_4$)$^+$ ii) (1R)-2-[((1R)-2-{4-[2-(Benzyloxy)ethoxy]phenyl}-1-methylethyl)amino]-1-(2,2-dimethyl-4H-1,3-benzodioxin-6-yl)ethanol Prepared using methods similar to those described in Example 1 xiv ES+ve 492 (MH)$^+$ iii) 4-{(1R)-2-[((1R)-2-{4-[2-(Benzyloxy)ethoxy]phenyl}-1-methylethyl)amino]-1-hydroxyethyl}-2-(hydroxymethyl)phenol acetate Prepared using methods similar to those described in Example 1 xv LCMS RT=2.52 min ES+ve 452 (MH)$^+$

EXAMPLE 18

3-[(2-{4-[2-({(2R)-2-Hydroxy-2-[4-hydroxy-3-(hydroxymethyl)phenyl]ethyl}amino)ethyl]phenoxy}ethoxy)methyl]benzenesulfonamide i) 3-Hydroxymethylbenzenesulfonamide
3-(Aminosulfonyl)benzoic acid (2.18 g) was stirred with ice-water cooling and under nitrogen while borane-THF complex (32.5 ml) was added dropwise over 15 min. After 2 h at 22° further borane-THF complex (16 ml) was added. After a further 2 h the mixture was cooled with ice-water and methanol (40 ml) was added dropwise. After 15 min 2M hydrochloric acid (90 ml) was added and the mixture was left to stand at 21° overnight. The solution was extracted 3 times with ethyl acetate and the organic layers were combined and washed twice with brine, dried (MgSO$_4$) and concentrated. This solution was loaded onto a column of silica gel (200 g) and the column was run with ethyl acetate and then 10% methanol in ethyl acetate to give the title compound (1.595 g), LCMS RT=0.83 min.

ii) 3-(Hydroxymethyl)-N,N-bis{[2-(trimethylsilyl)ethoxy]methyl}benzenesulfonamide
Sodium hydride (60% oil dispersion, 0.315 g) was added to 3-hydroxymethylbenzenesulfonamide (0.67 g) with stirring in DMF (20 ml) under nitrogen at 20°. After 15 min, 2-(trimethylsilyl)ethoxymethyl chloride (1.27 ml) was added and stirring was continued for 1.5 h. pH 6.4 Phosphate buffer and ethyl acetate were added. The aqueous layer was extracted twice with ethyl acetate and the combined organic layers were washed twice with brine, dried (MgSO$_4$) and evaporated to an oil. This oil in dichloromethane was loaded onto a column of silica gel (75 g) set up in 10% ethyl acetate in 40-60 petroleum ether. The column was run with this, then 20%, 30% and 50% ethyl acetate in 40-60 petroleum ether to give the title compound (0.74 g) LCMS RT=4.00 min.

iii) 3-(Bromomethyl)-N,N-bis{[2-(trimethylsilyl)ethoxy]methyl}benzenesulfonamide
3-(Hydroxymethyl)-N,N-bis{[2-(trimethylsilyl)ethoxy]methyl}benzenesulfonamide (0.735 g) was stirred with ice-water cooling in dichloromethane (32 ml) under nitrogen and carbon tetrabromide (0.962 g) and triphenylphosphine (0.646 g) were added successively. After 5 min the cooling bath was removed and the mixture was stirred at 21° for 4 h. The mixture was poured onto an SPE silica cartridge (10 g). The cartridge was eluted with dichloromethane to give the title compound (0.21 g) LCMS RT=4.31 min.

iv) 3-{[2-(4-{2-[(5R)-5-(2,2-Dimethyl-4H-1,3-benzodioxin-6-yl)-2-oxo-1,3-oxazolidin-3-yl]ethyl}phenoxy)ethoxy]methyl}-N,N-bis{[2-(trimethylsilyl)ethoxy]methyl}benzenesulfonamide Prepared using methods similar to those in Example 1 xi) LCMS RT=4.38 min v) 3-({2-[4-(2-{[(2R)-2-(2,2-Dimethyl-4H-1,3-benzodioxin-6-yl)-2-hydroxyethyl]amino}ethyl)phenoxy]ethoxy}methyl)-N N-bis{[2-(trimethylsilyl)ethoxy]methyl}benzenesulfonamide Prepared using methods similar to those in Example 1 xiv) LCMS RT=3.50 min vi) 3-1(2-{4-[2-({(2R)-2-Hydroxy-2-[4-hydroxy-3-(hydroxymethyl)phenyl]ethyl}amino)ethyl]phenoxy}ethoxy)methyl]benzenesulfonamide
3-({2-[4-(2-{[(2R)-2-(2,2-Dimethyl-4H-1,3-benzodioxin-6-yl)-2-hydroxyethyl]amino}ethyl)phenoxy]

ethoxy}methyl)-N,N-bis{[2-(trimethylsilyl)ethoxy]
methyl}benzenesulfonamide (0.015 g) was heated at 75° for
6 h in acetic acid (1.5 ml) and water (0.75 ml). The solution
was evaporated to dryness and re-evaporated twice with
methanol to give crude product (0.012 g). This was purified
by preparative layer chromatography on a silica plate (20×
20 cm) which was developed twice in dichloromethane:
ethanol: 0.880 ammonia solution, 25:8:1. After elution of the
required band using methanol in dichloromethane, the eluate
was evaporated to dryness and re-evaporated successively
with acetic acid in methanol and then methanol to give the
title compound (0.0037 g) LCMS RT=2.19 min. ES+ve 517
(MH)+

EXAMPLE 19

3-[(2-{4-[2-({(2R)-2-Hydroxy-2-[4-hydroxy-3-(hydroxymethyl)phenyl]ethyl}amino)ethyl]
phenoxy}ethoxy)methyl]-N-isopropylbenzenesulfonamide i) 3-(Hydroxymethyl)-N-isopropylbenzenesulfonamide Sodium hydride (60% oil dispersion, 0.177 g) was added
to 3-hydroxymethylbenzenesulfonamide (0.77 g) with stirring in DMF (15 ml) under nitrogen at 21°. After 10 min,
isopropyl iodide (0.45 ml) was added followed by a further
0.3 ml after 1 h. After an additional 2 h more isopropyl
iodide (0.2 ml) was added. After 3 days more sodium
hydride oil dispersion (0.08 g) was added. After another day,
the solution was poured into water acidified with 2M hydrochloric acid and the product was extracted with ethyl acetate
twice. The combined extracts were washed with brine and
evaporated to an oil. This oil was loaded onto a column of
silica gel (60 g) and the column was eluted successively with
30%, 50% and 70% ethyl acetate in 40-60 petroleum ether
to give the title compound (0.527 g) LCMS RT=2.22 min.

ii) 3-(Hydroxymethyl)-N-isopropyl-N-{[2-(trimethylsilyl)
ethoxy]methyl}benzenesulfonamide Prepared using methods similar to those in example 18 ii)
LCMS RT=3.75 min iii) 3-(Bromomethyl)-N-isopropyl-N-{[2-(trimethylsilyl)
ethoxy]methyl}benzenesulfonamide Prepared using methods similar to those in example 18 iii)
LCMS RT=3.91 min iv) 3-{[2-(4-{2-[(5R)-5-(2,2-Dimethyl-4H-1,3-benzodioxin-6-yl)-2-oxo-1,3-oxazolidin-3-yl]ethyl}phenoxy)
ethoxy]methyl}-N-isopropyl-N-{[2-(trimethylsilyl)ethoxy]
methyl}benzenesulfonamide Prepared using methods similar to those in Example 1 xi)
LCMS RT=4.07 min v) 3-({2-[4-(2-{[(2R)-2-(2,2-Dimethyl-4H-1,3-benzodioxin-6-yl)-2-hydroxyethyl]amino}ethyl)phenoxy]
ethoxy}methyl)-N-isopropyl-N-{[2-(trimethylsilyl)ethoxy]
methyl}benzenesulfonamide Prepared using methods similar to those in Example 1
xiv) LCMS RT=3.26 min vi) 3-[(2-{4-[2-({(2R)-2-Hydroxy-2-[4-hydroxy-3-(hydroxymethyl)phenyl]ethyl}amino)ethyl]phenoxy}ethoxy)
methyl]-N-isopropylbenzenesulfonamide Prepared using methods similar to those in Example 1 xv)
LCMS RT=2.44 min. ES+ve 559 (MH)+

EXAMPLE 20

3-[(2-{4-[2-({(2R)-2-Hydroxy-2-[4-hydroxy-3-(hydroxymethyl)phenyl]ethyl}amino)ethyl]
phenoxy}ethoxy)methyl]benzoic acid acetate i) Methyl 3-{[2-(4-{2-[(5R)-5-(2,2-dimethyl-4H-1,3-benzodioxin-6-yl)-2-oxo-1,3-oxazolidin-3-yl]ethyl}phenoxy)
ethoxy]methyl}benzoate Prepared using methods similar to those described in
Example 1 xi) LCMS RT=3.66 min.

ii) 3-({2-[4-(2-{[(2R)-2-(2,2-Dimethyl-4H-1,3-benzodioxin-6-yl)-2-hydroxyethyl]amino}ethyl)phenoxy]
ethoxy}methyl)benzoic acid Prepared using methods similar to those described in
Example 1 xiv) LCMS RT=2.70 min.

iii) 3-[(2-{4-[2-({(2R)-2-Hydroxy-2-[4-hydroxy-3-(hydroxymethyl)phenyl]ethyl}amino)ethyl]phenoxy}ethoxy)
methyl]benzoic acid acetate Prepared using methods similar to those described in
Example 1 xv) LCMS RT=2.32 min. ES+ve 482 (MH)+

EXAMPLE 21

4-((1R)-2-{[2-(4-{2-[(4-Fluorobenzyl)oxy]
ethoxy}phenyl)ethyl]amino}-1-hydroxyethyl)-2-
(hydroxymethyl)phenol acetate i) (5R)-5-(2,2-Dimethyl-4H-1,3-benzodioxin-6-yl)-3-[2-(4-
{2-[(4-fluorobenzyl)oxy]ethoxy}phenyl)ethyl]-1,3-oxazolidin-2-one Prepared using methods similar to those described in
Example 1 xi). LCMS RT=3.70 min.

ii) 4-((1R)-2-{[2-(4-{2-[(4-Fluorobenzyl)oxy]
ethoxy}phenyl)ethyl]amino}-1-hydroxyethyl)-2-(hydroxymethyl)phenol acetate Prepared using methods similar to those described in
Example 3 ii). LCMS RT=2.49 min. ES+ve 456 (MH)+

EXAMPLE 22

4-((1R)-2-{[2-(4-{2-[(2,6-Dichlorobenzyl)oxy]
ethoxy]phenyl)ethyl]amino}-1-hydroxyethyl)-2-
(hydroxymethyl)phenol acetate i) (5R)-3-[2-(4-{2-[(2,6-Dichlorobenzyl)oxy]
ethoxy}phenyl)ethyl]-5-(2,2-dimethyl-4H-1,3-benzodioxin-
6-yl)-1,3-oxazolidin-2-one Prepared using methods similar to those described in
Example 1 xi). LCMS RT=3.79 min.

ii) 4-((1R)-2-{[2-(4-{2-[(2,6-Dichlorobenzyl)oxy]
ethoxy}phenyl)ethyl]amino}-1-hydroxyethyl)-2-(hydroxymethyl)phenol acetate (5R)-3-[2-(4-{2-[(2,6-Dichlorobenzyl)oxy]ethoxy}phenyl)ethyl]-5-(2,2-dimethyl-4H-1,
3-benzodioxin-6-yl)-1,3-oxazolidin-2-one (160 mg) in THF
(4 ml) was treated with KOSiMe$_3$ (179 mg) and the resulting
solution was heated at 75° C. for 2 h. The reaction mixture
was then quenched with MeOH and concentrated in vacuo.
The residue was then diluted in MeOH, and purified on an
SCX-2 cartridge (10 g) eluting with EtOH followed by 10% aqueous NH₃ in EtOH. The ammonia fractions were then combined and concentrated in vacuo. The residue was dissolved in acetic acid (3 ml) and water (1 ml) and heated at 75° C. for 20 min. The solution was then concentrated in vacuo and azeotroped with MeOH to give the title compound (115 mg). LCMS RT=2.49 min, ES+ve 506 (MH)⁺

EXAMPLE 23

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}sulfamide formate and N-(tert-butoxycarbonyl)-N-{3-[(2-{4-[2-({(2R)-2-hydroxy-2-[4-hydroxy-3-(hydroxymethyl)phenyl]ethyl}amino)ethyl]phenoxy}ethoxy)methyl]phenyl}sulfamide formate i) N-(tert-Butoxycarbonyl)-N-(3-{[2-(4-{2-[(5R)-5-(2,2-dimethyl-4H-1,3-benzodioxin-6-yl)-2-oxo-1,3-oxazolidin-3-yl]ethyl}phenoxy)ethoxy]methyl}phenyl)sulfamide A solution of chlorosulfonylisocyanate (34 mg) in DCM (1 ml) was cooled in ice before adding tert-butanol (0.023 ml). The mixture was then stirred for 2 h when diisopropylethylamine (0.13 ml) and a solution of (5R)-3-[2-(4-{2-[(3-aminobenzyl)oxy]ethoxy{phenyl]ethyl}-5-(2,2-dimethyl-4H-1,3-benzodioxin-6-yl)-1,3-oxazolidin-2-one {Example 1 xii)} (138 mg) in DCM (3 ml) was added. The resulting solution was then allowed to warm to room temperature and stood overnight. The solution was then diluted in DCM, washed with phosphate buffer (pH=6.5) and water, dried (MgSO₄) and concentrated in vacuo. The residue was then purified by chromatography (SPE, 5 g) eluting with cyclohexane-EtOAc (1:1) and then EtOAc to give the title compound (74 mg). LCMS RT=3.57 min.

ii) N-(tert-Butoxycarbonyl)-N-[3-({2-[4-(2- {[(2R)-2-(2,2-dimethyl-4H-1,3-benzodioxin-6yl)-2-hydroxyethyl] amino}ethyl)phenoxy]ethoxy}methyl)phenyl]sulfamide Prepared using methods similar to those described in Example 1 xiv). LCMS RT=2.79 min.

iii) N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}sulfamide formate and N-(tert-butoxycarbonyl)-N-{3-[(2-{4-[2-({(2R)-2-hydroxy-2-[4-hydroxy-3-(hydroxymethyl)phenyl]ethyl}amino)ethyl]phenoxy}ethoxy)methyl]phenyl}sulfamide formate N-(tert-Butoxycarbonyl)-N-[3-({2-[4-(2-{[(2R)-2-(2,2-dimethyl-4H-1,3-benzodioxin-6-yl)-2-hydroxyethyl]amino}ethyl)phenoxy]ethoxy}methyl)phenyl]sulfamide (15 mg) in acetic acid (1.5 ml) and water (0.5 ml) was heated at 75° C. for 0.5 h. The solution was then concentrated in vacuo and azeotroped with MeOH. The residue was purified by HPLC to give the title compounds N-{3-[(2-{4-[2-({(2R)-2-hydroxy-2-[4-hydroxy-3-(hydroxymethyl)phenyl]ethyl}amino)ethyl]phenoxy}ethoxy)methyl]phenyl}sulfamide formate (1.5 mg) LCMS RT=2.21 min, ES+ve 532 (MH)⁺and N-(tert-butoxycarbonyl)-N-{3-[(2-{4-[2-({(2R)-2-hydroxy-2-[4-hydroxy-3-(hydroxymethyl)phenyl]ethyl}amino)ethyl]phenoxy}ethoxy)methyl]phenyl}sulfamide formate (0.9 mg). LCMS RT=2.51 min ES+ve 630 (MH)⁺

EXAMPLE 24

4-[(1R)-2-({2-[4-(2-{[3-(Cyclopentylsulfonyl)benzyl]oxy}ethoxy)phenyl]ethyl}amino)-1-hydroxyethyl]-2-(hydroxamethyl)phenol acetate i) (5R-3-{2-[4-(2-{[3-Cyclopentylthio)benzyl]oxy}ethoxy)phenyl]ethyl}-5-(2,2-dimethyl-4H-1,3-benzodioxin-6-yl)-1, 3-oxazolidin-2-one To a solution of (5R)-5-(2,2-dimethyl-4H-1,3-benzodioxin-6-yl)-3-[2-(4-{2-[(3-iodobenzyl)oxy]ethoxy}phenyl)ethyl]-1,3-oxazolidin-2-one{Example 6 i)} (400 mg) in N-methylpyrrolidinone (3 ml) and Et₃N (0.5 ml) was added diphenylphosphinoferrocene (dppf) (84 mg) and tris(dibenzylideneacetone)dipalladium (0) [Pd₂(dba)₃] (34 mg). The solution was then flushed with nitrogen for 15 min before adding cyclopentylmercaptan (136 mg) and heating at 60° C. for 4 h. The solution was then allowed to cool to room temperature before pouring into aq. NaHCO₃ solution and extracting with EtOAc. The combined organic layers were then washed with water, dried (MgSO₄) and concentrated in vacuo. The residue was purified by chromatography (Biotage, 40 g) eluting with CH₂Cl₂-MeOH (500:1) to give the title compound (276 mg). LCMS RT=4.08 min.

ii) (5R)-3-{2-[4-(2-{[3-(Cyclopentylsulfinyl)benzyl]oxy}ethoxy)phenyl]ethyl}-5-(2,2-dimethyl-4H-1,3-benzodioxin-6-yl)-1,3-oxazolidin-2-one A solution of (5R)-3-{2-[4-(2-{[3-(cyclopentylthio)benzyl]oxy}ethoxy)phenyl]ethyl}-5-(2,2-dimethyl-4H-1,3-benzodioxin-6-yl)-1,3-oxazolidin-2-one (276 mg) in EtOH (15 ml) and water (5 ml) was treated with sodium periodate (391 mg) and stirred at room temperature under nitrogen for 3 h. The solution was concentrated in vacuo before pouring into water and extracting with EtOAc. The combined organic layers were washed with water, dried (MgSO₄) and concentrated in vacuo to give the title compound (278 mg). LCMS RT=3.42 min.

iii) (5R)-3-{2-[4-(2-{[3-(Cyclopentylsulfonyl)benzyl]oxy}ethoxy)phenyl]ethyl}-5-(2,2-dimethyl-4H-1,3-benzodioxin-6yl)-1,3-oxazolidin-2-one A solution of (5R)-3-{2-[4-(2-{[3-(cyclopentylsulfinyl)benzyl]oxy}ethoxy)phenyl]ethyl}-5-(2,2-dimethyl-4H-1,3-benzodioxin-6-yl)-1,3-oxazolidin-2-one (56 mg) in CH₂Cl₂ (2 ml) was cooled in an ice bath under a nitrogen atmosphere. To this was added 3-chloroperoxybenzoic acid (30 mg) and the resulting solution was allowed to warm to room temperature and stirred for 2 h. The solution was then washed with sodium sulphite, to remove any excess peroxide, and water. The combined organic layers were then dried (MgSO₄) and concentrated in vacuo to give the title compound (70 mg). LCMS RT=3.70 min.

iv) (1R)-2-({2-[4-(2-{[3-(Cyclopentylsulfonyl)benzyl]oxy}ethoxy)phenyl]ethyl}amino)-1-(2,2-dimethyl-4H-1,3-benzodioxin-6-yl)ethanol Prepared using methods similar to those described in Example 1 xiv). LCMS RT=2.91 min.

v) 4-[(1R)-2-({2-[4-(2-{[3-(Cylopentylsulfonyl)benzyl]oxy}ethoxy)phenyl]ethyl}amino)-1-hydroxyethyl]-2-(hydroxymethyl)phenol acetate Prepared using methods similar to those described in Example 1 xv). LCMS RT=2.62 min ES+ve 570 (MH)⁺

EXAMPLE 25

4-[(1R)-2-({2-[4-(2-{[3-(Cyclopentylsufinyl)benzyl]oxy}ethoxy)phenyl]ethyl}amino)-1-hydroxyethyl]-2-(hydroxymethyl)phenol acetate i) (1R)-2-({2-[4-(2-{[3-(Cyclopentylsulfinyl)benzyl]oxy}ethoxy)phenyl]ethyl}amino)-1-(2,2-dimethyl-4H-1,3-benzodioxin-6-yl)ethanol Prepared using methods similar to those described in Example 1 xiv) using (5R)-3-{2-[4-(2-{[3-(cyclopentylsulfinyl)benzyl]oxy}ethoxy)phenyl]ethyl}-5-(2,2-dimethyl-4H-1,3-benzodioxin-6-yl)-1,3-oxazolidin-2-one {Example 24 ii)}. LCMS RT=2.73 min.

ii) 4-[(1R)-2-({2-[4-(2-{[3-(Cyclopentylsulfinyl)benzyl]oxy}ethoxy)phenyl]ethyl}amino)-1-hydroxyethyl]-2-(hydroxymethyl)phenol acetate Prepared using methods similar to those described in Example 1 xv). LCMS RT=2.37 min.

EXAMPLE 26

4-((1R)-1-Hydroxy-2-{[2-(4-{2-[(4-isopropoxybenzyl)oxy]ethoxy}phenyl)ethyl]amino}ethyl)-2-(hydroxymethyl)phenol acetate i) (4-Isopropoxyphenyl)methanol 4-Hydroxybenzylalcohol (1 g) in DMF (10 ml) under nitrogen at 0° C. was treated portionwise with sodium hydride (355 mg). The resulting solution was stirred for 0.5 h before isopropyl bromide (0.99 g) was added, and the solution was stirred for a further 18 h. Phosphate buffer (pH=6.5) was then added and the solution was extracted with EtOAc. The combined organic layers were then washed with water, dried (MgSO$_4$) and concentrated in vacuo. The residue was purified by chromatography (Biotage, 90 g) eluting with 40-60° C. petroleum ether-EtOAc (4:1) to give the title compound (931 mg). LCMS RT=2.51 min.

ii) (5R)-5-(2,2-Dimethyl-4H-1,3-benzodioxin-6-yl)-3-[2-(4-{2-[(4-isopropoxybenzyl)oxy]ethoxy}phenyl)ethyl]-1,3-oxazolidin-2-one A solution of (4-isopropoxyphenyl)methanol (93 mg) in DMF (2 ml) was treated with sodium hydride (27 mg) under nitrogen and stirred for 0.5 h. To this was added the 2-(4-{2-[(5R)-5-(2,2-dimethyl-4H-1,3-benzodioxin-6-yl)-2-oxo-1,3-oxazolidin-3-yl]ethyl}phenoxy)ethyl methanesulfonate (357 mg) {Example 15 i)} and the resulting solution was stirred for 18 h under nitrogen. The solution was then diluted in EtOAc, washed with water, dried (MgSO$_4$) and concentrated in vacuo. The residue was purified by chromatography (Biotage, 40 g) eluting with 40-60° C. petroleum ether-EtOAc (2:1) to give the title compound (156 mg). LCMS RT=3.76 min.

iii) 4-((1R)-1-Hydroxy-2-{[2-(4-{2-[(4-isopropoxybenzyl)oxy]ethoxy}phenyl)ethyl]amino}ethyl)-2-(hydroxymethyl)phenol acetate Prepared using methods similar to those described in Example 22 ii). LCMS RT=2.56 min ES+ve 496 (MH)$^+$

EXAMPLE 27

4-((1R)-1-Hydroxy-2-{[2- (4-{2-[(4-hydroxybenzyl)oxy]ethoxy}phenyl)ethyl]amino}ethyl)-2-(hydroxymethyl)phenol acetate i) (4-{[2-(Trimethylsilyl)ethoxy]methoxy}phenyl)methanol
Prepared using methods similar to those described in Example 26 i). LCMS RT=3.42 min.

ii) (5R)-5-(2,2-Dimethyl-4H-1,3-benzodioxin-6-yl)-3-[2-(4-[2-[(4-{[2-(trimethylsilyl)ethoxy]methoxy}benzyl)oxy]ethoxy}phenyl)ethyl]-1,3-oxazolidin-2-one
Prepared using methods similar to those described in Example 26 ii). LCMS RT=4.09 min.

iii) 4-((1R)-1-Hydroxy-2-{[2-(4-{2-[(4-hydroxybenzyl)oxy]ethoxy}phenyl)ethyl]amino}ethyl)-2-(hydroxymethyl)phenol acetate (5R)-5-(2,2-Dimethyl-4H-1,3-benzodioxin-6-yl)-3-[2-(4-{2-[(4-{[2-(trimethylsilyl)ethoxy]methoxy}benzyl)oxy]ethoxy}phenyl)ethyl]-1,3-oxazolidin-2-one (287 mg) in THF (5 ml) was treated with KOSiMe$_3$ (570 mg) and the resulting solution was heated at 75° C. for 3 h. The reaction was then quenched in MeOH and concentrated in vacuo. The residue was purified by chromatography (SCX-2, two 10 g cartridges) eluting with 10% MeOH-CH$_2$Cl$_2$ and then 10% 2M NH$_3$ in MeOH—CH$_2$Cl$_2$. The residue was then dissolved in AcOH (3 ml) and water (1 ml) and heated at 75° C. for 2 h. The solution was then concentrated in vacuo and azeotroped with MeOH. The residue was purified by HPLC to give the formate salt of the title compound. This was converted to the acetate salt by dissolving in acetic acid and evaporating under reduced pressure to give the title compound (14 mg). LCMS RT=2.34 min ES+ve 454 (MH)$^+$

EXAMPLE 28

3-[(2-{4-[2-({(2R)-2-Hydroxy-2-[4-hydroxy-3-(hydroxymethyl)phenyl]ethyl}amino)ethyl]phenoxy}ethoxymethyl]-N-isopropylbenzamide acetate i) 2-(4-{[tert-Butyl(dimethyl)silyl]oxy}phenyl)ethanol Sodium hydride (60% dispersion in mineral oil, 145 mg) was added portionwise to a solution of 4-(2-hydroxyethyl)phenol (502 mg) in THF (15 ml) and the mixture was stirred at 20° C. for 30 min. tert-Butyldimethylsilyl chloride (547 mg) was added and the mixture was stirred for 75 min. Phosphate buffer solution (pH 6.5) was added and the mixture was extracted with EtOAc. The combined extracts were dried (Na$_2$SO$_4$) and the solvent evaporated in vacuo to give a residue which was purified by SPE (10 g). Elution with DCM-cyclohexane (1:3) then DCM then EtOAc gave the title compound (658 mg). LCMS RT=3.62 min.

ii) 2-(4-{[tert-Butyl(dimethyl)silyl]oxy}phenyl)ethyl methanesulfonate

A solution of 2-(4-((tert-butyl(dimethyl)silyl]oxy}phenyl)ethanol (653 mg) and diisopropylethylamine (1.8 ml) in DCM (15 ml) at 0° under nitrogen was treated with methanesulfonyl chloride (0.44 ml) and the mixture was stirred at 0° C. for 6 h. Saturated NaHCO$_3$ solution was added and the mixture stirred for 15 min. Water (20 ml) was added and the mixture was extracted with DCM. The extract was dried (Na$_2$SO$_4$) and the solvent evaporated in vacuo to give the title compound (904 mg). LCMS RT=3.85 min.

iii) [4-(2-Bromoethyl)phenoxy](tert-butyl)dimethylsilane

A solution of 2-(4-{[tert-butyl(dimethyl)silyl]oxy}phenyl)ethyl methanesulfonate (1.064 g) in acetonitrile (35 ml) was treated with tetrabutylammonium bromide (2.346 g) at 50° C. for 2.5 h. The mixture was cooled to 20° C. and the solvent was evaporated in vacuo. The residue was dissolved in EtOAc and the resulting solution washed with water and dried ($Na_2SO_4$). Solvent evaporation in vacuo gave the title compound (991 mg). LCMS RT=4.22 min.

iv) (1R)-2-{[2-(4-{[tert-Butyl(dimethyl)silyl]oxy}phenyl)ethyl]amino}-1-(2,2-dimethyl-4H-1,3-benzodioxin-6-yl)ethanol A solution of [4-(2-bromoethyl)phenoxy](tert-butyl)dimethylsilane (479 mg) in DMF (20 ml) under nitrogen was treated with (1R)-2-amino-1-(2,2-dimethyl-4H-1,3-benzodioxin-6-yl)ethanol (678 mg) and the mixture was stirred at 20° C. for 9.5 h. Phosphate buffer solution (pH 6.5) was added and the mixture was extracted with EtOAc. The extract was washed with water and dried ($Na_2SO_4$). Solvent evaporation in vacuo gave a residue which was purified by SPE (10 g). Elution with DCM then DCM-EtOH-0.880 ammonia solution (300:8:1) then (150:8:1) gave the title compound (991 mg). LCMS RT=3.13 min.

v) (5R)-5-(2,2-Dimethyl-4H-1,3-benzodioxin-6-yl)-3-[2-(4-hydroxyphenyl)ethyl]-1,3-oxazolidin-2-one A solution of (1R)-2-{[2-(4-{[tert-butyl(dimethyl)silyl]oxy}phenyl)ethyl]amino}-1-(2,2-dimethyl-4H-1,3-benzodioxin-6-yl)ethanol (4.803 g) in THF (100 ml) under nitrogen was treated with 1,1'carbonyldimidazole (1.702 g) and the mixture was stirred at 20° for 21.5 h. Water (125 ml) was added, the mixture was stirred for 10 min and then extracted with $Et_2O$. The extract was dried ($Na_2SO_4$) and the solvent evaporated in vacuo. The residue was dissolved in THF (60 ml) and was treated with a solution of tetrabutyl ammonium fluoride in THF (1.0 M, 15.95 ml). The mixture was stirred at 20° for 100 min, water (30 ml) was added and the mixture was extracted with $Et_2O$. The extract was washed with water, dried ($Na_2SO_4$) and the solvent evaporated in vacuo to give a residue which was purified by chromatography on a Biotage cartridge (90 g). Elution with EtOAc-petroleum ether (2:3) gave the title compound (2.82 g). LCMS RT=3.01 min ES+ve 370 (MH)$^+$.

vi) 3-[(2-Hydroxyethoxy)methyl]benzonitrile

A solution of ethylene glycol (7.5 g) in DMF (50 ml) under nitrogen at 0° C. was treated portionwise with sodium hydride (1.35 g) and stirred for 0.5 h. 3-Cyanobenzylbromide (4.74 g) was then added and the solution was allowed to warm to room temperature and stirred for 4 h. The solution was then concentrated in vacuo to remove the DMF. The residue was taken up in EtOAc, washed with phosphate buffer (pH=6.5) and water, dried ($MgSO_4$) and concentrated in vacuo. The residue was then purified by chromatography (Biotage, 2×90 g) eluting with 40-60° C. petroleum ether-EtOAc (1:1) to give the title compound (2.62 g). LCMS RT=2.07 min.

vii) Methyl 3-[(2-hydroxyethoxy)methyl]benzoate

A solution of 3-[(2-hydroxyethoxy)methyl]benzonitrile (1 g) in MeOH (20 ml) was treated with conc. $H_2SO_4$ (10 ml) at 0° C. The solution was then allowed to warm to room temperature before heating at reflux for 10 h. Aqueous sodium carbonate was added to neutralise the cooled solution before extracting with EtOAc. The combined organic layers were then washed with water, dried ($MgSO_4$) and concentrated in vacuo. The residue was then purified by chromatography (Biotage, 90 g) eluting with 40°C.-60° C. petroleum ether-EtOAc (3:2) to give the title compound (650 mg). LCMS RT=2.33 min.

viii) Methyl 3-{[2-(4-{2-[(5R)-5-(2,2-dimethyl-4H-1,3-benzodioxin-6-yl)-2-oxo-1,3-oxazolidin-3-yl]ethyl}phenoxy)ethoxy]methyl}benzoate (5R)-5-(2,2-Dimethyl-4H-1,3-benzodioxin-6-yl)-3-[2-(4-hydroxyphenyl)ethyl]-1,3-oxazolidin-2-one{Example 28 v)} (300 mg), methyl 3-[(2-hydroxyethoxy)methyl]benzoate (340 mg) and triphenylphosphine (642 mg) were dissolved in DCM (10 ml) and stirred for 15 min. To this was added 1,1'-(azodicarbonyl)dipiperidine (612 mg) and the solution was stirred for 16 h. The solution was then diluted in DCM, washed with water, dried ($MgSO_4$) and concentrated in vacuo. The residue was purified by chromatography (Biotage, 90 g) eluting with $CH_2Cl_2$-MeOH (250:1) to give the title compound (450 mg). LCMS RT=3.62 min.

ix) 3-{[2-(4-}2-[(5R)-5-(2,2-Dimethyl-4H-1,3-benzodioxin-6-yl)-2-oxo-1,3-oxazolidin-3-yl]ethyl}phenoxy)ethoxy]methyl}benzoic acid Prepared using methods similar to those described in Example 1 x). LCMS RT=3.45 min.

x) 3-{[2-(4-{2-[(5R)-5-(2,2-Dimethyl-4H-1,3-benzodioxin-6-yl)-2-oxo-1,3-oxazolidin-3-yl]ethyl}phenoxy)ethoxy]methyl}-N-isopropylbenzamide A solution of 3-{[2-(4-{2-[(5R)-5-(2,2-dimethyl-4H-1,3-benzodioxin-6-yl)-2-oxo-1,3-oxazolidin-3-yl]ethyl}phenoxy)ethoxy]methyl}benzoic acid (90 mg) and isopropyl amine (9.7 mg) in DMF (2 ml) was cooled to 0° C. and treated with diisopropylethylamine (0.057 ml) and O-benzotriazol-1-yl-N,N,N',N'-tetramethyluronium hexafluorophosphate (HBTU) (62 mg). This was then stirred for 8 h before diluting in EtOAc and washing sequentially with 2M HCl, $NaHCO_3$ (aq) and brine. The combined organic layers were then dried ($MgSO_4$) and concentrated in vacuo to give the title compound(112 mg). LCMS RT=3.36 min.

xi) 3-({2-[4-(2-{[(2R)-2-(2,2-Dimethyl-4H-1,3-benzodioxin-6-yl)-2-hydroxyethyl]amino}ethyl)phenoxy]ethoxy}methyl)-N-isopropylbenzamide Prepared using methods similar to those described in Example 1 xiv). LCMS RT=2.60 min.

xii) 3-[(2-{4-[2-({(2R)-2-Hydroxy-2-[4-hydroxy-3-(hydroxymethyl)phenyl]ethyl}amino)ethyl]phenoxy}ethoxy)methyl]-N-isopropylbenzamide acetate Prepared using methods similar to those described in Example 1 xv). LCMS RT=2.34 min ES+ve 523 (MH)$^+$

EXAMPLE 29

N-Cyclohexyl-3-[(2-{4-[2-({(2R)-2-hydroxy-2-[4-hydroxy-3-(hydroxymethyl)phenyl]ethyl}amino)ethyl]phenoxy}ethoxy)methyl]benzamide acetate i) N-Cylohexyl-3-{[2-(4-{2-[(5R)-5-(2,2-dimethyl-4H-1,3-benzodioxin-6-yl)-2-oxo-1,3-oxazolidin-3-yl]ethyl}phenoxy)ethoxy]methyl}benzamide Prepared using methods similar to those described in Example 28 x). LCMS RT=3.65 min.

ii) N-Cyclohexyl-3-({2-[4-(2-{[(2R)-2-(2,2-dimethyl-4H-1,3-benzodioxin-6-yl)-2-hydroxyethyl]amino}ethyl)phenoxy]ethoxy}methyl)benzamide Prepared using methods similar to those described in Example 1 xiv). LCMS RT=2.78 min.

iii) N-Cyclohexyl-3-[(2-{4-[2-({(2R)-2-hydroxy-2-[4-hydroxy-3-(hydroxymethyl)phenyl]ethyl}amino)ethyl]phenoxy}ethoxy)methyl]benzamide acetate Prepared using methods similar to those described in Example 1 xv). LCMS RT=2.57 min ES+ve 563 (MH)+

EXAMPLE 30

N-Cyclohexyl-3-[(2-{4-[2-({(2R)-2-hydroxy-2-[4-hydroxy-3-(hydroxymethyl)phenyl]ethyl}amino)ethyl]phenoxy}ethoxy)methyl]benzenesulfonamide acetate i) 3-[(Cyclohexylamino)sulfonyl]benzoic acid A mixture of 3-(chlorosulfonyl)benzoic acid (2.00 g) and DCM (20 ml) under nitrogen at 0° was treated with cyclohexylamine (3.63 ml) and the mixture was stirred at 0° C. for 0.5 h. The solvent was evaporated in vacuo and the residue was treated with 1M potassium hydrogen sulfate solution (50 ml) and extracted with EtOAc. The combined extracts were dried (Na$_2$SO$_4$) and the solvent evaporated in vacuo to give the title compound (2.28 g). LCMS RT=3.16 min.

ii) N-Cyclohexyl-3-(hydroxymethyl)benzenesulfonamide

A solution of 3-[(cyclohexylamino)sulfonyl]benzoic acid (2.25 g) in THF (100 ml) under nitrogen at 0° was treated dropwise with 1M borane-THF solution (23.82 ml). The mixture was stirred at 0° C. for 0.5 h and then at 20° C. for 72 h. The mixture was cooled to 0° C. and MeOH (20 ml) was added dropwise. The mixture was stirred for 15 min and then 2N hydrochloric acid (50 ml) was added and the mixture was allowed to warm to 20° C. The bulk of the organic solvents were removed by evaporation in vacuo and the residual aqueous phase was extracted with EtOAc (2×40 ml). The combined extracts were dried (Na$_2$SO$_4$) and the solvent evaporated in vacuo. The residue was purified by SPE on alumina (10 g, activated, neutral, Brockmann 1). Elution with MeOH-dichloromethane (1:20) gave the title compound (1.944 g). LCMS RT 2.95 min.

iii) N-Cyclohexyl-3-(hydroxymethyl)-N-{[2-(trimethylsilyl)ethoxy]methyl}benzenesulfonamide A solution of N-cyclohexyl-3-(hydroxymethyl)benzenesulfonamide (1.744 g) in DMF (30 ml) under nitrogen was treated with sodium hydride (60% dispersion in mineral oil, 311 mg) and the mixture stirred at 20° C. for 0.5 h. 2-(Trimethylsilyl)ethoxymethyl chloride (1.15 ml) was added and the mixture was stirred for a further 2 h at 20° C. Phosphate buffer solution (pH 6.5, 50 ml) and water (50 ml) were added and the mixture was extracted with EtOAc. The combined extracts were washed with water and dried (Na$_2$SO$_4$). Solvent evaporation in vacuo gave a residue which was purified by flash chromatography on silica gel. Elution with EtOAc-petroleum ether (3:7) gave the title compound (1.917 g). LCMS RT=3.83 min.

iv) N-Cyclohexyl-3-{[2-(4-{2-[(5R)-5-(2,2-dimethyl-4H-1,3-benzodioxin-6-yl)-2-oxo-1,3-oxazolidin-3-yl]ethyl}phenoxy)ethoxy]methyl}-N-{[2-(trimethylsilyl)ethoxy]methyl}benzenesulfonamide A solution of N-cyclohexyl-3-(hydroxymethyl)-N-{[2-(trimethylsilyl)ethoxy]methyl}benzenesulfonamide (207 mg) in DMF (5 ml) under nitrogen was treated with sodium hydride (60% dispersion in mineral oil, 24 mg) and the mixture stirred at 20° C. for 15 min. A solution of 2-(4-{2-[(5R)-5-(2,2-dimethyl-4H-1,3-benzodioxin-6-yl)-2-oxo-1,3-oxazolidin-3-yl]ethyl}phenoxy)ethyl methanesulfonate [Example 15 i)] (170 mg) in DMF (3 ml) was added and the mixture stirred at 20° C. for 18 h. Phosphate buffer solution (pH 6.5, 15 ml) and water (15 ml) were added and the mixture was extracted with EtOAc. The combined extracts were washed with water and dried (Na$_2$SO$_4$). Solvent evaporation in vacuo gave a residue which was purified by "Flashmaster" chromatography on silica gel. Elution with EtOAc-cyclohexane (2:3) gave the title compound (125 mg). LCMS RT=4.35 min.

v) N-Cyclohexyl-3-({2-[4-(2-{[(2R)-2-(2,2-Dimethyl-4H-1,3-benzodioxin-6-yl)-2-hydroxyethyl]amino}ethyl)phenoxy]ethoxy}methyl)-N-{[2-(trimethylsilyl)ethoxy]methyl}benzenesulfonamide Prepared using methods similar to those described in Example 1 xiv. LCMS RT=3.52 min.

vi) N-Cyclohexyl-3-[(2-{4-[2-({(2R)-2-hydroxy-2-[4-hydroxy-3-(hydroxymethyl)phenyl]ethyl}amino)ethyl]phenoxy}ethoxy)methyl]benzenesulfonamide acetate Prepared using methods similar to those described in Example 1 xv. LCMS RT=2.66 min; ES+ve 599 (MH)+.

EXAMPLE 31

3-[(2-{4-[2-({(2R)-2-Hydroxy-2-[4-hydroxy-3-(hydroxymethyl)phenyl]ethyl}amino) ethyl]phenoxy}ethoxy)methyl]-N-methylbenzenesulfonamide acetate i) 3-[(Methylamino)sulfonyl]benzoic acid Prepared using methods similar to those described in Example 30 i). LCMS RT=2.14 min.

ii) 3-(Hydroxymethyl)-N-methylbenzenesulfonamide

Prepared using methods similar to those described in Example 30 ii). LCMS RT=1.86 min.

iii) 3-(Hydroxymethyl)-N-methyl-N-{[2-(trimethylsilyl)ethoxy]methyl}benzenesulfonamide Prepared using methods similar to those described in Example 30 iii) LCMS RT=3.50 min.

iv) 3-{[2-(4-{2-[(5R)-5-(2,2-Dimethyl-4H-1,3-benzodioxin-6-yl)-2oxo-1,3-oxazolidin-3-yl]ethyl}phenoxy)ethoxy]methyl}-N-methyl-N-{[2-(trimethylsilyl)ethoxy]methyl}benzenesulfonamide Prepared using methods similar to those described in Example 30 iv). LCMS RT=3.98 min.

v) 3-({2-[4-(2-{[(2R)-2-(2,2-Dimethyl-4H-1,3-benzodioxin-6-yl)-2-hydroxyethyl]amino}ethyl)phenoxy]ethoxy}methyl)-N-methyl-N-{[2-(trimethylsilyl)ethoxy]methyl}benzenesulfonamide Prepared using methods similar to those described in Example 1 xiv. LCMS RT=3.21 min.

vi) 3-[(2-{4-[2-({(2R)-2-Hydroxy-2-[4-hydroxy-3-(hydroxymethyl)phenyl]ethyl}amino)ethyl]phenoxy}ethoxy)methyl]-N-methylbenzenesulfonamide acetate Prepared using methods similar to those described in Example 1 xv. LCMS RT=2.29 min, ES+ve 531 (MH)+.

EXAMPLE 32

4-[(1R)-1-Hydroxy-2-({2-[4-(2-{[3-(isopropylsulfinyl)benzyl]oxy}ethoxy)phenyl]ethyl}amino)ethyl]-2-(hydroxymethyl)phenol acetate i) [3-(Isopropylthio)phenyl]methanol 3-Iodobenzylalcohol (1.40 g) was stirred with tris(dibenzylideneacetone)dipalladium (0.08 g) and 1,1'-bis(diphenylphosphino)ferrocene (0.09 g) in N-methylpyrrolidone (20 ml) and triethylamine (10 ml) at 21° for 10 min while sparging with nitrogen. i-Propyl mercaptan (0.83 ml) was added and the mixture was heated to 60° C. for 2 h. The mixture was partitioned between diethyl ether and water and the aqueous layer was extracted with more diethyl ether. The combined organic layers were washed with brine, dried (MgSO$_4$) and the volatiles were distilled off on a steam bath. The residue was chromatographed on silica gel (50 g) in diethyl ether-petroleum ether (40-60° C.)(1:9, and then 1:4) to give the title compound (0.973 g). LCMS RT=2.93 min.

ii) 1-(Bromomethyl)-3-(isopropylthio)benzene [3-(Isopropylthio)phenyl]methanol (0.365 g) was stirred with phosphorus tribromide (0.19 ml) in dichloromethane (10 ml) at 21° C. for 2 h. The solution was washed with water plus sodium bicarbonate and the aqueous layer was back extracted with dichloromethane. The combined organic layers were washed with water, dried (MgSO$_4$) and evaporated to give the title compound (0.226 g). LCMS RT=3.64 min.

iii) (5R)-5-(2,2-Dimethyl-4H-1,3-benzodioxin-6-yl)-3-[2-[4-(2-{[3-(isopropylthio)benzyl]oxy}ethoxy)phenyl]ethyl}-1,3-oxazolidin-2-one Prepared using methods similar to those described in Example 1 xi). LCMS RT=3.89 min.

iv) (5R)-5(2,2-Dimethyl-4H-1,3-benzodioxin-6-yl)-3-{2-[4-(2-{[3-(isopropylsulfinyl)benzyl]oxy}ethoxy)phenyl]ethyl}-1,3-oxazolidin-2-one Prepared using methods similar to those described in Example 24 ii). LCMS RT=3.29 min.

v) (1R)-1-(2,2-Dimethyl-4H-1,3-benzodioxin-6-yl)-2-({2-[4-(2-{[3-(isopropylsulfinyl)benzyl]oxy}ethoxy)phenyl]ethyl}amino)ethanol (5R)-5-(2,2-Dimethyl-4H-1,3-benzodioxin-6-yl)-3-{2-[4-(2-{[3-(isopropylsulfinyl)benzyl]oxy}ethoxy)phenyl]ethyl}-1,3-oxazolidin-2-one (0.07 g) was stirred with potassium trimethylsilanolate (0.14 g) in THF (5 ml) under reflux for 2.5 h. After cooling the mixture was diluted with dichloromethane and poured onto a 10 g Bond Elut silica cartridge which was eluted successively with dichloromethane, then dichloromethane:ethanol:0.880 ammonia solution (100:8:1 and then 50:8:1) to give the title compound (0.031 g). LCMS RT=2.61 min.

vi) 4-[(1R)-1-Hydroxy-2-({2-[4-(2-{[3-(isopropylsulfinyl)benzyl]oxy}ethoxy)phenyl]ethyl}amino)ethyl]-2-(hydroxymethyl)phenol acetate Prepared using methods similar to those described in Example 1 xv). LCMS RT=2.26 min ES+ve 528 (MH)$^+$

EXAMPLE 33

4-[(1R)-1-Hydroxy-2-({2-[4-(2-{[3-(isopropylsulfonyl)benzyl]oxy}ethoxy)phenyl]ethyl}amino)ethyl]-2-(hydroxymethyl)phenol acetate i) (5R)-5-(2,2-Dimethyl-4H-1,3-benzodioxin-6-yl)-3-{2-[4-(2-{[3-(isopropylsulfonyl)benzyl]oxy}ethoxy)phenyl]ethyl}-1,3-oxazolidin-2-one Prepared using methods similar to those described in Example 24 iii). LCMS RT=3.43 min ii) (1R)-1-(2,2-Dimethyl-4H-1,3-benzodioxin-6-yl)-2-({2-[4-(2-{[3-(isopropylsulfonyl)benzyl]oxy}ethoxy)phenyl]ethyl}amino)ethanol Prepared using methods similar to those described in Example 32 v). LCMS RT=2.63 min iii) 4-[(1R)-1-Hydroxy-2-({2-[4-(2-{[3-(isopropylsulfonyl)benzyl]oxy}ethoxy)phenyl]ethyl}amino)ethyl]-2-(hydroxymethyl)phenol acetate Prepared using methods similar to those described in Example 1 xv). LCMS RT=2.33 min ES+ve 545 (MH)$^+$

EXAMPLE 34

2-(Hydroxymethyl)-4-[(1R)-1-hydroxy-2-({2-[4-(4-phenylbutoxy)phenyl]ethyl}amino)ethyl]phenol acetate i) 1-(2-Bromoethyl)-4-(4-phenylbutoxy)benzene A solution of 2-[4-(4-phenylbutoxy)phenyl]ethanol (120 mg) and carbon tetrabromide (250 mg) in DCM (7 ml) under nitrogen was treated with triphenylphosphine (175 mg), the mixture was stirred at 20° for 18 h and the mixture was then applied to an SPE cartridge (5 g). Elution with DCM gave an oil which was further purified by flash chromatography on silica gel. Elution with Et$_2$O-petroleum ether (1:20) gave the title compound (1.917 g). LCMS RT=4.06 min.

ii)(5R)-5-(2,2-Dimethyl-4H-1,3-benzodioxin-6-yl)-3-{2-[4-(4-phenylbutoxy)phenyl]ethyl}-1,3-oxazolidin-2-one A solution of (5R)-5-(2,2-dimethyl-4H-1,3-benzodioxin-6-yl)-1,3-oxazolidin-2-one (82 mg) in DMF under nitrogen was treated with sodium hydride (60% dispersion in mineral oil, 16 mg) and the mixture stirred at 20□ for 10 min. A solution of 1-(2-bromoethyl)-4-(4-phenylbutoxy)benzene (110 mg) in DMF (1 ml) was added and the mixture was stirred at 20° C. for 2 h. Phosphate buffer solution (pH 6.5, 10 ml) and water (20 ml) were added and the mixture was extracted with EtOAc. The combined extracts were washed with water and dried (Na$_2$SO$_4$). Solvent evaporation in vacuo gave a residue which was partially purified by SPE (5 g). Elution with DCM then EtOAC-cyclohexane (1:1) gave material which was further purified by flash chromatography on silica gel. Elution with EtOAc-petroleum ether (3:2) gave the title compound (75 g). LCMS RT=3.92 min.

iii)(1R)-1-(2,2-Dimethyl-4H-1,3-benzodioxin-6-yl)-2-({2-[4-(4-phenylbutoxy)phenyl]ethyl}amino)ethanol Prepared using methods similar to those described in Example 1 xiv. LCMS RT=2.99 min.

iv)2-(Hydroxymethyl)-4-[(1R)-1-hydroxy-2-({2-[4-(4-phenylbutoxy)phenyl]ethyl}amino)ethyl]phenol acetate Prepared using methods similar to those described in Example 1xv. LCMS RT-=2.84 min. ES+ve 436 (MH)$^+$.

EXAMPLE 35

4-{(1R)-1-Hydroxy-2-[(2-{4-[4-(3-hydroxyphenyl)butoxy]phenyl}ethyl)amino]ethyl}-2-(hydroxymethyl)phenol acetate i) 3-(4-Hydroxybut-1-ynyl)phenyl acetate A solution of 3-iodophenyl acetate (5.6 g) (*J. Org. Chem.* 1983, 48,1542-4) in acetonitrile (100 mL) was treated with (Ph$_3$P)$_2$PdCl$_2$ (673 mg) and CuI (368 mg) and stirred at room temperature. 3-Butyn-1-ol (1.78 g) was added and the reaction mixture stirred for a further 20 h and concentrated in vacuo. The residue was purified by chromatography (SPE, gradient from cyclohexane to DCM) to give the title compound. LCMS RT=2.54 min ii) 3-(4-Hydroxybutyl)phenyl acetate A solution of 3-(4-hydroxybut-1-ynyl)phenyl acetate (4.47 g) was hydrogenated over 5% Pd on carbon in ethyl acetate (100 mL) and ethanol (100 mL) over 20 h. The reaction mixture was filtered through celite under nitrogen, and the filtrate was concentrated in vacua. The residue was purified by chromatography (SPE, gradient from cyclohexane to EtOAc) to give the title compound. LCMS RT=2.64 min iii) 3-(4-Bromobutyl)phenyl acetate A solution of 3-(4-hydroxybutyl)phenyl acetate (416 mg) in DCM (10 mL) was treated with carbon tetrabromide (1.16 g) and triphenylphosphine (791 mg) and stirred at room temperature for 15 min prior to concentration in vacuo. The residue was purified by chromatography (SPE, DCM-petrol 1:1) to give the title compound. LCMS RT=3.58 min iv) 3-[4-(4-{2-[(5R)-5-(2,2-Dimethyl-4H-1,3-benzodioxin-6-yl)-2-oxo-1,3-oxazolidin-3-yl]ethyl}phenoxy)butyl]phenyl acetate A solution of (5R)-5-(2,2-dimethyl-4H-1,3-benzodioxin-6-yl)-3-[2-(4-hydroxyphenyl)ethyl]-1,3-oxazolidin-2-one (Example 28 v) (37 mg) in dry DMF (0.4 mL) was treated with caesium carbonate (65 mg) and 3-(4bromobutyl)phenyl acetate (0.2 mmol) as a solution in DMF (0.5 mL). Further DMF was added (1 mL) and the reaction mixture stirred at 50° C. for 24 h. The reaction mixture was cooled to room temperature and concentrated in vacuo in a genevac. The residue was suspended in chloroform and filtered to remove inorganic salts. The filtrate was added to the top of a pre-conditioned $NH_2$ propyl cartridge (1 g). The cartridge was washed with chloroform and methanol and the title compound eluted with 2M $NH_3$-MeOH. LCMS RT=3.86 min v) 4-{(1R)-1-Hydroxy-2-[(2-{4-]4-(3-hydroxyphenyl)butoxy]phenyl}amino]ethyl}-2-(hydroxymethyl)phenol acetate Prepared using methods similar to those described in Example 3 ii). LCMS RT=3.81 min; ES+ve m/z451 (MH)+

EXAMPLE 36

4-((1R)-2-{[2-(4-{4-[3-(Cyclopentylsulfinyl)phenyl]butoxy}phenyl)ethyl]amino}-1-hydroxyethyl)-2-(hydroxymethyl)phenol acetate i) [4-(3-Bromophenyl)butoxy](tert-butyl)diphenylsilane A solution of 4-(3-bromophenyl)butan-1-ol (5 g) (WO 0266422 A1) in dry DMF was treated with imidazole (1.8 g) and tert-butyldiphenylsilyl chloride (7.2 g) and stirred at room temperature for 16 h. The reaction mixture was partitioned between water and EtOAc. The organic phase was washed with 2M HCl, water, sat. $NH_4Cl(aq)$, water, dried ($MgSO_4$) and concentrated in vacuo. The residue was purified by chromatography (SPE, Gradient between cyclohexane and cyclohexane-EtOAc (5:1) to give the title compound. LCMS RT=4.82 min ii) tert-Butyl{4-[3-(cyclopentylthio)phenyl]butoxy}diphenylsilane Prepared using methods similar to those described for Example 24 i). LCMS RT=4.94 min.

iii) tert-Butyl{4-[3-(cyclopentylsulfinyl)phenyl]butoxy}diphenylsilane

Prepared by methods similar to those described for Example 24 ii. LCMS RT=4.45 min.

iv) 4-[3-(Cyclopentylsulfinyl)phenyl]butan-1-ol

A solution of tert-butyl{4-[3-(cyclopentylsulfinyl)phenyl]butoxy}diphenylsilane (690 mg) in dry THF (10 ml) was treated with a solution of tetra-n-butylammonium fluoride in THF (1M; 3 ml) and the resultant reaction mixture stirred at room temperature for 5 h prior to concentration in vacuo. The residue was purified by chromatography (SPE, Gradient between cyclohexane and EtOAc) to give the title compound. LCMS RT=2.64 min.

v) 1-(4-Bromobutyl)-3-(cyclopentylsulfinyl)benzene

Prepared by methods similar to those described for Example 35 iii). LCMS RT=3.48 min.

vi) (5R)-3-[2-(4-{4-[3-(Cyclopentylsulfinyl)phenyl]butoxy}phenyl)ethyl]-5-(2.2dimethyl-4H-1,3-benzodioxin-6-yl)-1,3-oxazolidin-2-one Prepared by methods similar to those described for Example 35 iv). LCMS RT=3.81 min.

vii) 4-((1R)-2-{[2-(4-{4-[3-(Cyclopentylsulfinyl)phenyl]butoxy}phenyl)ethyl]amino}-1-hydroxyethyl)-2-(hydroxymethyl)phenol acetate Prepared by methods similar to those described for Example 3 ii). LCMS RT=2.74 min. ES+ve m/z 552 (MH)+

EXAMPLE 37

4-{(1R)-2-[(2-{4-[4-(2,6-Dichlorophenyl)butoxy]phenyl]ethyl)amino]-1-hydroxyethyl}-2-(hydroxymethyl)phenol acetate i) 4-(2,6-Dichlorophenyl)but-3-yn-1-ol Prepared by methods similar to those described for Example 35 i). LCMS RT=3.06 min.

ii) 4-(2,6-Dichlorophenyl)butan-1-ol

Prepared by methods similar to those described for Example 35 ii) LCMS RT=3.22 min.

iii) 2-(4-Bromobutyl)-1,3-dichlorobenzene

Prepared by methods similar to those described for Example 35 iii) LCMS RT=4.17 min.

iv) (5R)-3-(2-{4-[4-(2,6-Dichlorophenyl)butoxy]phenyl}ethyl)-5-(2,2-dimethyl-4H-1,3-benzodioxin-6-yl)-1,3-oxazolidin-2-one Prepared by methods similar to those described for Example 35 iv) LCMS RT=4.26 min.

v) 4-{(1R)-2-[(2-{4-[4-(2,6-Dichlorophenyl)butoxy]phenyl}ethyl)amino]-1-hydroxyethyl}-2-(hydroxymethyl)phenol acetate Prepared by methods similar to those described for Example 3 ii). LCMS RT=3.00 min. ES+ve m/z 504 (MH)+

EXAMPLE 38

3-(4-{4-[2-({(2R)-2-Hydroxy-2-[4-hydroxy-3-(hydroxymethyl)phenyl]ethyl}amino)ethyl]phenoxy}butyl)benzenesulfonamide acetate i) 3-(4-Hydroxybut-1-ynyl)benzenesulfonamide Prepared by methods similar to those described for Example 35 i) LCMS RT=2.17 min.

ii) 3-(4-Hydroxybutyl)benzenesulfonamide

Prepared by methods similar to those described for Example 35 ii) LCMS RT=2.14 min.

iii) 4-[3-(Aminosulfonyl)phenyl]butyl methanesulfonate

A solution of 3-(4-hydroxybutyl)benzenesulfonamide (458 mg) in dry THF (10 ml) was treated with triethylamine (0.307 ml) and the resultant solution cooled to 0° C. Methanesulfonyl chloride (0.17 ml) was added dropwise. The mixture was allowed to warm to room temperature and stirred for a further 15 minutes. The reaction mixture was partitioned between 1M HCl$_{aq}$ and EtOAc. The aqueous phase was washed with EtOAc. The combined organic phase was dried (MgSO$_4$) and concentrated in vacuo to give the title compound LCMS RT=2.67 min.

iv) 3-[4-(4-{2-[(5R)-5-(2,2-Dimethyl-4H-1,3-benzodioxin-6-yl)-2-oxo-1,3-oxazolidin-3-yl]ethyl]phenoxy)butyl]benzenesulfonamide Prepared by methods similar to those described for Example 35 iv) LCMS RT=3.56 min.

v) 3-(4-{4-[2-({(2R)-2-Hydroxy-2-[4-hydroxy-3-(hydroxymethyl)phenyl]ethyl}amino)ethyl]phenoxy}butyl)benzenesulfonamide acetate Prepared by methods similar to those described for Example 1 xv) LCMS RT=2.21 min. ES+ve m/z 515 (MH)$^+$

EXAMPLE 39

N-[3-(4-{4-[2-({(2R)-2-Hydroxy-2-[4-hydroxy-3-(hydroxymethyl)phenyl]ethyl}amino)ethyl]phenoxy}butyl)phenyl]urea acetate i) 3-(4-{[tert-Butyl(dimethyl)silyl]oxy}butyl)aniline A solution of the 4-(3-aminophenyl)butan-1-ol [Hua Hsueh Hsueh Pao 1964, 30, 166-75. CAN 61:47615] (3.66 g) in dry DMF (30 ml) was treated with imidazole (1.66 g) and tert-butyldimethylsilyl chloride (3.5 g). The reaction mixture was stirred at room temperature for 18 h. The reaction mixture was concentrated in vacuo and the residue partitioned between sat. NH$_4$Cl$_{(aq)}$ and ethyl acetate. The aqueous phase was extracted with EtOAc and the combined organic phase washed with water, dried (Na$_2$SO$_4$) and concentrated in vacuo. The residue was purified by chromatography (Biotage, Petroleum ether-EtOAc 9:1) to give the title compound. LCMS RT=3.89 min.

ii) N-[3-(4-{[tert-Butyl(dimethyl)silyl]oxy}butyl)phenyl]urea

A solution of 3-(4-{[tert-butyl(dimethyl)silyl]oxy}butyl)aniline (5.16 g) in dry DCM (50 ml) was treated dropwise with a solution of trichloroacetyl isocyanate (2.36 ml) in dry DCM (6 ml) over 10 min. The reaction mixture was stirred at room temperature for 10 min prior to addition of 2M NaOH (50 ml). The reaction mixture was stirred at 70° C. for 5 h and room temperature for 16 h. The aqueous phase was extracted with DCM and the combined organic layers washed with water and concentrated in vacuo. The residue was purified by chromatography (biotage, EtOAc-Petrol 2:1) to give the title compound. LCMS RT=3.78 min.

iii) N-[3-(4-hydroxybutyl)phenyl]urea

A solution of N-[3-(4-{[tert-butyl(dimethyl)silyl]oxy}butyl)phenyl]urea (5.67 g) in THF (50 ml) was treated with TFA (13.56 ml) and stirred at room temperature for 1 h. Further TFA (5 ml) was added and the reaction mixture stirred for a further 16 hours. The reaction mixture was concentrated in vacuo. The residue was co-evaporated with methanol and then suspended in methanol and heated at reflux for 20 h prior to concentration in vacuo. The residue was purified by chromatography (SPE, DCM-MeOH 9:1) to give the title compound. LCMS RT=2.14 min.

iv) 4-{3-[(Aminocarbonyl)amino]phenyl}butyl methanesulfonate

Prepared by methods similar to those described for Example 38 iii). LCMS RT=2.65 min.

v) N-{3-[4-(4-{2-[(5R)-5-(2,2-Dimethyl-4H-1,3-benzodioxin-6-yl)-2-oxo-1,3-oxazolidin-3-yl]ethyl}phenoxy)butyl]phenyl}urea Prepared by methods similar to those described for Example 35 iv). LCMS RT=3.56 min.

vi) N-[3-(4-{4-[2-({(2R)-2-Hydroxy-2-[4-hydroxy-3-(hydroxymethyl)phenyl]ethyl}amino)ethyl]phenoxy}butyl)phenyl]urea acetate Prepared by methods similar to those described for Example 3 ii) LCMS RT=2.23 min. ES+ve m/z 494 (MH)$^+$

EXAMPLE 40

3-(4-{4-[2-({(2R)-2-Hydroxy-2-[4-hydroxy-3-(hydroxymethyl)phenyl]ethyl}amino)ethyl]phenoxy}butyl)benzoic acid acetate i) 3-(4-Hydroxybut-1-ynyl)benzoic acid Prepared by methods similar to those described for Example 35 i) LCMS RT=2.48 min.

ii) 3-(4-Hydroxybutyl)benzoic acid

Prepared by methods similar to those described for Example 35 ii). LCMS RT=2.48 min.

iii) Benzyl 3-(4-hydroxybutyl)benzoate

A solution of 3-(4-hydroxybutyl)benzoic acid (100 mg) in dry DMF (10 ml) was treated with diisopropylethylamine (0.134 ml) and benzyl bromide (106 mg) and the reaction mixture was stirred for 65 h. The reaction mixture was partitioned between EtOAc and water. The organic phase was washed with sat. NH$_4$Cl$_{(aq)}$, dried (MgSO$_4$) and concentrated in vacuo. The residue was purified by chromatography (SPE, gradient Cyclohexane to cyclohexane-EtOAc 1:1) to give the title compound LCMS RT=3.38 min.

iv) Benzyl 3-(4-bromobutyl)benzoate

Prepared by methods similar to those described for Example 35 iii) LCMS RT=4.01 min.

v) Benzyl 3-[4-(4-{2-[(5R)-5-(2,2dimethyl-4H-1,3-benzodioxin-6-yl)-2-oxo-1,3-oxazolidin-3-yl]ethyl}phenoxy)butyl]benzoate Prepared by methods similar to those described for Example 35 iv) LCMS RT=4.10 min.

vi) 3-{4-[4-(2-{[(2R)-2-(2,2-Dimethyl-4H-1,3-benzodioxin-6-yl)-2-hydroxyethyl]amino}ethyl)phenoxy]butyl}benzoic acid Prepared by methods similar to those described for Example 1 xiv). LCMS RT=2.89 min.

vii) 3-(4-{4-[2-({(2R)-2-Hydroxy-2-[4-hydroxy-3-(hydroxymethyl)phenyl]ethyl}amino)ethyl]phenoxy}butyl)benzoic acid acetate Prepared by methods similar to those described for Example 1 xv). LCMS RT=2.58 min; ES+ve m/z 479 (MH)$^+$

EXAMPLE 41

3-(4-{4-[2-({(2R)-2-Hydroxy-2-[4-hydroxy-3-(hydroxymethyl)phenyl]ethyl}amino)ethyl]phenoxy}butyl)benzonitrile acetate i) 3-(4-Bromobutyl)benzonitrile Prepared by methods similar to those described for Example 35iii) from 3-(4-hydroxybutyl)benzonitrile [Hua Hsueh Hsueh Pao 1964, 30, 166-75. CAN 61:47615] LCMS RT=3.50 min.

ii) 3-[4-(4-{2-[(5R)-5-(2,2-Dimethyl-4H-1,3-benzodioxin-6-yl)-2-oxo-1,3-oxazolidin-3-yl]ethyl}phenoxy)butyl]benzonitrile Prepared by methods similar to those described for Example 35 iv) LCMS RT=3.74 min.

iii) 3-{4-[4-(2-{[(2R)-2-(2,2-Dimethyl-4H-1,3-benzodioxin-6-yl)-2-hydroxyethyl]amino}ethyl)phenoxy]butyl}benzonitrile Prepared by methods similar to those described for Example 1 xiv). LCMS RT=2.86 min.

iv) 3-(4-{4-[2-({(2R)-2-Hydroxy-2-[4-hydroxy-3-(hydroxymethyl)phenyl]ethyl}amino)ethyl]phenoxy}butyl)benzonitrile acetate Prepared by methods similar to those described for Example 1 xv). LCMS RT=2.64 min; ES+ve m/z 461 (MH)+

EXAMPLE 42

3-(4-{4-[2-({(2R)-2-Hydroxy-2-[4-hydroxy-3-(hydroxymethyl)phenyl]ethyl}amino)ethyl]phenoxy}butyl)benzamide acetate i) 3-{4-[4-(2-{[(2R)-2-(2,2-Dimethyl-4H-1,3-benzodioxin-6-yl)-2-hydroxyethyl]amino}ethyl)phenoxy]butyl}benzamide Prepared by methods similar to those described for Example 10 ii). LCMS RT=2.63 min.

ii) 3-(4-{4-[2-({(2R)-2-Hydroxy-2-[4-hydroxy-3-(hydroxymethyl)phenyl]ethyl}amino)ethyl]phenoxy}butyl)benzamide acetate Prepared by methods similar to those described for Example 1 xv) LCMS RT=2.34 min; ES+ve m/z 479 (MH)+

EXAMPLE 43

3'-](2-{4-[2-({(2R)-2-Hydroxy-2-[4-hydroxy-3-(hydroxymethyl)phenyl]ethyl}amino)ethyl]phenoxy}ethoxy)methyl]-1,1'-biphenyl-3-carboxylic acid acetate i) Methyl 3'-{[2-(4-{2-[(5R)-5-(2,2-dimethyl-4H-1,3-benzodioxin-6yl)-2-oxo-1,3-oxazolidin-3-yl]ethyl}phenoxy)ethoxy]methyl}-1,1'-biphenyl-3-carboxylate A mixture of (5R)-5-(2,2-dimethyl-4H-1,3-benzodioxin-6-yl)-3-[2-(4-{2-[(3-iodobenzyl)oxy]ethoxy}phenyl)ethyl]-1,3-oxazolidin-2-one {Example 6 i)} (150 mg), 3-(methoxycarbonyl)phenylboronic acid (47 mg), tetrakis(triphenylphosphine)palladium (0) (6 mg) and 2N sodium carbonate (7 mL) in dimethoxyethane (10 mL) was heated at 85° C. for 1 h. The solution was then diluted in EtOAc, washed with water, dried (MgSO$_4$) and concentrated in vacuo. The residue was purified by chromatography (Biotage, 40 g) eluting with CH$_2$Cl$_2$-MeOH (200:1) to give the title compound (128 mg). LCMS RT=3.99 min.

ii) 3'-({2-[4-(2-{[(2R)-2-(2,2-Dimethyl-4H-1,3-benzodioxin-6-yl)-2-hydroxyethyl]amino}ethyl)phenoxy]ethoxy]methyl)-1,1'-biphenyl-3-carboxylic acid Prepared using methods similar to those described in Example 1 xiv) LCMS RT=2.92 min.

iii) 3'-[(2-{4-[2-({(2R)-2-Hydroxy-2-[4-hydroxy-3-(hydroxymethyl)phenyl]ethyl}amino)ethyl]phenoxy}ethoxy)methyl]-1,1'-biphenyl-3-carboxylic acid acetate Prepared using methods similar to those described in Example 1 xv) LCMS RT=2.78 min, ES+ve 558 (MH)+

EXAMPLE 44

N-Butyl-3-[(2-{4-[2-({(2R)-2-hydroxy-2-[4-hydroxy-3-(hydroxymethyl)phenyl]ethyl}amino)ethyl]phenoxy}ethoxy)methyl]benzamide acetate i) N-Butyl-3-{[2-(4-{2-[(5R)-5-(2,2-dimethyl-4H-1,3-benzodioxin-6-yl)-2-oxo-1,3-oxazolidin-3-yl]ethyl}phenoxy)ethoxy]methyl}benzamide Prepared using methods similar to those described in Example 28 x). LCMS RT=3.42 min ii) N-Butyl-3-({2-[4-(2-{[(2R)-2-(2,2-dimethyl-4H-1,3-benzodioxin-6-yl)-2-hydroxyethyl]amino}ethyl)phenoxy]ethoxy}methyl)benzamide Prepared using methods similar to those described in Example 1 xiv). LCMS RT=2.65 min iii) N-Butyl-3-[(2-{4-[2-({(2R)-2-hydroxy-2-[4-hydroxy-3-(hydroxymethyl)phenyl]ethyl}amino)ethyl]phenoxy}ethoxy)methyl]benzamide acetate Prepared using methods similar to those described in Example 1 xv). LCMS RT=2.41 min ES+ve 537 (MH)+

EXAMPLE 45

3-[(2-{4-[2-({(2R)-2-Hydroxy-2-[4-hydroxy-3-(hydroxymethyl)phenyl]ethyl}amino)ethyl]phenoxy}ethoxy)methyl]-N-pentylbenzamide acetate i) 3-{[2-(4-{2-[(5R)-5-(2,2-Dimethyl-4H-1,3-benzodioxin-6-yl)-2-oxo-1,3-oxazolidin-3-yl]ethyl}phenoxy)ethoxy]methyl}-N-pentylbenzamide Prepared using methods similar to those described in Example 28 x). LCMS RT=3.55 min ii) 3-({2-[4-(2-{[(2R)-2-(2,2-Dimethyl-4H-1,3-benzodioxin-6-yl)-2-hydroxyethyl]amino}ethyl)phenoxy]ethoxy}methyl)-N-pentlbenzamide Prepared using methods similar to those described in Example 1 xiv) LCMS RT=2.76 min iii) 3-[(2-{4-[2-({(2R)-2-Hydroxy-2-[4-hydroxy-3-(hydroxymethyl)phenyl]ethyl}amino)ethyl]phenoxy}ethoxy)methyl]-N-pentylbenzamide acetate Prepared using methods similar to those described in Example 1 xv). LCMS RT=2.51 min ES+ve 551 (MH)+

EXAMPLE 46

3-[(2-{4-[2-({(2R)-2-Hydroxy-2-[4-hydroxy-3-(hydroxymethyl)phenyl]ethyl}amino)ethyl]phenoxy}ethoxy)methyl]-N-isobutylbenzamide acetate i) 3-{[2-(4-[2-[(5R)-5-(2,2-Dimethyl-4H-1,3-benzodioxin-6-yl)-2-oxo-1,3-oxazolidin-3-yl]ethyl}phenoxy)ethoxy]methyl}-N-isobutyl]benzamide Prepared using methods similar to those described in Example 28 x). LCMS RT=3.42 min ii) 3-({2-[4-(2-{[(2R)-2-(2,2-Dimethyl-4H-1,3-benzodioxin-6-yl)-2-hydroxyethyl]amino}ethyl)phenoxy]ethoxy}methyl)-N-isobutylbenzamide Prepared using methods similar to those described in Example 1 xiv) LCMS RT=2.72 min iii) 3-[(2-{4-[2-({(2R)-2-Hydroxy-2-[4-hydroxy-3-(hydroxymethyl)phenyl]ethyl}amino)ethyl]phenoxy}ethoxy)methyl]-N-isobutylbenzamide acetate Prepared using methods similar to those described in Example 1 xv). LCMS RT=2.38 min ES+ve 537 (MH)+

EXAMPLE 47

3-[(2-{4-[2-({(2R)-2-Hydroxy-2-[4-hydroxy-3-(hydroxymethyl)phenyl]ethyl}amino)ethyl]phenoxy}ethoxy)methyl]-N-isopentylbenzamide acetate i) 3-{[2-(4-[2-[(5R)-5-(2,2-Dimethyl-4H-1,3-benzodioxin-6-yl)-2-oxo-1,3-oxazolidin-3-yl]ethyl}phenoxy)ethoxy]methyl}-N-isopentylbenzamide Prepared using methods similar to those described in Example 28 x). LCMS RT=3.52 min ii) 3-({2-[4-(2-{[(2R)-2-(2,2-Dimethyl-4H-1,3-benzodioxin-6-yl)-2-hydroxyethyl]amino}ethyl)phenoxy]ethoxy}methyl)-N-isopentylbenzamide Prepared using methods similar to those described in Example 1 xiv). LCMS RT=2.78 min iii) 3-[(2-{4-[2-({(2R)-2-Hydroxy-2-[4-hydroxy-3-(hydroxymethyl)phenyl]ethyl}amino)ethyl]phenoxy}ethoxy)methyl]-N-isopentylbenzamide acetate Prepared using methods similar to those described in Example 1 xv). LCMS RT=2.52 min ES+ve 551 (MH)+

EXAMPLE 48

3-[(2-{4-[2-({(2R)-2-Hydroxy-2-[4-hydroxy-3-(hydroxymethyl)phenyl]ethyl}amino)ethyl]phenoxy}ethoxy)methyl]benzamide i) 2-[(3-Cyanobenzyl)oxy]ethyl methanesulfonate To a solution of 3-[(2-hydroxyethoxy)methyl]benzonitrile (example 28vi) (6.00 g) and diisopropylethylamine (11.8 ml) in dichloromethane (100 ml) at 0° C. was added methanesulphonyl chloride (3.14 ml) dropwise and the mixture allowed to stir for 2 h. The resultant mixture was partitioned between dichloromethane and saturated sodium hydrogen carbonate. The organic phase was dried (MgSO$_4$) and concentrated in vacuo to give the title compound (8.5 g). LCMS RT=2.58 min.

ii) 3-[(2-Bromoethoxy)methyl]benzonitrile

A mixture of 2-[(3-cyanobenzyl)oxy]ethyl methanesulfonate (6.83 g) and tetrabutylammonium bromide (17.2 g) in acetonitrile (250 ml) was heated at 50° C. for 18 h. Further tetrabutylammonium bromide (5.00 g) was added and the mixture heated at 50° C. for 7 h. The solvent was removed in vacuo and the residue partitioned between ethyl acetate and water. The organic phase was washed with brine, dried (MgSO$_4$), and concentrated in vacuo to give the title compound (5.51 g). LCMS RT=3.05 min.

iii) 3-({2-[4-(2-Hydroxyethyl)phenoxy]ethoxy}methyl)benzonitrile

A mixture of 3-[(2-bromoethoxy)methyl]benzonitrile (5.00 g), 2-(4-hydroxyphenyl)ethanol (3.45 g), and potassium carbonate (5.76 g) in N,N-dimethylformamide (30 ml) was heated at 60° C. for 66 h. The mixture was allowed to cool and partitioned between ethyl acetate and 2N HCl. The aqueous phase was extracted with ethyl acetate and the combined organic phase washed with 2N NaOH, brine, dried (MgSO$_4$) and concentrated in vacuo. The residue was purified by chromatography (SPE, eluted with gradient between cyclohexane and 80% EtOAc in cyclohexane) to give the title compound (5.05 g). LCMS RT=2.96 min.

iv) 2-(4-{2-[(3-Cyanobenzyl)oxy]ethoxy}phenyl)ethyl methanesulfonate

To a solution of 3-({2-[4-(2-hydroxyethyl)phenoxy]ethoxy}methyl)benzonitrile (5.04 g) and diisopropylethylamine (5.94 ml) in dichloromethane (50 ml) at 0° C. was added methanesulphonyl chloride (1.58 ml) dropwise and the mixture allowed to stir for 2 h. The resultant mixture was partitioned between dichloromethane and saturated sodium hydrogen carbonate. The organic phase was dried (MgSO$_4$) and concentrated in vacuo to give the title compound (6.02 g). LCMS RT=3.22 min.

v) 3-({2-[4-(2-Bromoethyl)phenoxy]ethoxy}methyl)benzonitrile

A mixture of 2-(4-{2-[(3-cyanobenzyl)oxy]ethoxy}phenyl)ethyl methanesulfonate (6.02 g) and tetrabutylammonium bromide (15.5 g) in acetonitrile (150 ml) was heated at 50° C. for 18 h. The solvent was removed in vacuo and the residue partitioned between ethyl acetate and water. The organic phase was washed with brine, dried (MgSO$_4$), and concentrated in vacuo to give the title compound (5.48 g). LCMS RT=3.60 min.

vi) 3-({2-[4-(2-{[(2R)-2-(2,2-Dimethyl-4H-1,3-benzodioxin-6-yl)-2-hydroxyethyl]amino}ethyl)phenoxy]ethoxy}methyl)benzonitrile A solution of (1R)-2-amino-1-(2,2-dimethyl-4H-1,3-benzodioxin-6-yl)ethanol (4.42 g) in N,N-dimethylformamide (150 mL) was treated with diisopropylethylamine (6.89 ml) and 3-({2-[4-(2-bromoethyl)phenoxy]ethoxy}methyl) (5.48 g). The reaction mixture was heated at 50° C. for 17 h. The reaction mixture was concentrated in vacuo and partitioned between ethyl acetate and water. The aqueous phase was extracted with ethyl acetate and the combined organic phase washed with brine, dried (MgSO$_4$) and concentrated in vacuo. The residue was purified by chromatography (SPE, eluted with gradient between dichloromethane and 6% methanol in dichloromethane) to give the title compound (4.6 g). LCMS RT=2.67 min.

vii) 3-({2-[4-(2-{[(2R)-2-(2,2-Dimethyl-4H-1,3-benzodioxin-6-yl)-2-hydroxyethyl]amino}ethyl)phenoxy]ethoxy}methyl)benzamide A solution of 3-({2-[4-(2-{[(2R)-2-(2,2-dimethyl-4H-1,3-benzodioxin-6-yl)-2-hydroxyethyl]amino}ethyl)phenoxy]ethoxy}methyl)benzonitrile (4.6 g) in tetrahydrofuran (70 ml) was treated with potassium trimethylsilanoate (9.32 g) and heated at 70° C. for 71 h. The reaction mixture was concentrated in vacuo and partitioned between ethyl acetate and water. The aqueous phase was extracted with ethyl acetate and the combined organic phase washed with brine, dried (MgSO₄) and concentrated in vacuo. The residue was purified by chromatography (SPE, eluted with a gradient between dichloromethane and 10% methanol in dichloromethane) to give the title compound (1.01 g). LCMS RT=2.42 min.

viii) 3-[(2-{4-[2-({(2R-2-Hydroxy-2-[4-hydroxy-3-(hydroxymethyl)phenyl]ethyl}amino)ethyl]phenoxy}ethoxy)methyl]benzamide 3-({2-[4-(2-{[(2R)-2-(2,2-Dimethyl-4H-1,3-benzodioxin-6-yl)-2-hydroxyethyl]amino}ethyl)phenoxy]ethoxy}methyl)benzamide was dissolved in methanol and applied to a SCX-2 cartridge. Elution using 1% ammonia in methanol, removal of the solvent in vacuo, and purification by chromatography (SPE, eluted with a gradient between 10% methanol in dichloromethane and 16% methanol in dichloromethane) gave the title compound (0.57 g). LCMS RT=2.11 min ES+ve m/z 481 (MH)⁺

EXAMPLE 49 i) 3-[(2-{4-[2-({(2R)-2-Hydroxy-2-[4-hydroxy-3-(hydroxymethyl)phenyl]ethyl}amino)ethyl]phenoxy}ethoxy)methyl]benzamide hydrochloride salt To a solution of 3-[(2-{4-[2-({(2R)-2-hydroxy-2-[4-hydroxy-3-(hydroxymethyl)phenyl]ethyl}amino)ethyl]phenoxy}ethoxy)methyl]benzamide (25 mg) in iso-propanol (0.45 ml) was added hydrochloric acid (12M, 5.1 µl). A heat-cool cycle was applied between 0° C. and 40° C., and the mixture agitated for 90 h. The precipitate was filtered to give the title compound (20 mg). Mp 151-153° C.; ¹H NMR δ (CD₃OD, 400 MHz) 7.88 (1H, br s), 7.78 (1H, br d, J 8 Hz), 7.55 (1H, d, J 8 Hz), 7.43 (1H, t, J 8 Hz), 7.34 (1H, br d, J 2 Hz), 7.22-7.13 (3H, m), 6.92 (2H, br d, J 8 Hz), 6.77 (1H, d, J 8 Hz), 4.65 (4H, d, J 7 Hz), 4.16-4.11 (2H, br t, J 4 Hz), 3.87-3.81 (2H, br t, J 4 Hz), 3.27-3.20 (2H, br t, J 8 Hz), 2.98-2.90 (2H, m).

Biological Activity

The potencies of the aforementioned compounds were determined using frog melanophores transfected with the human beta 2 adrenoreceptor. The cells were incubated with melatonin to induce pigment aggregation. Pigment dispersal was induced by compounds acting on the human beta 2 adrenoreceptor. The beta 2 agonist activity of test compounds was assessed by their ability to induce a change in light transmittance across a melanophore monolayer (a consequence of pigment dispersal). At the human beta 2 adrenoreceptor, compounds of examples 1-47 had $IC_{50}$ values below 1 µM.

Potency at other beta adrenoreceptor subtypes was determined using chinese hamster ovary cells transfected with either the human beta 1 adrenoreceptor or the human beta 3 adrenoreceptor. Agonist activity was assessed by measuring changes in intracellular cyclic AMP.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:
1. A compound of formula (I):

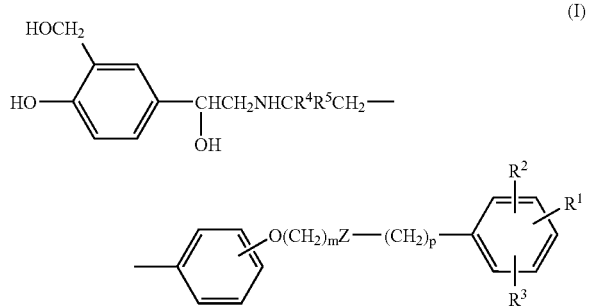

or a salt, or solvate thereof, wherein:
m is an integer of from 2 to 4;
p is an integer of from 1 to 4, preferably 1;
Z is O or $CH_2$—
$R^1$ is selected from hydrogen, $C_{1-6}$alkyl, $C_{1-6}$alkoxy, hydroxy, cyano, nitro, halo, $C_{1-6}$haloalkyl, $XCO_2R^8$, —$XC(O)NR^7R^8$, —$XNR^6C(O)R^7$, —$XNR^6C(O)NR^7R^8$, —$XNR^6C(O)NC(O)NR^7R^8$, —$XNR^6SO_2R^7$, —$XSO_2NR^9R^{10}$, —$XNR^6SO_2NR^9R^{10}$, $XSR^6$, $XSOR^6$, $XSO_2R^6$, —$XNR^7R^8$, —$XNR^6C(O)OR^7$,
or $R^1$ is selected from —X-aryl, —X-hetaryl, or —X-(aryloxy), each optionally substituted by 1 or 2 groups independently selected from hydroxy, $C_{1-6}$alkoxy, halo, $C_{1-6}$alkyl, $C_{1-6}$haloalkyl, —$NR^6C(O)R^7$, $SR^6$, $SOR^6$, —$SO_2R^6$, —$SO_2NR^9R^{10}$, —$CO_2R^8$, —$NR^7R^8$, or hetaryl optionally substituted by 1 or 2 groups independently selected from hydroxy, $C_{1-6}$alkoxy, halo, $C_{1-6}$alkyl, or $C_{1-6}$haloalkyl;
X is —$(CH_2)_q$— or $C_{2-6}$ alkenylene;
q is an integer from 0 to 6, preferably 0 to 4;
$R^6$ and $R^7$ are independently selected from hydrogen, $C_{1-6}$alkyl, $C_{3-7}$cycloalkyl, aryl, hetaryl, hetaryl($C_{1-6}$alkyl)- and aryl($C_{1-6}$alkyl)- and $R^6$ and $R^7$ are each independently optionally substituted by 1 or 2 groups independently selected from halo, $C_{1-6}$alkyl, $C_{3-7}$ cycloalkyl, $C_{1-6}$ alkoxy, $C_{1-6}$haloalkyl, —NHC(O)($C_{1-6}$alkyl), —$SO_2(C_{1-6}$alkyl), —$SO_2$(aryl), —$CO_2H$, and —$CO_2(C_{1-4}$alkyl), —$NH_2$, —NH($C_{1-6}$alkyl), aryl($C_{1-6}$alkyl)-, aryl($C_{2-6}$alkenyl)-, aryl($C_{2-6}$alkynyl)—, hetaryl($C_{1-6}$alkyl)-, —$NHSO_2$aryl, —NH(hetaryl$C_{1-6}$alkyl), —$NHSO_2$hetaryl, —$NHSO_2$($C_{1-6}$alkyl), —NHC(O)aryl, or —NHC(O)hetaryl;
or where $R^1$ is —$XNR^6C(O)OR^7$, $R^6$ and $R^7$ may, together with the —NC(O)O— portion of the group $R^1$ to which they are bonded, form a saturated or unsaturated ring, preferably a 5-, 6-, or 7-membered ring, for example an oxazolidine ring, such as oxazolidine-2,4-dione,
or where $R^1$ is —$XNR^6C(O)NR^7R^8$, $R^6$ and $R^7$ may, together with the —NC(O)N— portion of the group $R^1$ to which they are bonded, form a saturated or unsaturated ring, preferably a 5-, 6-, or 7-membered ring, for example an imidazolidine ring, such as imidazolidine-2,4-dione;

$R^8$ is selected from hydrogen, $C_{1-6}$alkyl and $C_{3-7}$cycloalkyl;

or $R^7$ and $R^8$, together with the nitrogen atom to which they are bonded, form a 5-, 6- or 7-membered nitrogen-containing ring;

$R^9$ and $R^{10}$ are independently selected from hydrogen, $C_{1-6}$alkyl, $C_{3-7}$cycloalkyl, $CO_2(C_{1-4}$alkyl), aryl, hetaryl, hetaryl($C_{1-6}$alkyl)- and aryl($C_{1-6}$alkyl)-, or $R^9$ and $R^{10}$, together with the nitrogen to which they are bonded, form a 5-, 6-, or 7-membered nitrogen containing ring;

and $R^9$ and $R^{10}$ are each optionally substituted by one or two groups independently selected from halo, $C_{1-6}$alkyl, and $C_{3-7}$cycloalkyl, $C_{1-6}$haloalkyl;

$R^2$ is selected from hydrogen, hydroxy, $C_{1-6}$alkyl, $C_{1-6}$alkoxy, halo, aryl, aryl($C_{1-6}$alkyl)-, $C_{1-6}$haloalkoxy, and $C_{1-6}$haloalkyl;

$R^3$ is selected from hydrogen, hydroxy, $C_{1-6}$alkyl, $C_{1-6}$alkoxy, halo, aryl, aryl($C_{1-6}$alkyl)-, $C_{1-6}$haloalkoxy, and $C_{1-6}$haloalkyl; and $R^4$ and $R^5$ are independently selected from hydrogen and $C_{1-4}$ alkyl with the proviso that the total number of carbon atoms in $R^4$ and $R^5$ is not more than 4.

2. A compound according to claim 1 wherein $R^1$ is selected from hydrogen, $C_{1-6}$alkyl, hydroxy, cyano, nitro, halo, $C_{1-6}$haloalkyl, $XCO_2R^8$, —XC(O)NR$^7$R$^8$, —XNR$^6$C(O)R$^7$, —XNR$^6$C(O)NR$^7$R$^8$, —XNR$^6$C(O)NC(O)NR$^7$R$^8$, —XNR$^6$SO$_2$R$^7$, —XSO$_2$NR$^9$R$^{10}$, —XSR6, —XSOR$^6$, —XSO$_2$R$^6$, —XNR$^7$R$^8$, —XNR$^6$C(O)OR$^7$, or $R^1$ is selected from —X-aryl, —X-hetaryl, or —X-(aryloxy), each optionally substituted by 1 or 2 groups independently selected from hydroxy, $C_{1-6}$alkoxy, halo, $C_{1-6}$alkyl, C1-6haloalkyl, —NR$^6$C(O)R$^7$, SR$^6$, SOR$^6$, —SO$_2$R$^6$, —SO$_2$NR$^9$R$^{10}$, —CO$_2$R$^8$, —NR$^7$R$^8$, or hetaryl optionally substituted by 1 or 2 groups independently selected from hydroxy, $C_{1-6}$alkoxy, halo, $C_{1-6}$alkyl, or $C_{1-6}$haloalkyl;

wherein $R^6$, $R^7$, $R^8$, are as defined in claim 1 and $R^9$ and $R^{10}$ are independently selected from hydrogen, $C_{1-6}$alkyl, $C_{3-7}$cycloalkyl, aryl, hetaryl, hetaryl($C_{1-6}$alkyl)- and aryl($C_{1-6}$alkyl)-, or $R^9$ and $R^{10}$, together with the nitrogen to which they are bonded, form a 5-, 6-, or 7-membered nitrogen containing ring;

and $R^9$ and $R^{10}$ are each optionally substituted by one or two groups independently selected from halo, $C_{1-6}$alkyl, and $C_{3-7}$cycloalkyl, $C_{1-6}$haloalkyl.

3. A compound according to claim 1 wherein the group $R^1$ is selected from hydroxy, —XC(O)NR$^7$R$^8$, and —XSO$_2$NR$^9$R$^{10}$.

4. A compound according to claim 1 wherein the compound is selected from the group consisting of:

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}urea;

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}dicar bonimidic diamide;

4-((1R)-2-{[2-(4-{2-[(3-Fluorobenzyl)oxy]ethoxy}phenyl)ethyl]amino}-1-hydroxyethyl)-2-(hydroxymethyl)phenol;

2-(Hydroxymethyl)-4-((1R)-1-hydroxy-2-{[2-(4-{2-[(3-methylbenzyl)oxy]ethoxy}phenyl)ethyl]amino}ethyl)phenol;

4-((1R)-2-{[2-(4-{2-[(3-Chlorobenzyl)oxy]ethoxy}phenyl)ethyl]amino}-1-hydroxyethyl)-2-(hydroxymethyl)phenol;

4-((1R)-1-Hydroxy-2-{[2-(4-{2-[(3-iodobenzyl)oxy]ethoxy}phenyl)ethyl]amino}ethyl)-2-(hydroxymethyl)phenol;

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}acetamide;

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}nicotinamide;

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}-2-furamide;

3-[(2-{4-[2-({(2R)-2-Hydroxy-2-[4-hydroxy-3-(hydroxymethyl)phenyl]ethyl}amino)ethyl]phenoxy}ethoxy)methyl]benzamide;

3-[(2-{4-[2-({(2R)-2-Hydroxy-2-[4-hydroxy-3-(hydroxymethyl)phenyl]ethyl}amino)ethyl]phenoxy}ethoxy)methyl]benzonitrile;

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}methanesulfonamide;

4-{(1R)-2-[(2-{4-[2-)Benzyloxy]ethoxy]phenyl}ethyl)amino]-1-hydroxyethyl}-2-(hydroxymethyl)phenol;

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}-N'-phenylurea;

4-((1R)-1-Hydroxy-2-{[2-(4-{2-[(3-hydroxybenzyl)oxy]ethoxy}phenyl)ethyl]amino}ethyl)-2-(hydroxymethyl)phenol;

4-{(1R)-2-[((1S)-2-{4-[2-(Benzyloxy)ethoxy]phenyl}-1-methylethyl)amino]-1-hydroxyethyl}-2-(hydroxymethyl)phenol;

4-{(1R)-2-[((1R)-2-{4-[2-(Benzyloxy)ethoxy]phenyl}-1-methylethyl)amino]-1-hydroxyethyl}-2-(hydroxymethyl)phenol;

3-[(2-{4-[2-({(2R)-2-Hydroxy-2-[4-hydroxy-3-(hydroxymethyl)phenyl]ethyl}amino)ethyl]phenoxy}ethoxy)methyl]benzenesulf onamide;

3-[(2-{4-[2-({(2R)-2-Hydroxy-2-[4-hydroxy-3-(hydroxymethyl)phenyl]ethyl}amino)ethyl]phenoxy}ethoxy)methyl]-N-isopropylbenzenesulfonamide;

3-[(2-{4-[2-({(2R)-2-Hydroxy-2-[4-hydroxy-3-(hydroxymethyl)phenyl]ethyl}amino)ethyl]phenoxy}ethoxy)methyl]benzoic acid;

4-((1R)-2-{[2-(4-{2-[(4-Fluorobenzyl)oxy]ethoxy}phenyl)ethyl]amino}-1-hydroxyethyl)-2-(hydroxymethyl)phenol;

4-((1R)-2-{[2-(4-{2-[(2,6-Dichlorobenzyl)oxy]ethoxy}phenyl)ethyl]amino}-1-hydroxyethyl)-2-(hydroxymethyl)phenol;

N-{3-[(2-{4-[2-({(2R)-2-Hydroxy-2-[4-hydroxy-3-(hydroxymethyl)phenyl]ethyl}amino)ethyl]phenoxy}ethoxy)methyl]phenyl}sulfamide, N-(tert-butoxycarbonyl)-N'-{3-[(2-{4-[2-({(2R)-2-hydroxy-2-[4-hydroxy-3-(hydroxymethyl)phenyl]ethyl}amino)ethyl]phenoxy}ethoxy)methyl]phenyl}sulfamide;

4-[(1R)-2-({2-[4-(2-{[3-(Cyclopentylsulfonyl)benzyl]oxy}ethoxy)phenyl]ethyl}amino)-1-hydroxyethyl]-2-(hydroxymethyl)phenol;

4-[(1R)-2-({2-[4-(2-{[3-(Cyclopentylsulfinyl)benzyl]
  oxy}ethoxy)phenyl]ethyl}amino)-1-hydroxyethyl]-2-
  (hydroxymethyl)phenol;
4-((1R)-1-Hydroxy-2-{[2-(4-{2-[(4-isopropoxybenzyl)
  oxy]ethoxy}phenyl)ethyl]amino}ethyl)-2-(hydroxym-
  ethyl)phenol;
4-((1R)-1-Hydroxy-2-{[2-(4-{2-[(4-hydroxybenzyl)oxy]
  ethoxy}phenyl)ethyl]amino}ethyl)-2-(hydroxymethyl)
  phenol;
3-[(2-{4-[2-({(2R)-2-Hydroxy-2-[4-hydroxy-3-(hy-
  droxymethyl)phenyl]ethyl}amino)ethyl]
  phenoxy}ethoxy)methyl]-N-isopropylbenzamide;
N-Cyclohexyl-3-[(2-{4-[2-({(2R)-2-hydroxy-2-[4-hy-
  droxy-3-(hydroxymethyl)phenyl]ethyl}amino)ethyl]
  phenoxy}ethoxy)methyl]benzamide;
N-Cyclohexyl-3-[(2-{4-[2-({(2R)-2-hydroxy-2-[4-hy-
  droxy-3-(hydroxymethyl)phenyl]ethyl}amino)ethyl]
  phenoxy}ethoxy)methyl]benzenesulfonamide;
3-[(2-{4-[2-({(2R)-2-Hydroxy-2-[4-hydroxy-3-(hy-
  droxymethyl)phenyl]ethyl}amino)ethyl]
  phenoxy}ethoxy)methyl]-N-methylbenzenesulfona-
  mide;
4-[(1R)-1-Hydroxy-2-({2-[4-(2-{[3-(isopropylsulfinyl)
  benzyl]oxy}ethoxy)phenyl]ethyl}amino)ethyl]-2-(hy-
  droxymethyl)phenol;
4-[(1R)-1-Hydroxy-2-({2-[4-(2-{[3-(isopropylsulfonyl)
  benzyl]oxy}ethoxy)phenyl]ethyl}amino)ethyl]-2-(hy-
  droxymethyl)phenol;
2-(Hydroxymethyl)-4-[(1R)-1-hydroxy-2-({2-[4-(4-phe-
  nylbutoxy)phenyl]ethyl}amino)ethyl]phenol;
4-{(1R)-1-Hydroxy-2-[(2-{4-[4-(3-hydroxyphenyl)bu-
  toxy]phenyl}ethyl)amino]ethyl}-2-(hydroxymethyl)
  phenol;
4-((1R)-2-{[2-(4-{4-[3-(Cyclopentylsulfinyl)phenyl]
  butoxy}phenyl)ethyl]amino}-1-hydroxyethyl)-2-(hy-
  droxymethyl)phenol;
4-{(1R)-2-[(2-{4-[4-(2,6-Dichlorophenyl)butoxy]
  phenyl}ethyl)amino]-1-hydroxyethyl}-2-(hydroxym-
  ethyl)phenol;

3-(4-{4-[2-({(2R)-2-Hydroxy-2-[4-hydroxy-3-(hy-
  droxymethyl)phenyl]ethyl}amino)ethyl]
  phenoxy}butyl)benzenesulfonamide N-[3-(4-{2-({
  (2R)-2-Hydroxy-2-[4-hydroxy-3-(hydroxymethyl)
  phenyl]ethyl}amino)ethyl]phenoxy}butyl)phenyl]
  urea;
3-(4-{4-[2-({(2R)-2-Hydroxy-2-[4-hydroxy-3-(hy-
  droxymethyl)phenyl]ethyl}amino)ethyl]
  phenoxy}butyl)benzoic acid;
3-(4-{4-[2-({(2R)-2-Hydroxy-2-[4-hydroxy-3-(hy-
  droxymethyl)phenyl]ethyl}amino)ethyl]
  phenoxy}butyl)benzonitrile;
3-(4-{4-[2-({(2R)-2-Hydroxy-2-[4-hydroxy-3-(hy-
  droxymethyl)phenyl]ethyl}amino)ethyl]
  phenoxy}butyl)benzamide;

3'-[(2-{4-[2-({(2R)-2-Hydroxy-2-[4-hydroxy-3-(hy-
  droxymethyl)phenyl]ethyl}amino)ethyl]
  phenoxy}ethoxy)methyl]-1,1'-biphenyl-3-carboxylic
  acid;
N-Butyl-3-[(2-{4-[2-({(2R)-2-hydroxy-2-[4-hydroxy-3-
  (hydroxymethyl)phenyl]ethyl}amino)ethyl]
  phenoxy}ethoxy)methyl]benzamide;
3-[(2-{4-[2-({(2R)-2-Hydroxy-2-[4-hydroxy-3-(hy-
  droxymethyl)phenyl]ethyl}amino)ethyl]
  phenoxy}ethoxy)methyl]-N-pentylbenzamide;
3-[(2-{4-[2-({(2R)-2-Hydroxy-2-[4-hydroxy-3-(hy-
  droxymethyl)phenyl]ethyl}amino)ethyl]
  phenoxy}ethoxy)methyl]-N-isobutylbenzamide; and
3-[(2-{4-[2-({(2R)-2-Hydroxy-2-[4-hydroxy-3-(hy-
  droxymethyl)phenyl]ethyl}amino)ethyl]
  phenoxy}ethoxy)methyl]-N-isopentylbenzamide;
or a salt thereof, or a solvate thereof.

5. A compound according to claim 1 which is 3-[(2-{4-[2-({(2R)-2-Hydroxy-2-[4-hydroxy-3-(hydroxymethyl)phenyl]ethyl}amino)ethyl]phenoxy}ethoxy)methyl]benzamide; or a salt thereof, or a solvate thereof.

6. A method for the treatment of a clinical condition in a mammal, for which a selective $\beta_2$-adrenoreceptor agonist is indicated, wherein said clinical condition is selected from the group consisting of asthma, chronic obstructive pulmonary diseases respiratory tract infection, and upper respiratory tract disease, which comprises administrating a therapeutically effective amount of a compound according to claim 1 or a pharmaceutically acceptable salt, or solvate thereof.

7. A pharmaceutical formulation comprising a compound according to claim 1, or a pharmaceutically acceptable salt, or solvate thereof, and a pharmaceutically acceptable carrier or excipient, and optionally one or more other therapeutic ingredients.

8. A process for the preparation of a compound of formula (I), according to claim 1, or a salt, or solvate thereof, wherein said process is selected from the group consisting of (a), (b), (c) and (d):

(a) deprotecting a protected intermediate of formula (II):

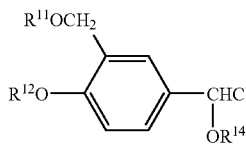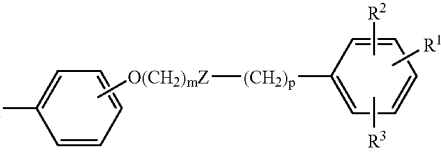

(II)

or a salt or solvate thereof, wherein $R^1$, $R^2$, $R^3$, $R^4$, $R^5$, Z, m, and p are as defined for the compound of formula (I), and $R^{11}$, $R^{12}$, $R^{13}$ and $R^{14}$ are each independently either hydrogen or a protecting group provided that at least one of $R^{11}$, $R^{12}$, $R^{13}$ and $R^{14}$ is a protecting group;

(b) alkylating an amine of formula (XIII)

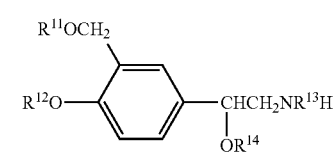

(XIII)

wherein $R^{11}$, $R^{12}$, $R^{13}$ and $R^{14}$ are each independently either hydrogen or a protecting group, with a compound of formula (XIV):

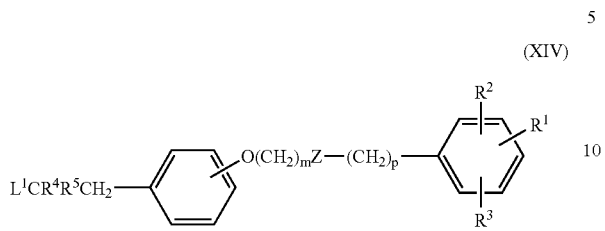

(XIV)

wherein $R^1$, $R^2$, $R^3$, $R^4$, $R^5$, Z, m, and p are as defined for the compound of formula (I) and $L^1$ is a leaving group;

(c) reacting a compound of formula (XV):

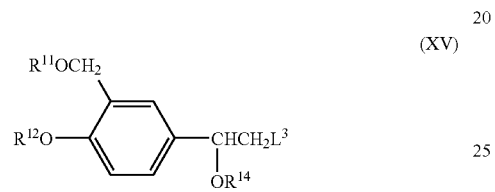

(XV)

wherein $R^{11}$ $R^{12}$ and $R^{14}$ are as hereinbefore defined and $L^3$ is a leaving group, with an amine of formula (XVI):

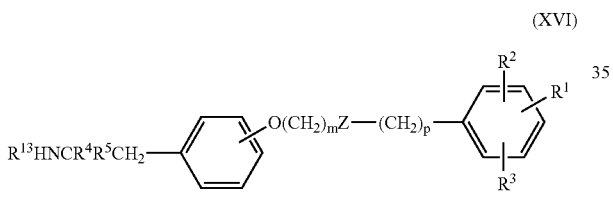

(XVI)

(d) reacting a compound of formula (XIII):

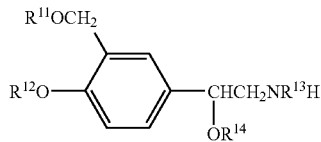

(XIII)

wherein $R^{11}$, $R^{12}$, $R^{13}$ and $R^{14}$ are each independently either hydrogen or a protecting group provided that at least one of $R^{11}$, $R^{12}$, $R^{13}$ and $R^{14}$ is a protecting group with a compound of formula (XVII):

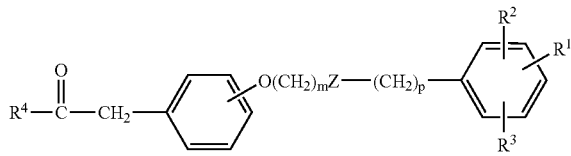

(XVII)

wherein $R^1$, $R^2$, $R^3$, $R^4$, Z, m, and p are as defined for the compounds of formula (I), under conditions suitable to effect reductive amination, wherein processes (a), (b), (c), or (d) may optionally be followed by one or more of the following steps in any order:
(i) optional removal of any protecting groups;
(ii) optional separation of an enantiomer from a mixture of enantiomers;
(iii) optional conversion of the product to a corresponding salt, or solvate thereof.

9. A method according to claim 6, wherein the mammal is a human.

10. A compound according to claim 1 wherein $R^1$ is —XC(O)NR$^7$R$^8$.

\* \* \* \* \*